(12) United States Patent
Nakamae et al.

(10) Patent No.: US 12,385,000 B2
(45) Date of Patent: Aug. 12, 2025

(54) CELL CULTURE ANALYZER AND CELL CULTURE ANALYSIS METHOD USING SAME, ADDITIVE SUPPLY UNIT AND CELL CULTURE ANALYZER PROVIDED THEREWITH, AND SENSOR UNIT AND CELL CULTURE ANALYZER PROVIDED THEREWITH

(71) Applicant: PHC Holdings Corporation, Tokyo (JP)

(72) Inventors: Kenta Nakamae, Ehime (JP); Masahiro Kouge, Ehime (JP); Masayuki Saiki, Ehime (JP); Shingo Otani, Ehime (JP); Seiitirou Iketani, Ehime (JP); Fumiya Matsubara, Ehime (JP); Akira Nishio, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 690 days.

(21) Appl. No.: 17/791,675

(22) PCT Filed: Mar. 9, 2021

(86) PCT No.: PCT/JP2021/009340
§ 371 (c)(1),
(2) Date: Jul. 8, 2022

(87) PCT Pub. No.: WO2021/193029
PCT Pub. Date: Sep. 30, 2021

(65) Prior Publication Data
US 2023/0029803 A1 Feb. 2, 2023

(30) Foreign Application Priority Data

Mar. 25, 2020 (JP) ................................. 2020-054308
Mar. 25, 2020 (JP) ................................. 2020-054315
(Continued)

(51) Int. Cl.
*C12M 1/34* (2006.01)
*C12M 1/00* (2006.01)
*C12M 1/06* (2006.01)

(52) U.S. Cl.
CPC ............ *C12M 41/30* (2013.01); *C12M 23/34* (2013.01); *C12M 27/02* (2013.01); *C12M 29/06* (2013.01); *C12M 29/24* (2013.01)

(58) Field of Classification Search
CPC ...... C12M 41/30; C12M 41/14; C12M 41/00; C12M 23/34; C12M 23/12; C12M 27/02; C12M 29/06; C12M 29/24; C12M 29/14
See application file for complete search history.

(56) References Cited

U.S. PATENT DOCUMENTS 6,137,108 A * 10/2000 DeThomas ............... G01J 3/42
356/342
6,326,058 B1 12/2001 Biebuyck et al.
(Continued)

FOREIGN PATENT DOCUMENTS

EP 3 278 400 10/2016
JP 6-165624 6/1994
(Continued)

OTHER PUBLICATIONS

Extended European Search Report issued Aug. 17, 2023 in corresponding European Patent Application No. 21773447.4.
(Continued)

*Primary Examiner* — Michael L Hobbs
(74) *Attorney, Agent, or Firm* — Wenderoth, Lind & Ponack, L.L.P.

(57) ABSTRACT

A cell culture analyzer comprises a stirring member and an air discharge and intake unit. The stirring member is used in a state of being immersed in a medium, and has a liquid discharge and intake port for discharging or drawing in the
(Continued)

medium, and an air discharge and intake port for discharging or drawing in air in order to discharge or draw in the medium from the liquid discharge and intake port. The air discharge and intake unit is linked to the air discharge and intake port of the stirring member, and discharges or draws in the air discharged or drawn in from the air discharge and intake port.

16 Claims, 47 Drawing Sheets

(30) Foreign Application Priority Data

| Mar. 25, 2020 | (JP) | 2020-054356 |
|---|---|---|
| Mar. 25, 2020 | (JP) | 2020-054415 |
| Mar. 25, 2020 | (JP) | 2020-054464 |
| Mar. 8, 2021 | (JP) | 2021-035928 |

(56) References Cited

U.S. PATENT DOCUMENTS

| 9,170,255 | B2 | 10/2015 | Teich et al. |
|---|---|---|---|
| 9,494,577 | B2 | 11/2016 | McGarr et al. |
| 10,359,418 | B2 | 7/2019 | Teich et al. |
| 11,312,935 | B2 | 4/2022 | Makino et al. |
| 2007/0275455 | A1 | 11/2007 | Hung et al. |
| 2016/0077083 | A1 | 3/2016 | Teich et al. |
| 2018/0097309 | A1 | 4/2018 | Haspel et al. |
| 2018/0371396 | A1 | 12/2018 | Makino et al. |
| 2021/0072179 | A1 | 3/2021 | Endoh et al. |

FOREIGN PATENT DOCUMENTS

| JP | 10-276762 | 10/1998 |
|---|---|---|
| JP | 2004-112092 | 4/2004 |
| JP | 2018-113951 | 7/2018 |
| KR | 10-2017-0131904 | 12/2017 |
| WO | 2019/146788 | 8/2019 |

OTHER PUBLICATIONS

International Search Report issued Apr. 27, 2021 in International (PCT) Application No. PCT/JP2021/009340.

Notification of Reasons for Refusal issued Mar. 8, 2022 in Japanese Application No. 2021-035928.

* cited by examiner

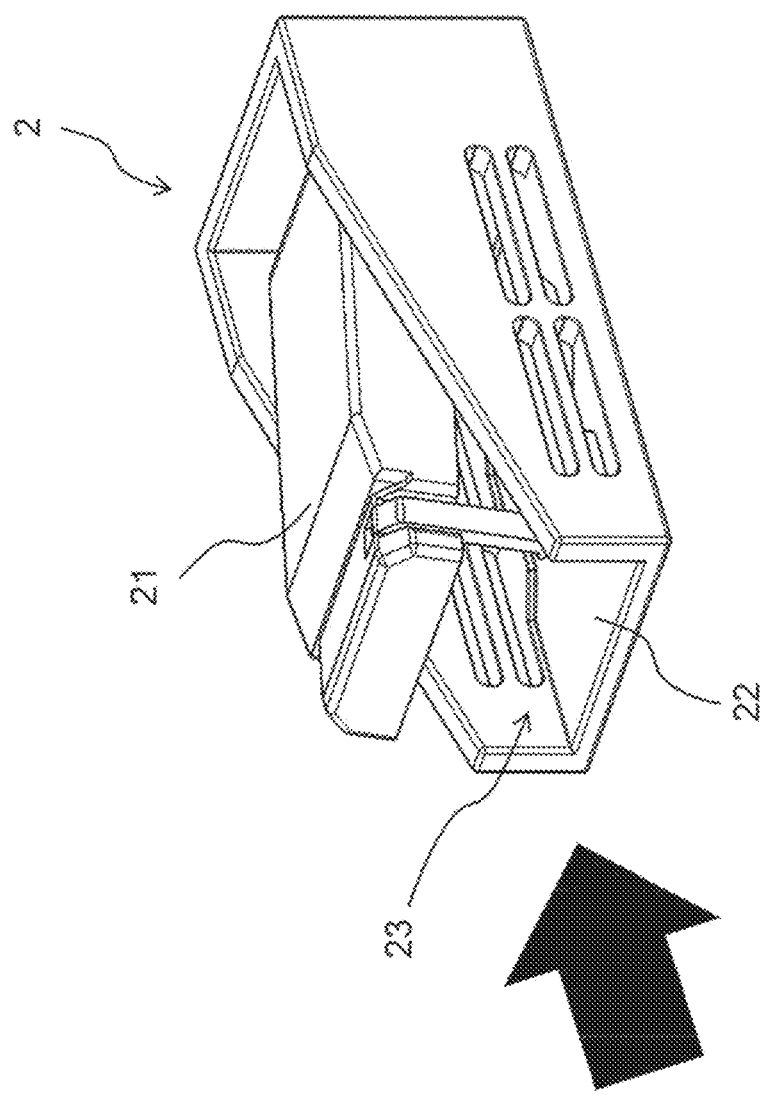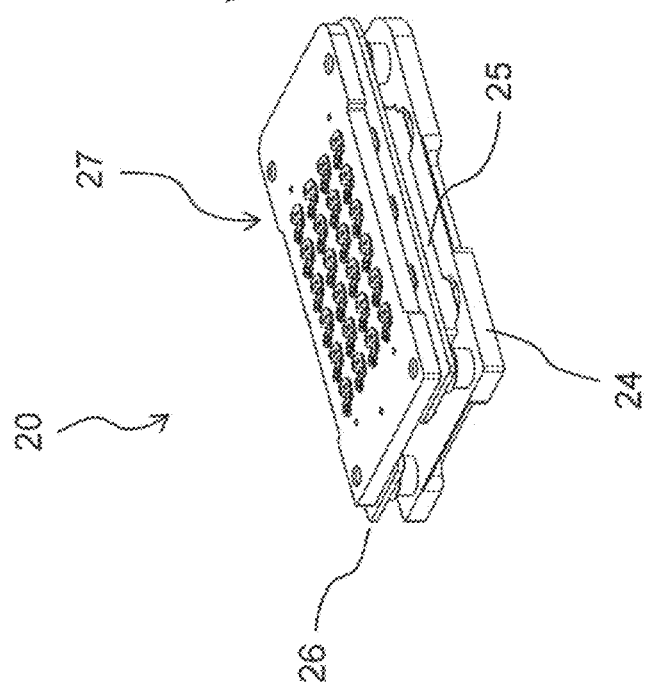
FIG. 6

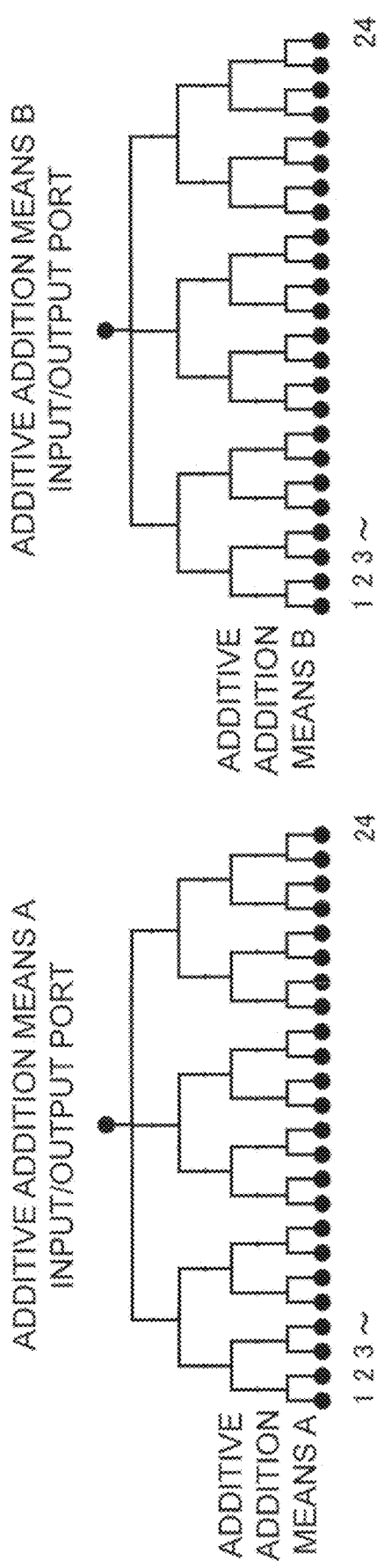
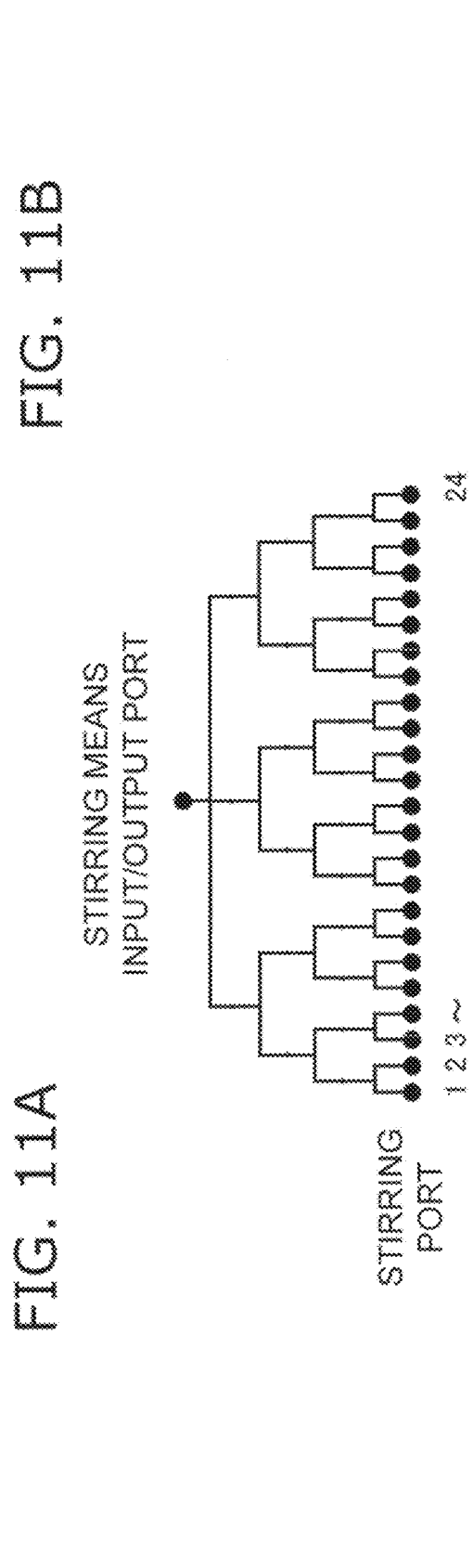
FIG. 11A
FIG. 11B
FIG. 11C

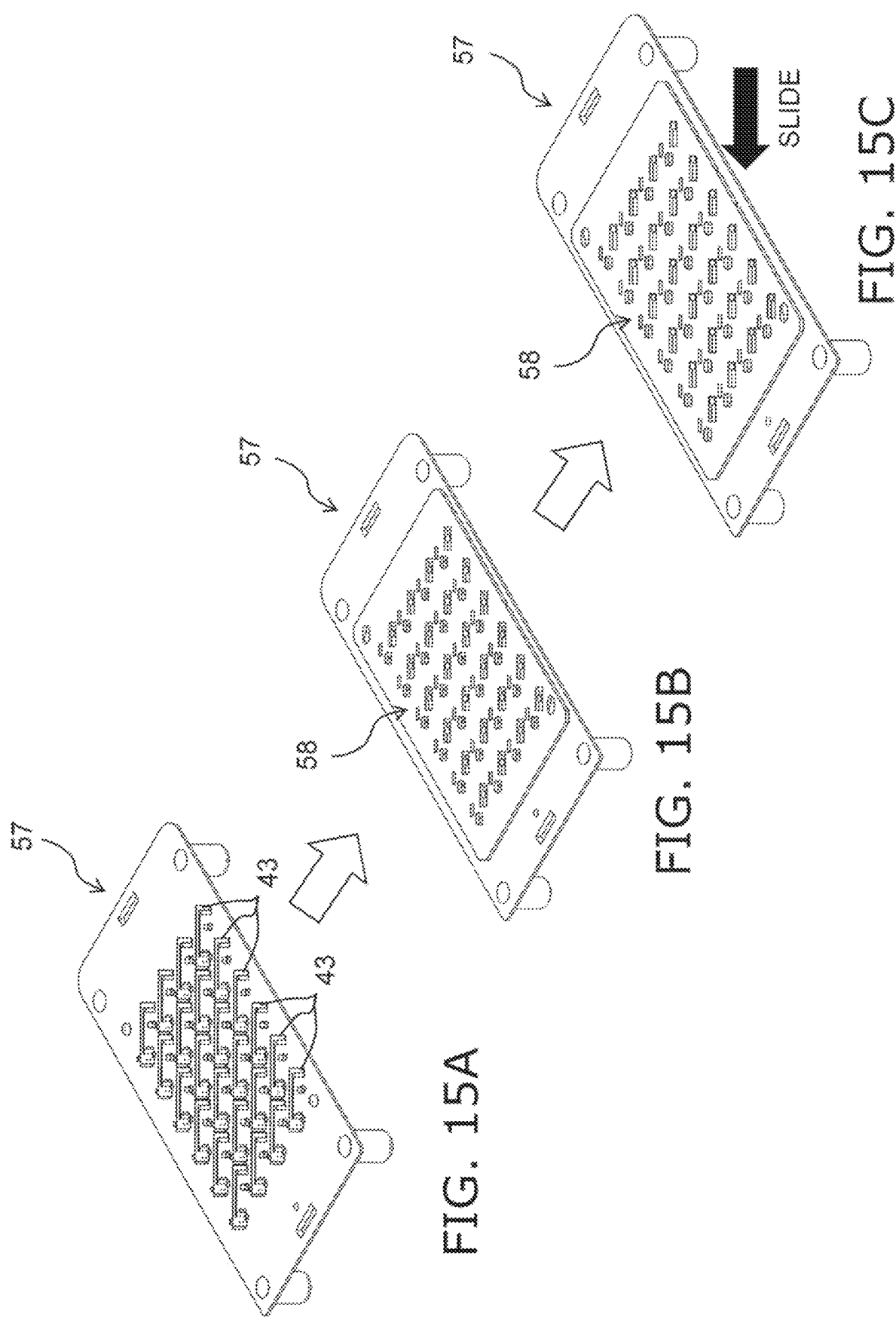

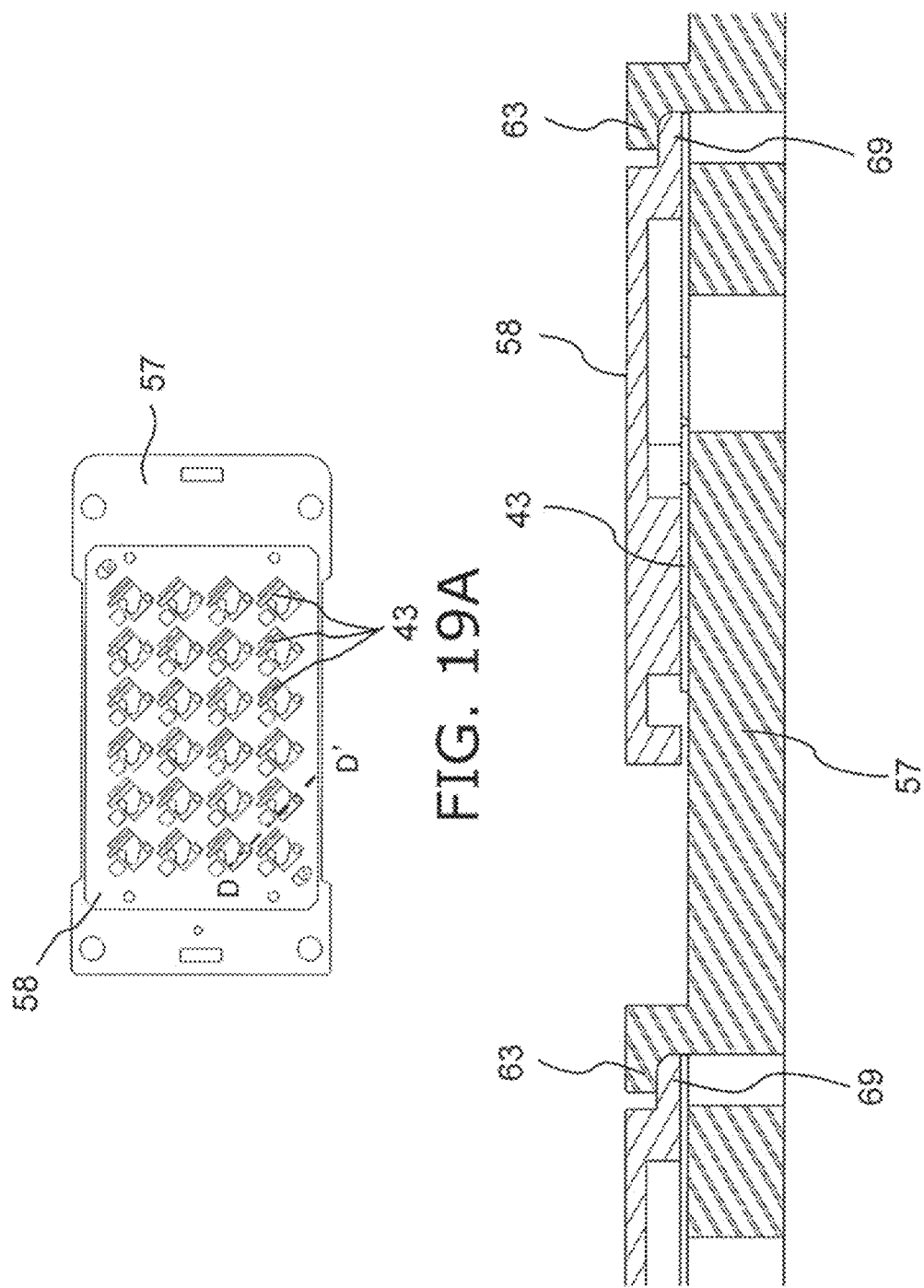

AFTER ADDITIVE DISCHARGE

AFTER FILLING WITH ADDITIVE

G-G' CROSS-SECTIONAL VIEW

DETAIL OBLIQUE VIEW OF STIRRING MEANS DISCHARGE AND INTAKE PORT

STIRRING UNDER POSITIVE PRESSURE

STIRRING UNDER NEGATIVE PRESSURE

INITIAL STATE

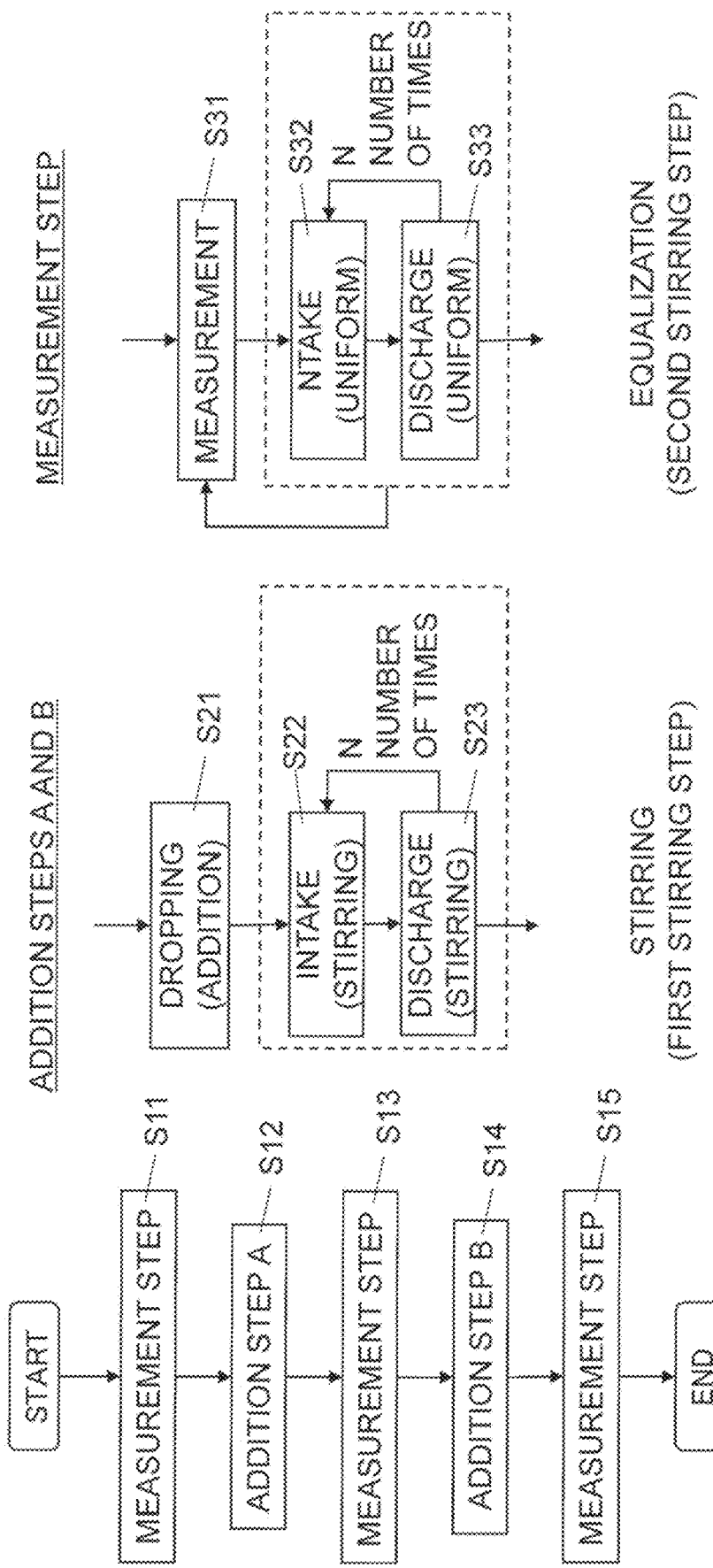

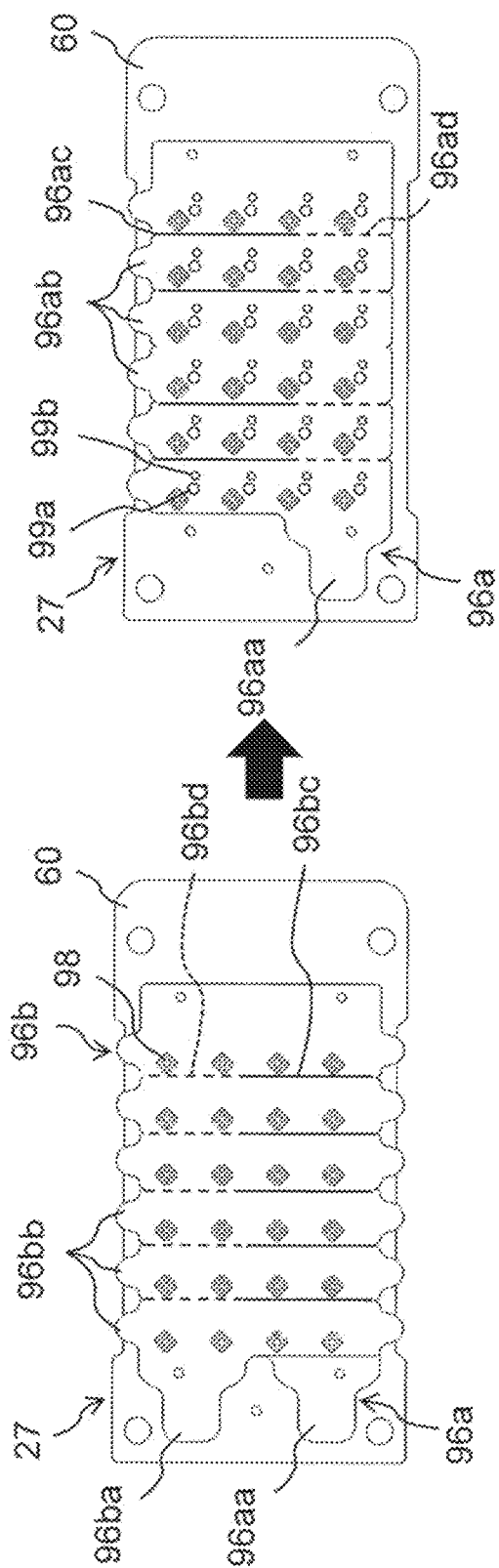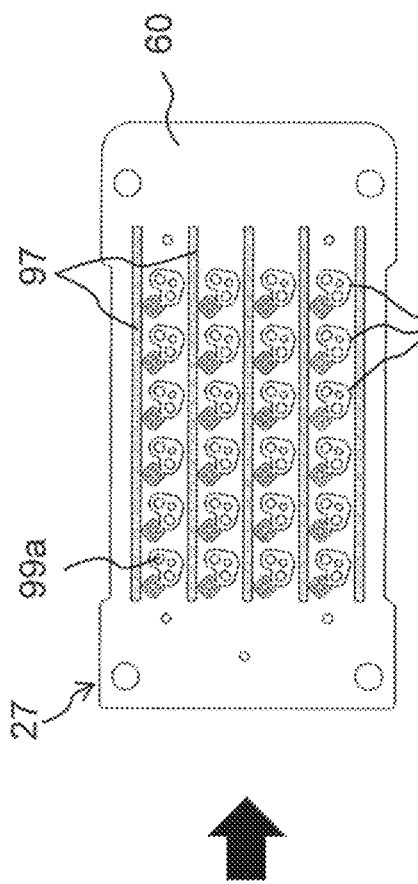
FIG. 39A
FIG. 39B
FIG. 39C

CELL CULTURE ANALYZER AND CELL CULTURE ANALYSIS METHOD USING SAME, ADDITIVE SUPPLY UNIT AND CELL CULTURE ANALYZER PROVIDED THEREWITH, AND SENSOR UNIT AND CELL CULTURE ANALYZER PROVIDED THEREWITH

TECHNICAL FIELD

The present invention relates to a cell culture analyzer used to analyze cell culture, and to a cell culture analysis method in which this analyzer is used. The present invention also relates to an additive supply member used to analyze cell culture, and to a cell culture analyzer comprising this additive supply member. Furthermore, the present invention relates to a sensor unit used to analyze cell culture, and to a cell culture analyzer comprising this sensor unit.

BACKGROUND ART

The configuration of a conventional cell culture analyzer comprises a sensor immersed in a medium in a culture vessel, a stirring member having a plunger immersed in the medium, and a drive means linked to the stirring member (for example, see Patent Literature 1).

Also, a conventional cell culture analyzer comprised a sensor immersed in a medium in a culture vessel, and an additive supply means for supplying the additive to the medium, wherein the additive supply means had an additive container with an opening for supplying the medium into the culture vessel, and an air pressure supply means for applying air pressure into the additive container (see, for example, Patent Literature 2).

Furthermore, the configuration of a conventional cell culture analyzer comprised a board provided with a plurality of openings, sensors disposed in these openings, and an additive container (see, for example, Patent Literature 2).

That is, with a conventional cell culture analyzer, in performing cell culture analysis, the electrode portion of the sensor was immersed from above in a state in which the medium and the cells had been put in a plurality of culture vessels disposed side by side under the board, and the additive was added dropwise from the additive container into the culture vessel at a predetermined timing in the progress of the cell culture.

Furthermore, a conventional cell culture analyzer comprised a sensor immersed in a medium in a culture vessel, and an additive addition member for supplying the additive to the medium. The additive addition member had an additive container with an opening for supplying the additive into the culture vessel, and an air pressure supply member for applying air pressure into the additive container. The additive container had a cylindrical shape having the opening underneath, and the lower portion of the cylindrical additive container was formed so that its outer peripheral diameter decreased toward the lower end (see, for example, Patent Literature 3).

With the configuration of a conventional cell culture analyzer, the sensor was fixed to a through-hole portion provided to the board, and a lead wire for extracting a signal was connected to this sensor.

More specifically, with a conventional cell culture analyzer, a sensor for monitoring the state of the medium was inserted into the cell culture vessel, this sensor was provided with an electrical connection terminal, and a lead connected to this connection terminal was connected to an external control unit (see, for example, Patent Literature 4).

A cell culture analyzer having a cartridge that mates with a plate provided with a plurality of cell culture vessels has also been disclosed.

This cell culture analyzer has a sensor that takes measurements inside each culture vessel, a plurality of openings into which these sensors are inserted are provided to a cartridge, and the sensor and a fiber cable are connected in each opening. These fiber cables are connected to an external control unit (see, for example, Patent Literature 5).

CITATION LIST

Patent Literature

Patent Literature 1: U.S. Pat. No. 6,326,058
Patent Literature 2: U.S. Pat. No. 10,359,418
Patent Literature 3: U.S. Pat. No. 9,494,577
Patent Literature 4: JP-A 2004-112092
Patent Literature 5: U.S. Pat. No. 9,170,255

SUMMARY

Technical Problem

In the above-mentioned conventional example, the stirring member is constituted by a stirring rod whose lower end side is immersed in the medium. The medium in the culture vessel is stirred by moving the stirring rod up and down with a plunger. With a cell culture analyzer such as this, since a plurality of culture vessels are disposed adjacent to each other, a plurality of plungers corresponding to the plurality of culture vessels are also needed. As a result, a problem is that the cell culture analyzer ends up being larger.

In view of this, it is an object of the present invention to provide a cell culture analyzer that can be made more compact.

Also, in the above-mentioned conventional configuration, air pressure is applied to the additive container by the air drawn in by the air pressure supply member, and the additive in the additive container is supplied into the medium.

However, with a conventional configuration, the air drawn in by the air pressure supply member is not controlled at all outside of the cell culture analyzer, and if this air should flow into the culture vessel through the additive container, it could contaminate cell culture within the culture vessel.

In view of this, it is an object of the present invention to provide an additive supply member with which contamination of cell culture within a culture vessel can be prevented, as well as a cell culture analyzer comprising this additive supply member.

Furthermore, in the conventional example discussed above, a plurality of culture vessels are disposed side by side under a board, but when cell culture analysis is performed, the medium and cells may not go into all of the culture vessels. If this should happen, the additive container will also be disposed above the unused cell culture vessels.

Here, air pressure is applied to the upper opening of the additive container in order for the additive in the additive container to be added dropwise into the culture vessel, but if the unnecessary additive containers are not filled with additives, the air pressure applied to the plurality of additive containers will end up flowing into the empty additive container.

As a result, the appropriate level of air pressure will not be applied to the required additive containers, and it may be impossible for the additives to be added properly.

In view of this, conventionally, additive containers that were not to be used would be filled with some liquid other than an additive, such as water, which prevented the above-mentioned air leakage.

Nevertheless, filling the unused additive containers with liquid entailed a tremendous amount of work, so efficiency suffered.

Therefore, it is an object of the present invention to provide a sensor unit with which efficiency can be improved regarding cell culture analysis, as well as a cell culture analyzer comprising this sensor unit.

Furthermore, with the conventional configuration discussed above, air pressure is applied to the additive containers by the air drawn in by the air pressure supply member, so that the additives in the additive containers were supplied into the medium through the lower openings.

However, with a conventional additive container, the outer peripheral diameter of the cylindrical lower portion decreases toward the lower end, and the opening in the lower end portion is provided to the pointed portion.

Accordingly, when air pressure is applied to the additive container, the additive flows out continuously from the opening at the lower end and is continuously supplied to the culture vessel. However, this continuous inflow of additive causes a sudden environmental change for the cells contained in the culture vessel, and this can cause unfavorable stress on the cells. That is, with a conventional configuration, there is a possibility that the cells in the medium will be subjected to stress and that cell culture analysis cannot be carried out properly.

In view of this, it is an object of the present invention to provide an additive supply member with which cell culture analysis can be carried out properly, as well as a cell culture analyzer comprising this additive supply member.

With the conventional configuration discussed above, the sensor is immersed in a medium in a culture medium, for example, and senses the environment in this medium.

With a cell culture device, a plurality of culture vessels are usually used when analyzing cell culture, and therefore the number of sensors corresponding to these containers also increases. Accordingly, there is a need to make a cell culture analyzer more compact.

In view of this, it is an object of the present invention to provide a sensor unit with which a cell culture analyzer can be made more compact, as well as a cell culture analyzer comprising this sensor unit.

Solution to Problem

To achieve the stated object, the cell culture analyzer of the present invention is a cell culture analyzer that performs cell culture analysis by detecting a specific component contained in a medium that has been put in a culture vessel, and comprises a stirring member and an air discharge and intake unit. The stirring member has a liquid discharge and intake port that is used in a state of being immersed in the medium and discharges or draws in the medium, and an air discharge and intake port that discharges or draws in air in order to discharge or draw in the medium from the liquid discharge and intake port. The air discharge and intake unit is linked to the air discharge and intake port of the stirring member and discharges or draws in air that is discharged or drawn in through the air discharge and intake port.

Also, to achieve the stated object, the additive supply member of the present invention is an additive supply member that is used in a cell culture analyzer and that supplies an additive to a medium in a culture vessel, the member comprising an additive container and an air pressure supply unit. The additive container has an opening at the lower end portion and supplies an additive into the culture vessel. The air pressure supply unit has an air inlet for drawing in the air inside a culture incubator that houses the culture vessel, and applies air pressure into the additive container.

Furthermore, to achieve the stated object, the sensor unit of the present invention comprises a board, additive containers, and a seal. The board is provided with a plurality of openings that match up with the positions of a plurality of culture vessels to which additives have been supplied. The additive containers are disposed in each of the plurality of openings of the board, have an upper surface opening that opens upward, and supply the additives to the culture vessel. The seal is affixed so as to cover the upper surface of the board corresponding to the upper surface openings in the additive container in a removable state.

Furthermore, to achieve the stated object, the additive supply member of the present invention is an additive supply member for adding an additive to a medium in a culture vessel, the member comprising an additive container and an air pressure supply member. The additive container has an opening for adding the additive into the culture vessel. The air pressure supply member applies air pressure into the additive container. The additive container has a cylindrical shape with the opening at the bottom, and the outside diameter thereof decreases toward the lower end, and has a dropping adjustment surface that is provided on the outer peripheral edge of the opening and adjusts the amount in which the additive is discharged from the opening.

To achieve the stated object, the sensor unit of the present invention is a sensor unit having a sensor for measuring the components of a culture medium in a culture vessel, comprising a sensor and a board. The sensor has a main body portion, a measurement unit that is disposed on the main body portion and measures the components of the medium, and a connection terminal portion that is electrically connected to the measurement unit. The board has a connecting portion that is connected to the connection terminal portion of the sensor, and a wiring pattern that is connected to the connecting portion. The sensor has a bent part in which a part of the main body portion is bent so that the measurement portion of the sensor projects downward in a state in which the connection terminal portion and the connecting portion of the board are connected.

Technical Effects

The cell culture analyzer of the present invention does not require a stirring rod or plunger to be provided for each culture vessel, and therefore can be more compact.

Also, with the additive supply member according to the present invention, the air in the culture incubator that houses the culture vessel, that is, the controlled air, is utilized as the air pressure going to the additive vessel, which prevents contamination of the cell culture in the culture vessel.

Furthermore, with the cell culture analyzer of the present invention, since the opening in the board portion corresponding to the upper surface of the unused culture vessel is covered with the seal, no air will leak out through the additive containers located in this opening, and the proper air pressure can be applied to the required additive containers, allowing the proper additives to be supplied.

Also, since cell culture analysis can be executed by the simple operation of removing the seal from the board portion corresponding to the upper surface of the culture vessels to be used, work efficiency can be improved.

Furthermore, with the additive supply member of the present invention, when air pressure is applied to an additive container, the additive held in the additive container moves to the lower surface opening side, resulting in a clumped state in which the additive is held by the surface tension of the dropping adjustment surface provided on the outer peripheral edge of the opening. After this, the additive is dropped into the lower culture vessel as droplets that have overcome the holding force produced by surface tension.

Also, when this dropping occurs, the next additive also ends up in the above-mentioned clumped state, and before long is dropped as droplets into the culture vessel below.

That is, in the present invention, since the additive is supplied intermittently into the culture vessel, the cells are less likely to be subjected to sudden stress by the additive, and as a result, the cell culture analysis is carried out properly.

With the sensor unit of the present invention, there is no need for a configuration in which a lead wire is directly connected to the sensor, which affords a more compact size.

BRIEF DESCRIPTION OF TUE. DRAWINGS

FIG. 6 is a diagram showing the state when the adapter unit constituting the analysis unit in FIG. 5 is attached between a top unit and a bottom unit;

FIGS. 11A to 11C are diagrams showing the routing of pipes formed in a piping board portion;

Figure 1:
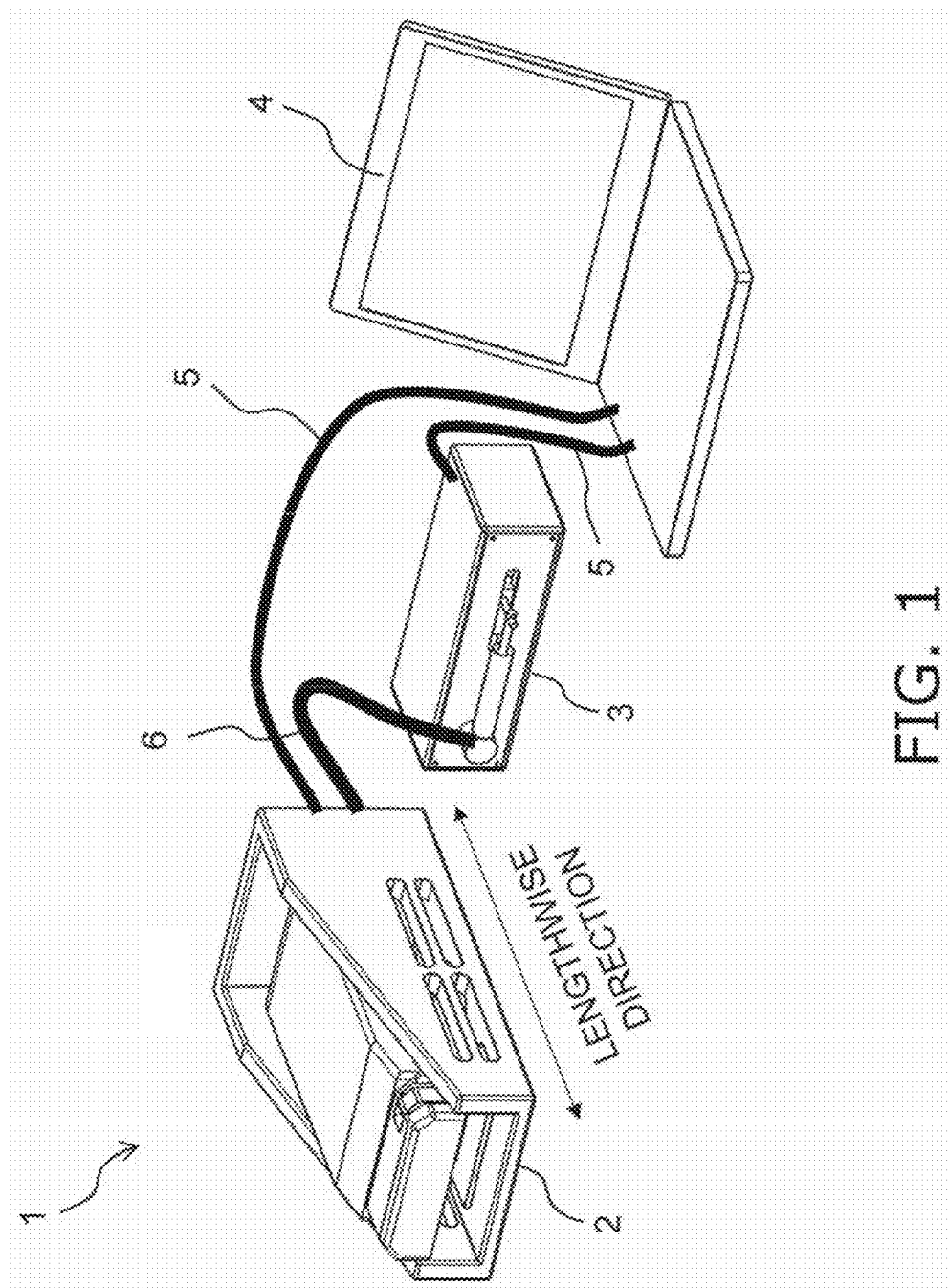
FIG. 1 is a diagram showing the configuration of the cell culture analyzer according to an embodiment of the present invention.
Figure 16B:
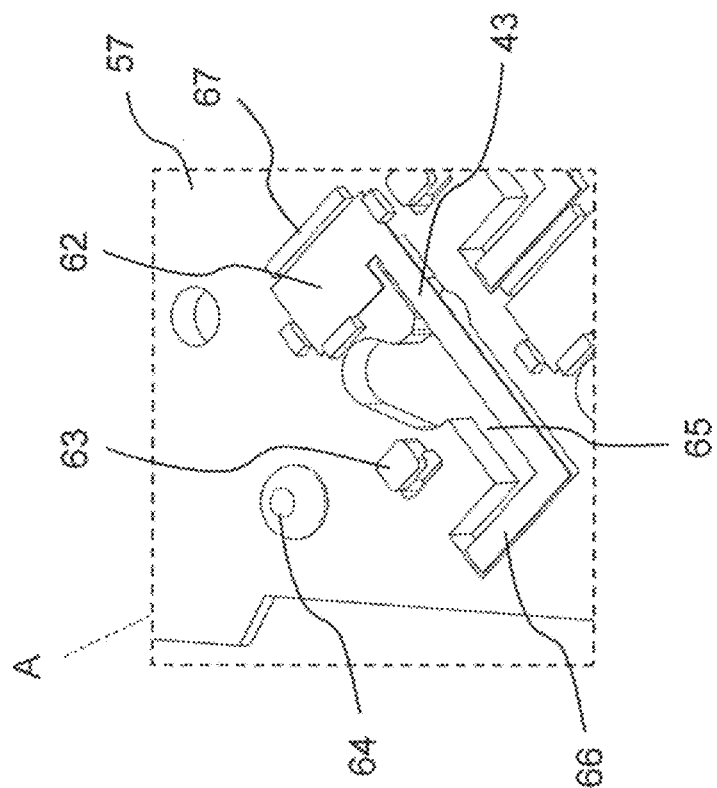
Figure 16A:
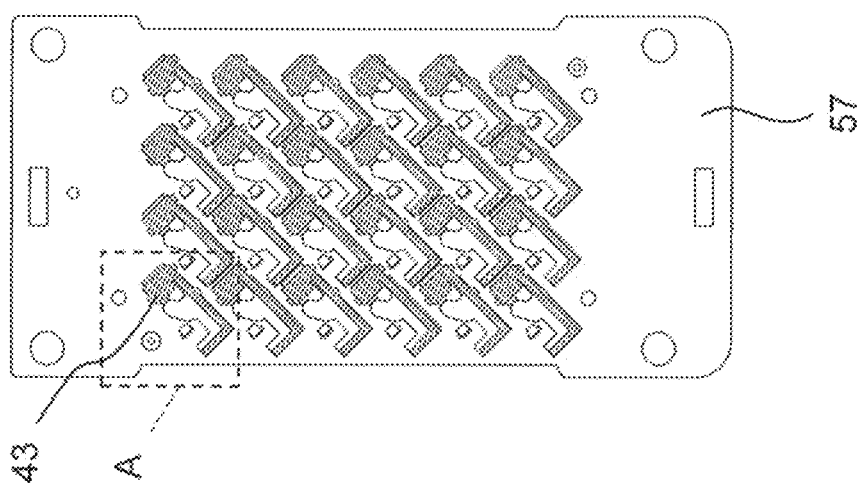
Figure 17B:
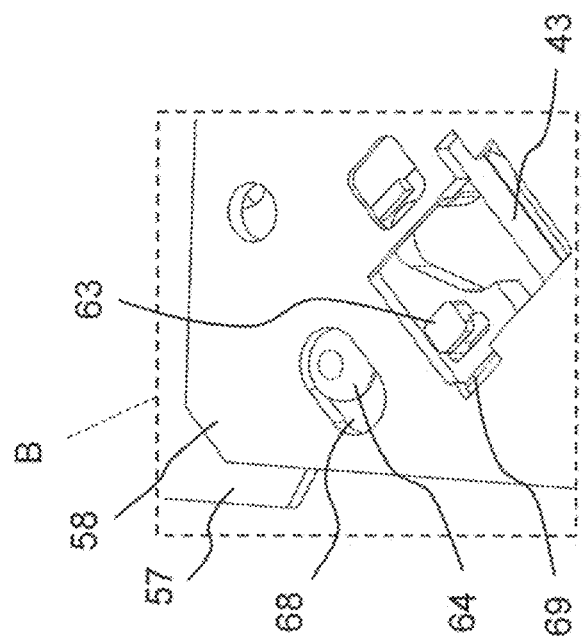
Figure 17A:
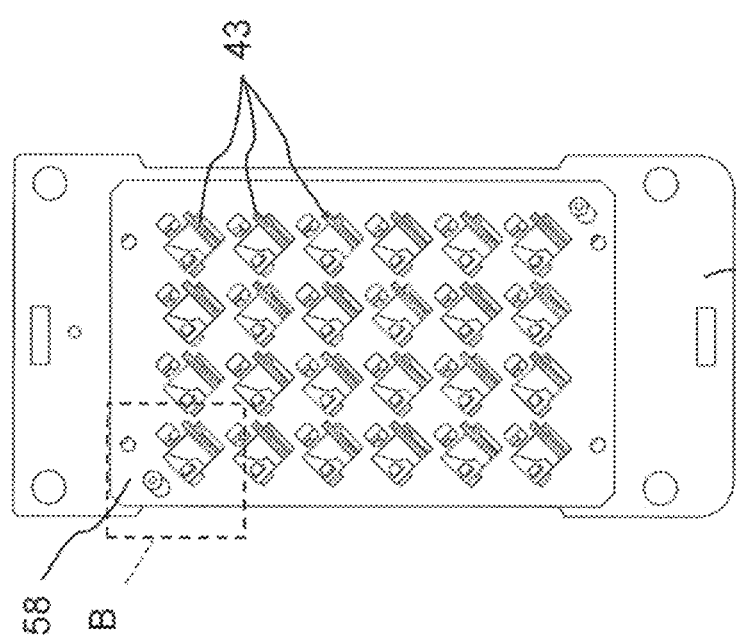
Figure 18B:
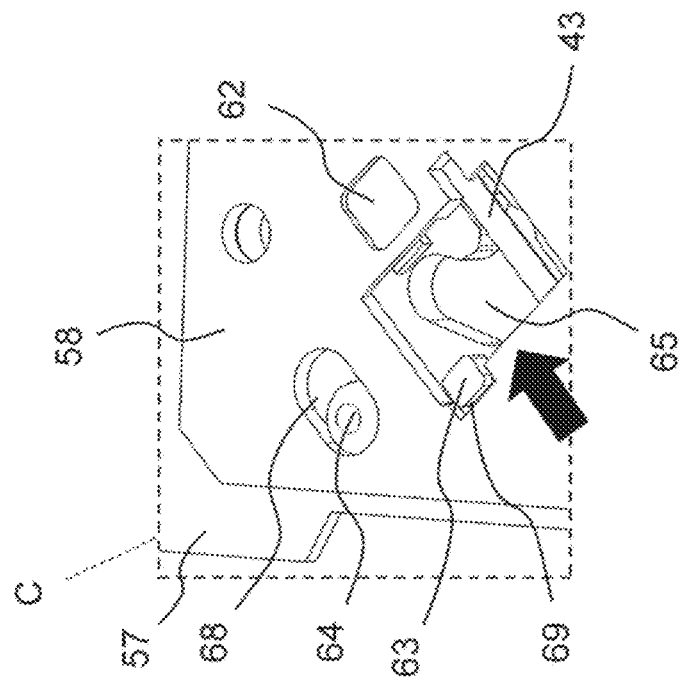
Figure 18A:
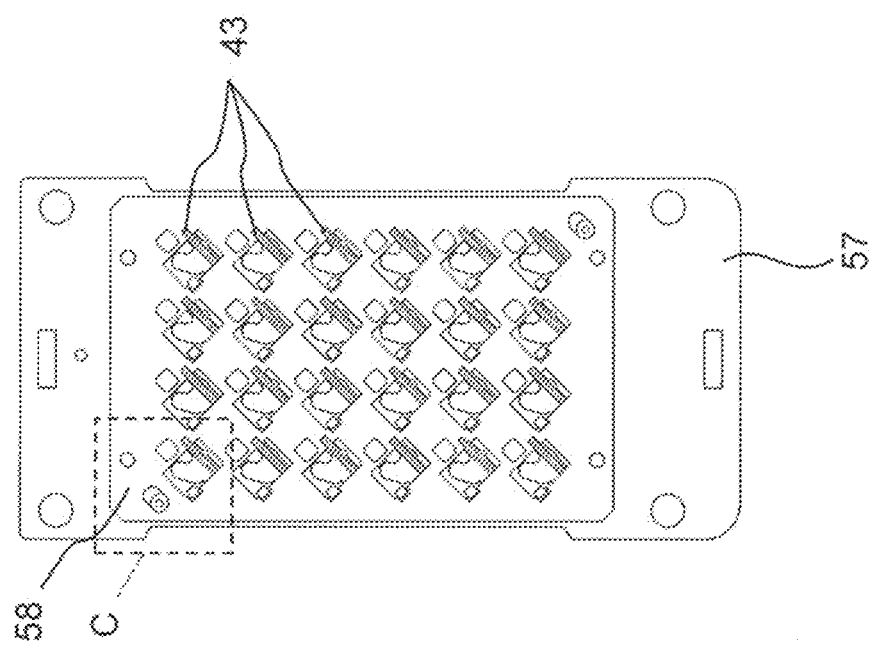
Figure 20C:
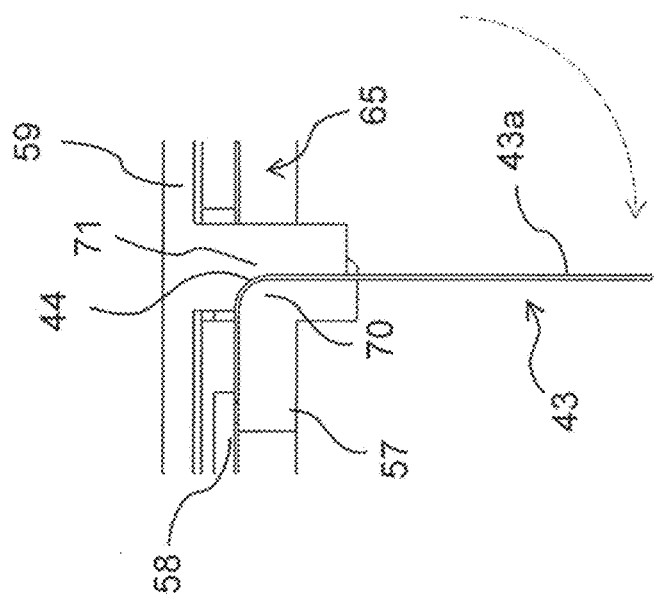
Figure 20B:
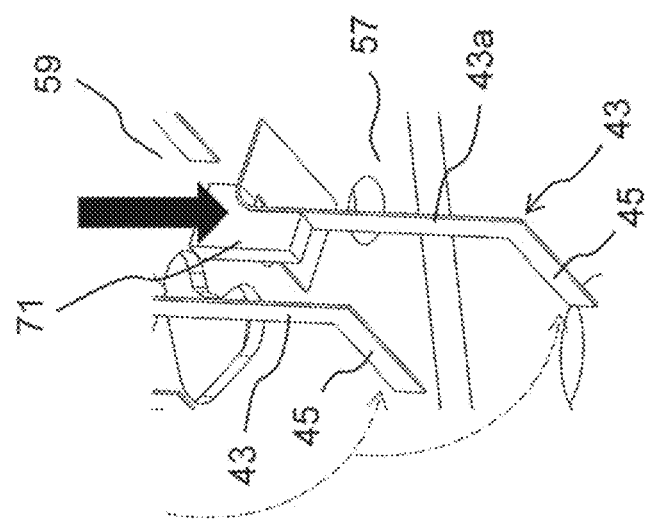
Figure 20A:
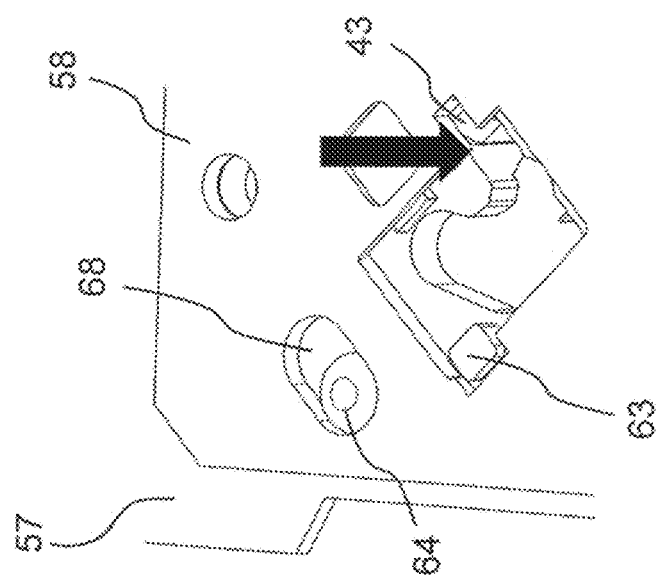
Figure 21B:
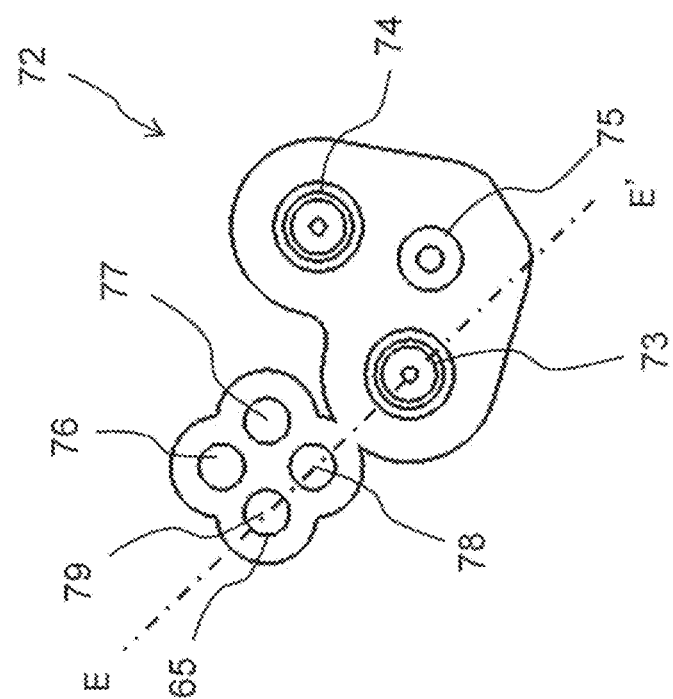
Figure 21A:
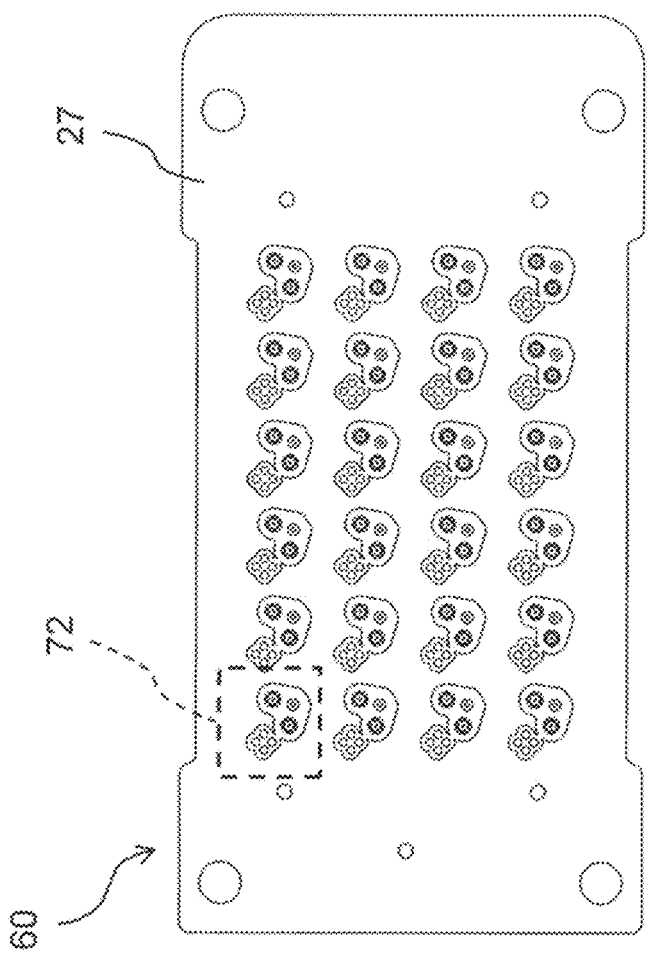
Figure 22:
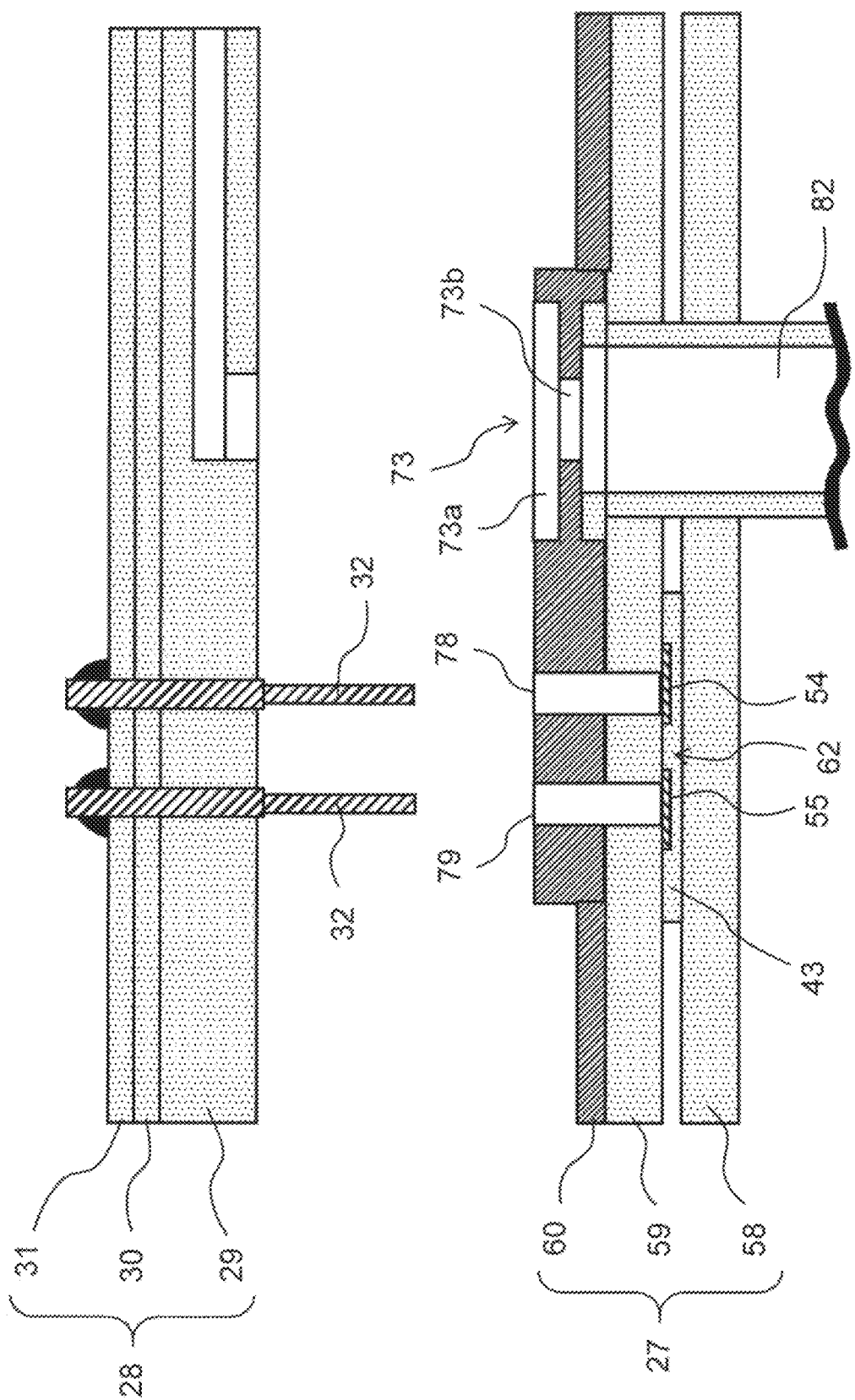
Figure 23:
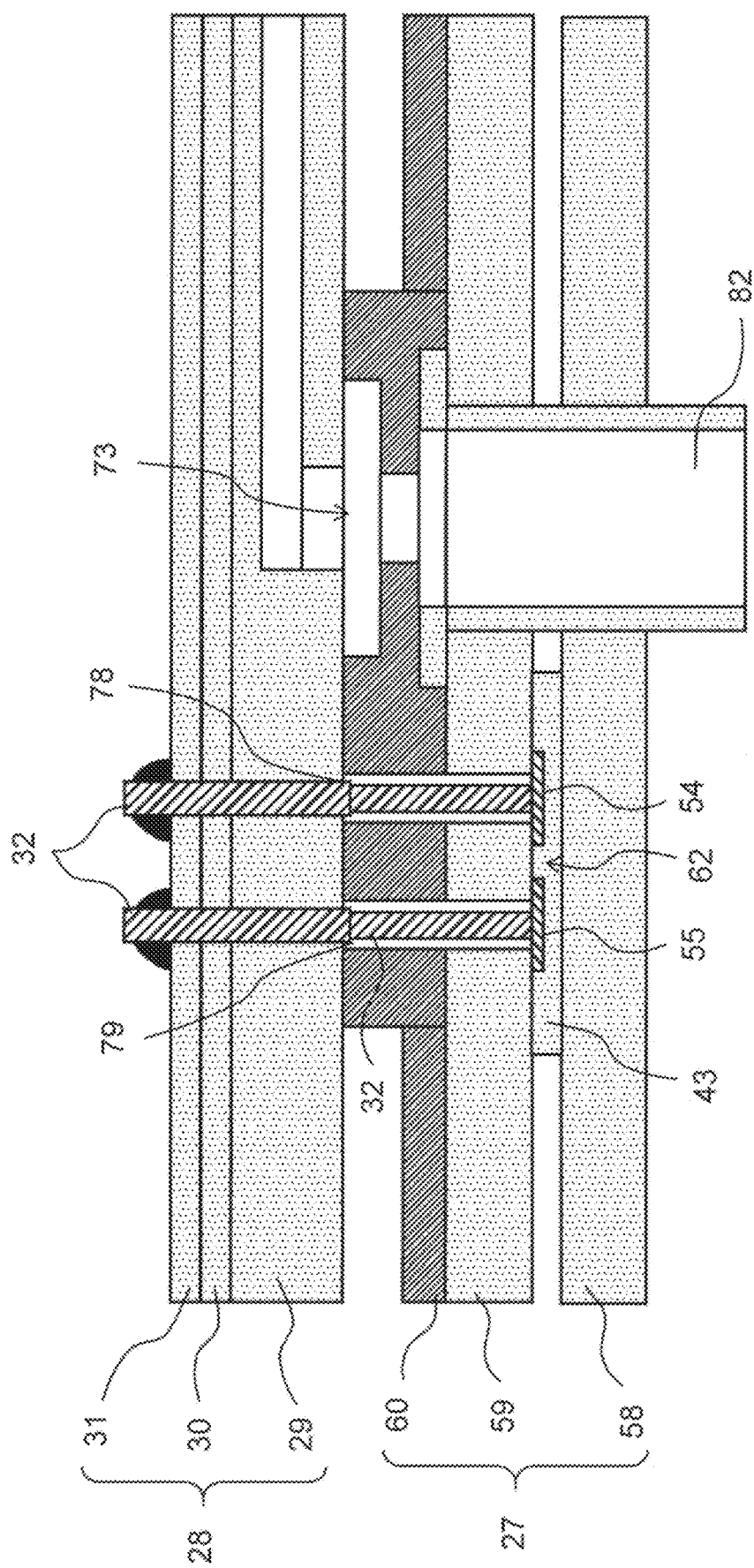
Figure 24:
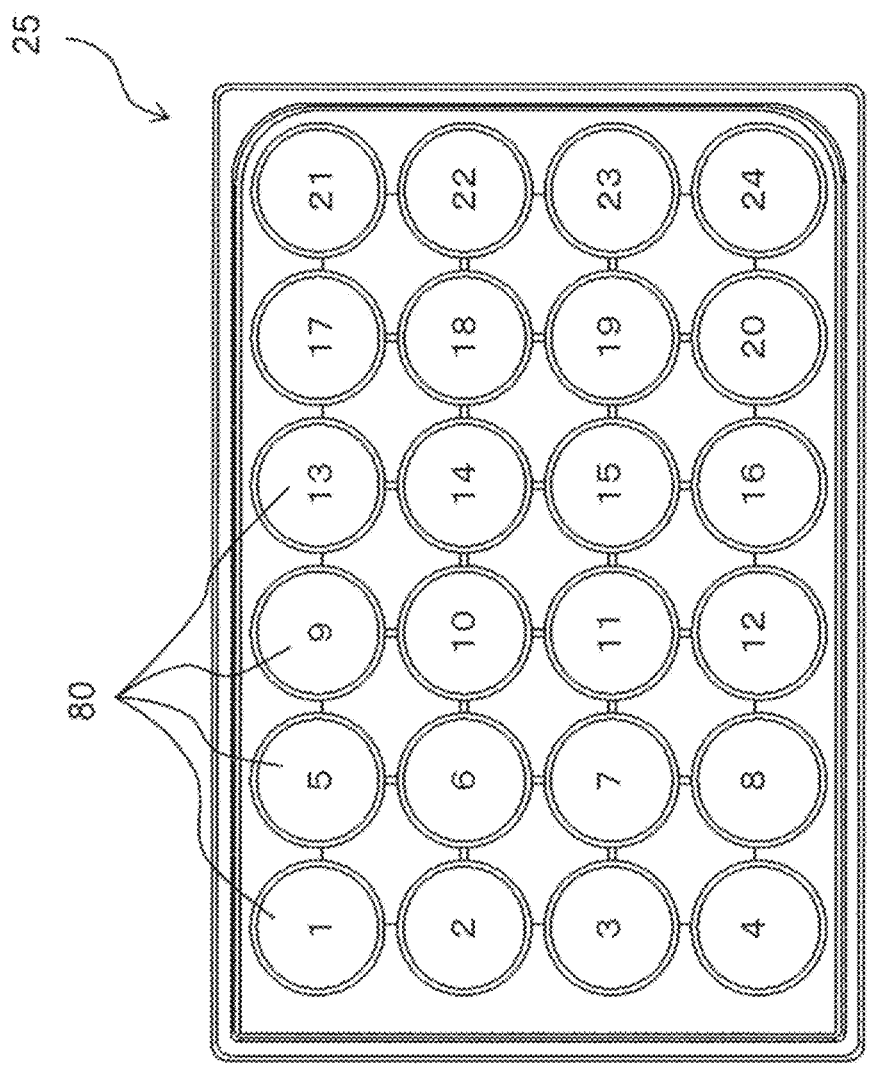
Figure 25B:
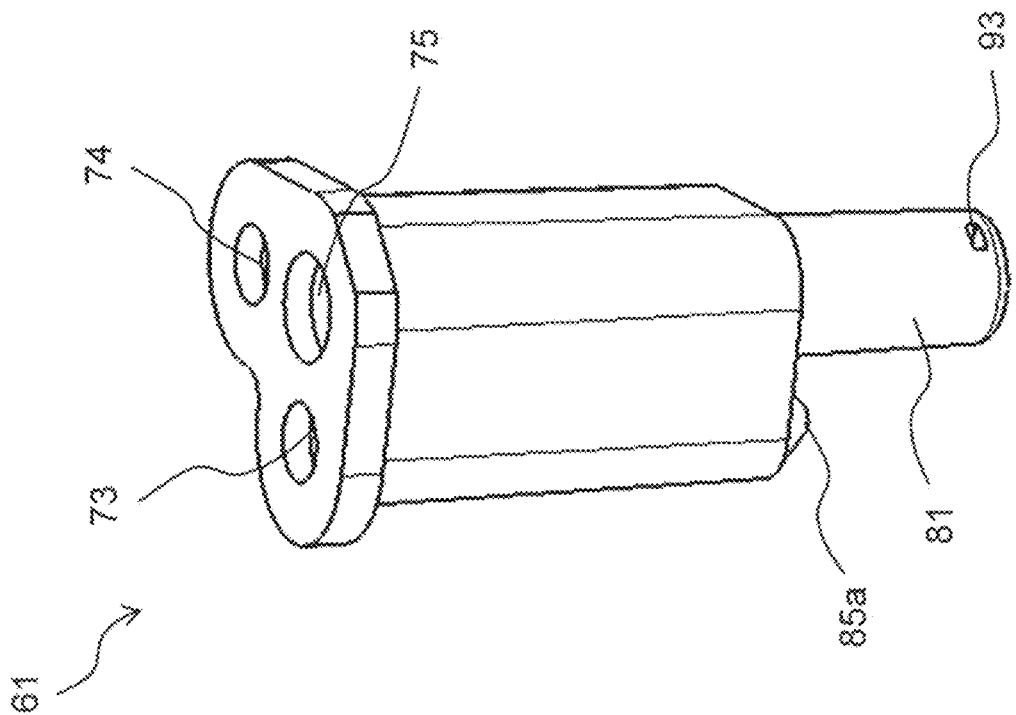
Figure 25A:
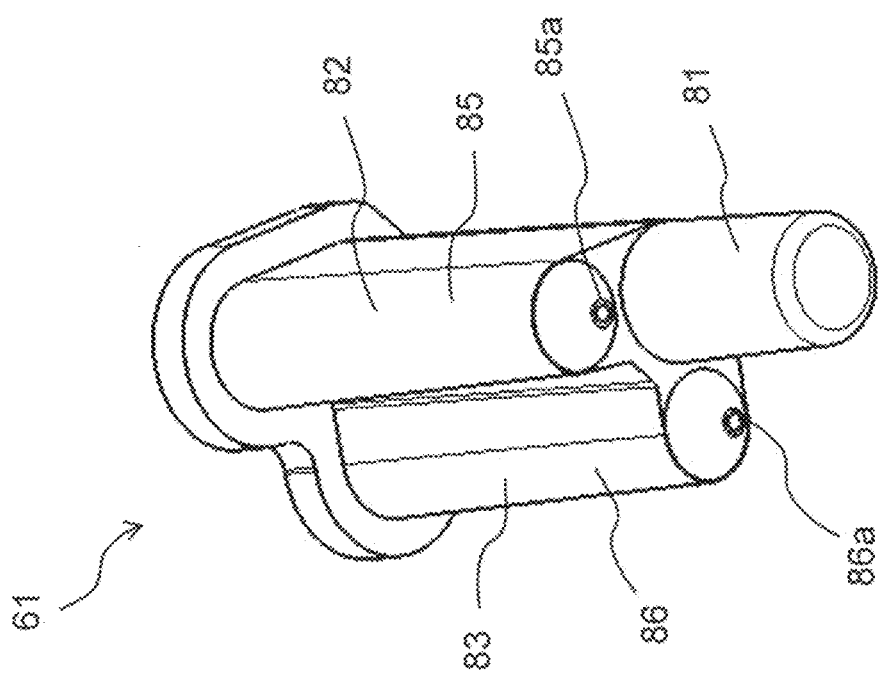
Figure 26B:
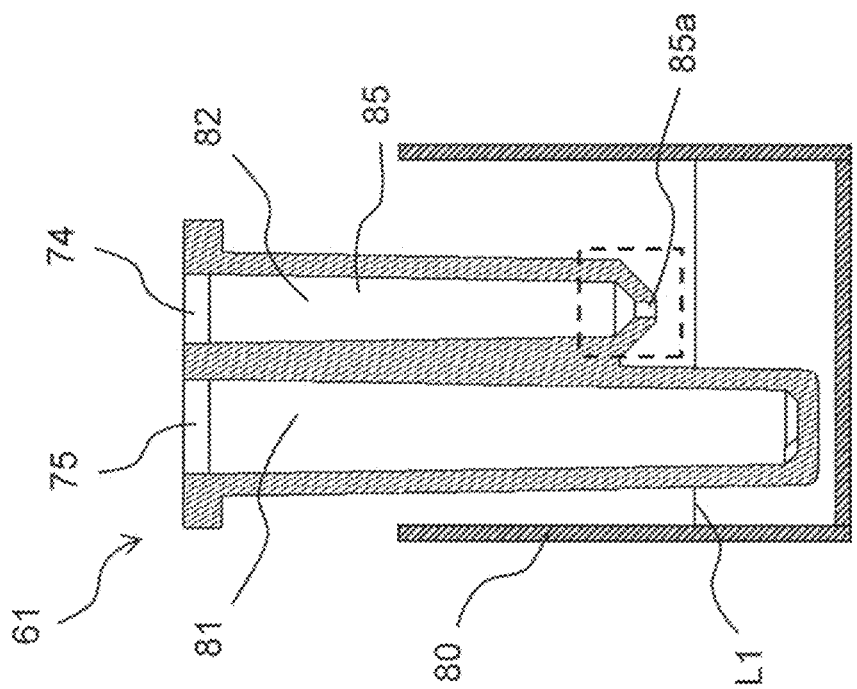
Figure 26A:
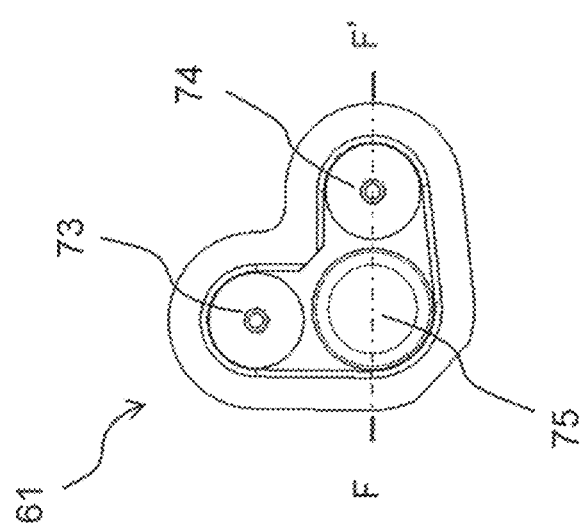
Figure 27:
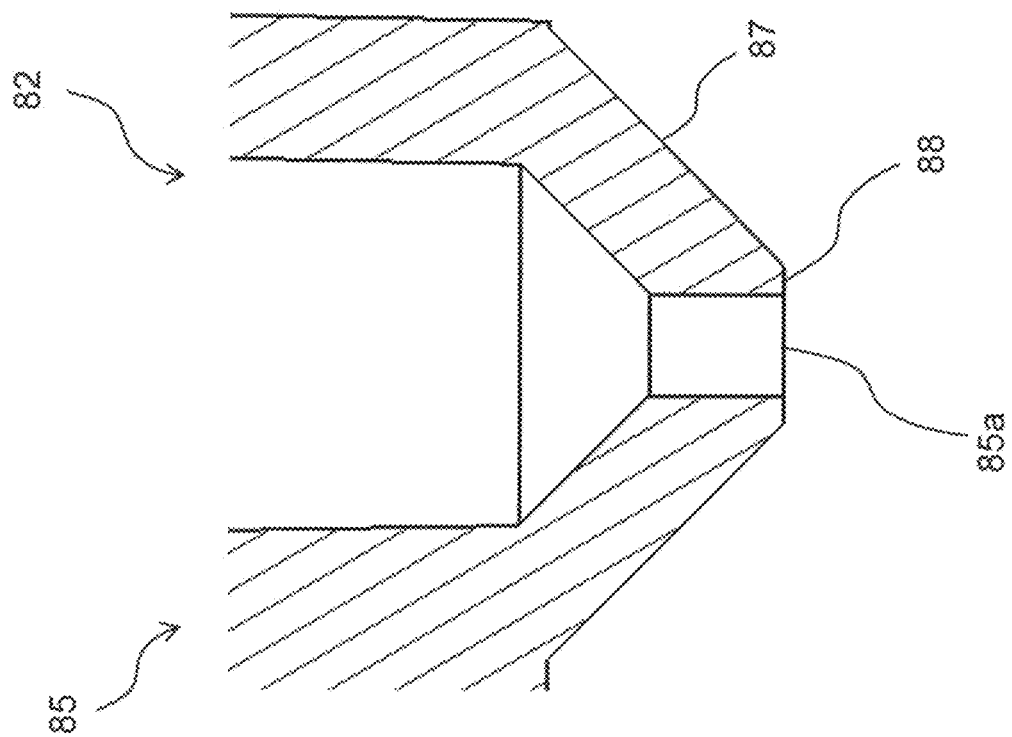
Figure 28C:
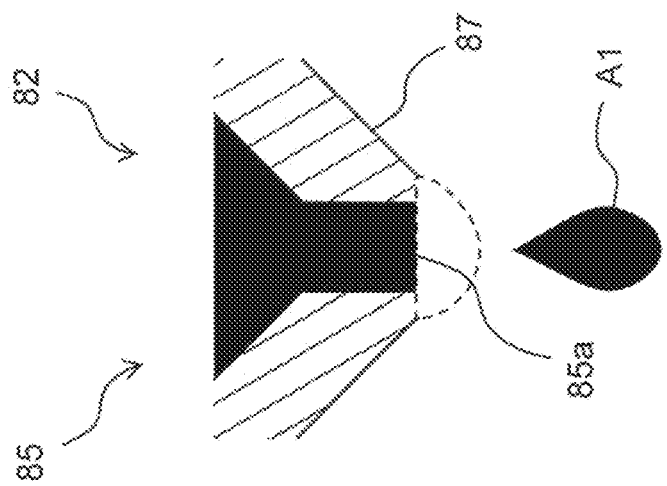
Figure 28B:
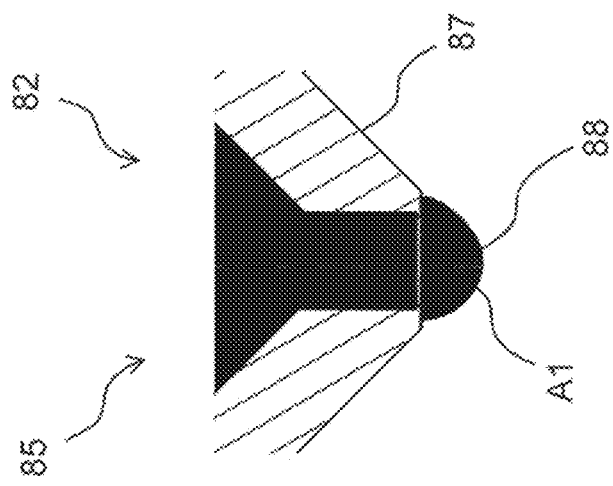
Figure 28A:
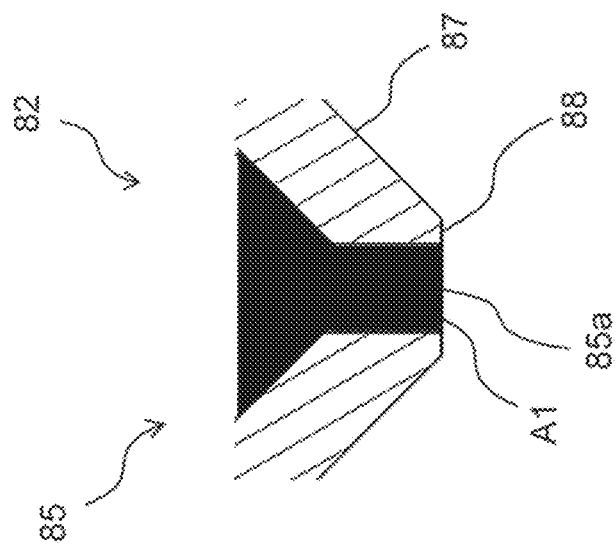
Figure 29:
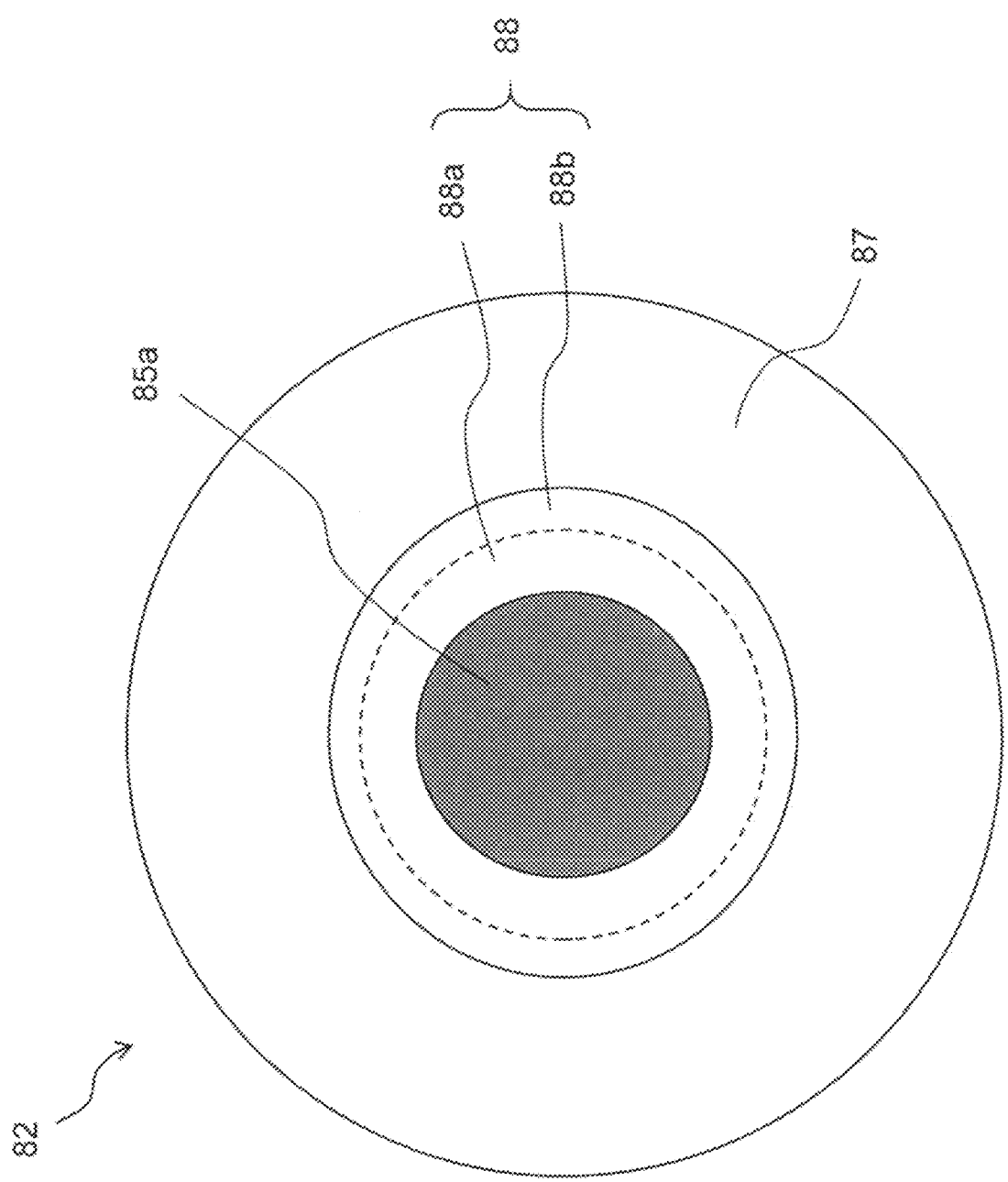
Figures 30A, 30B:
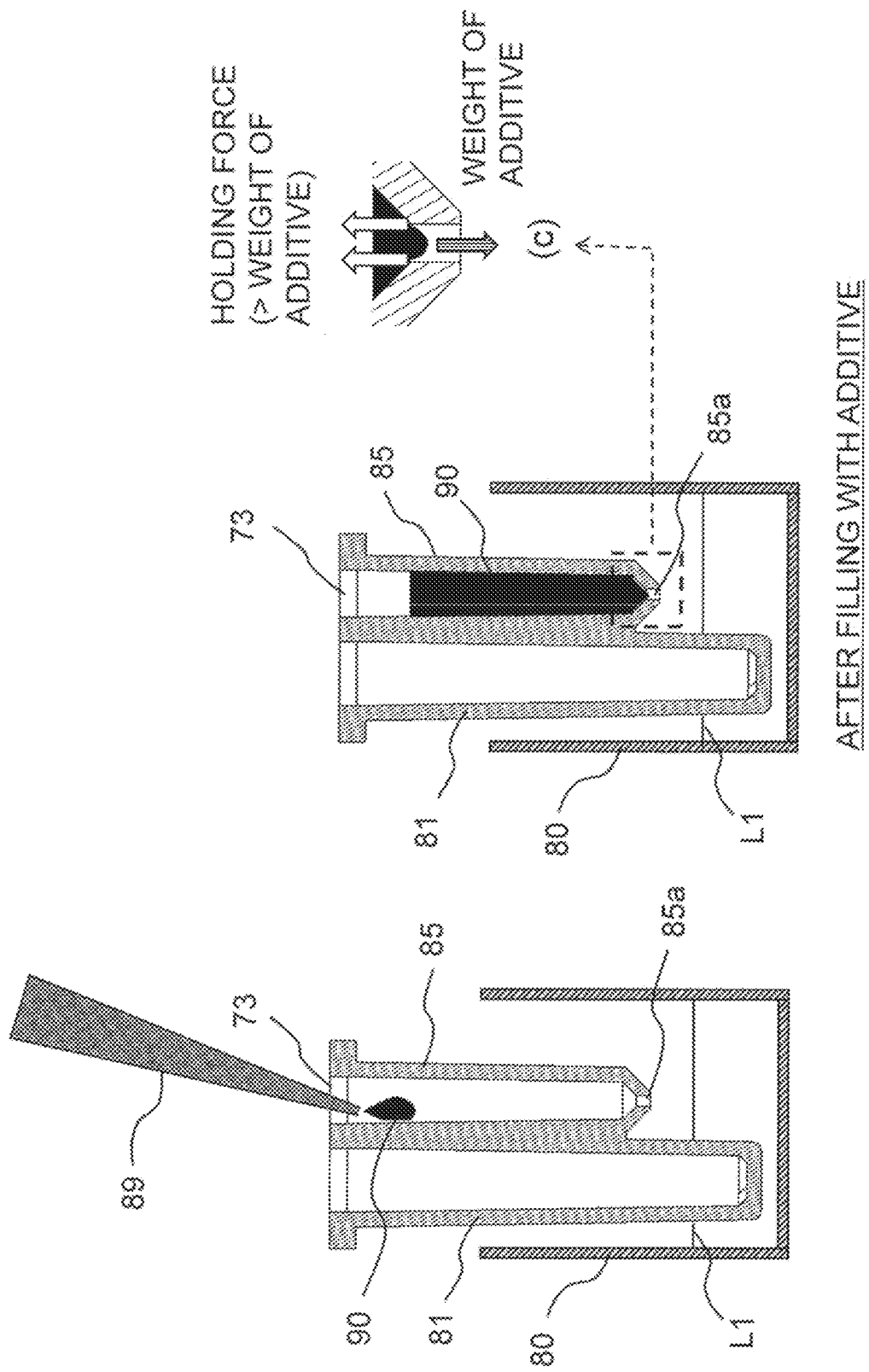
Figure 31B:
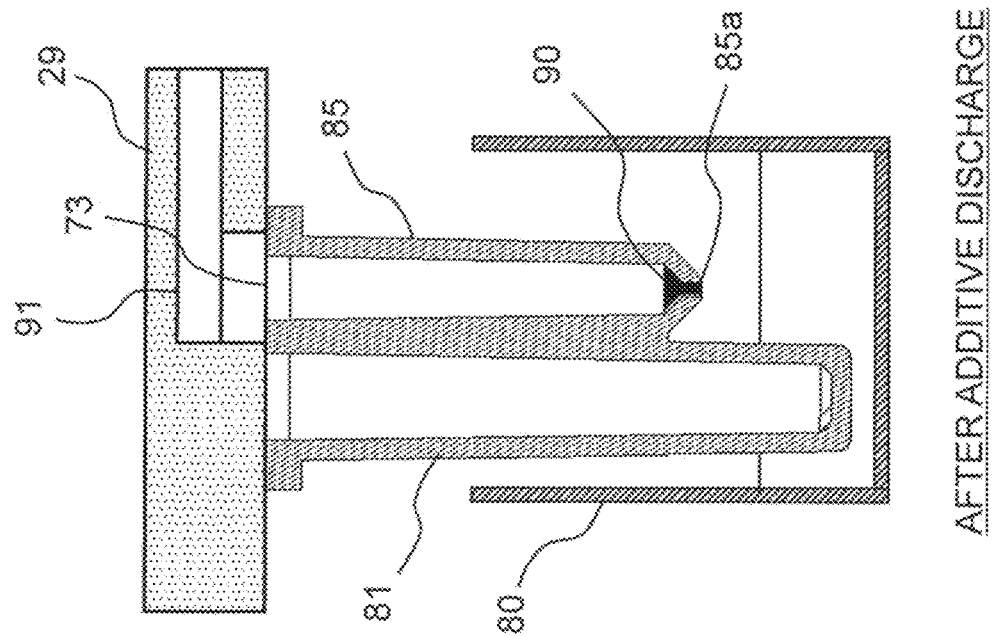
Figure 31A:
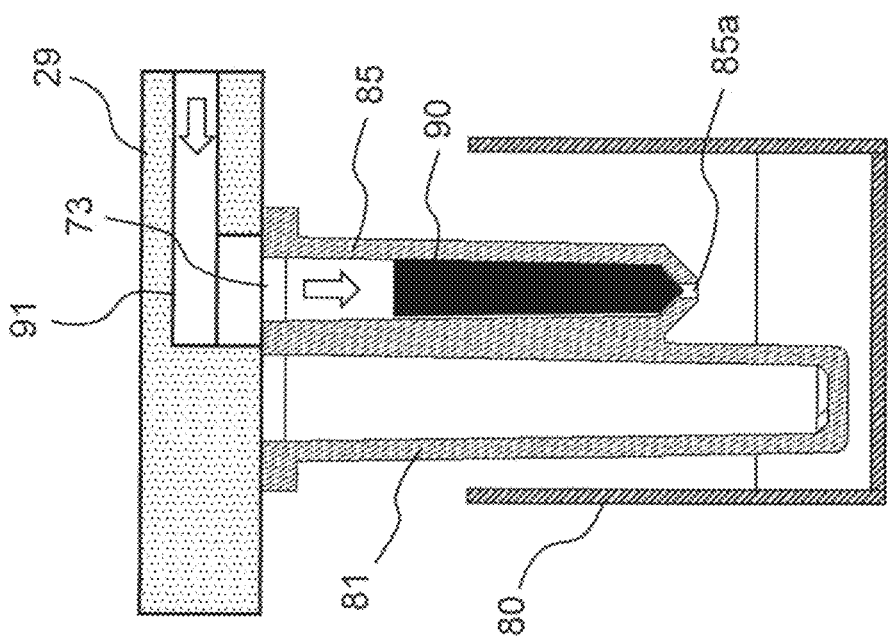
Figure 32A:
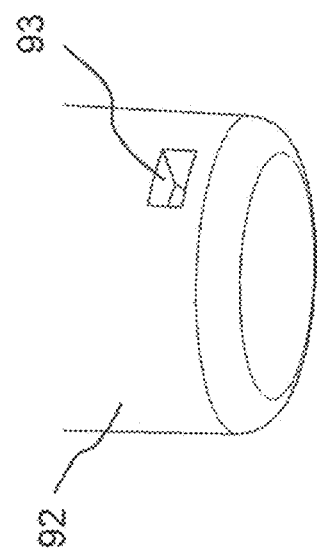
Figure 32B:
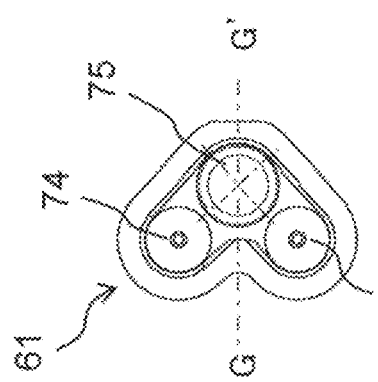
Figure 32C:
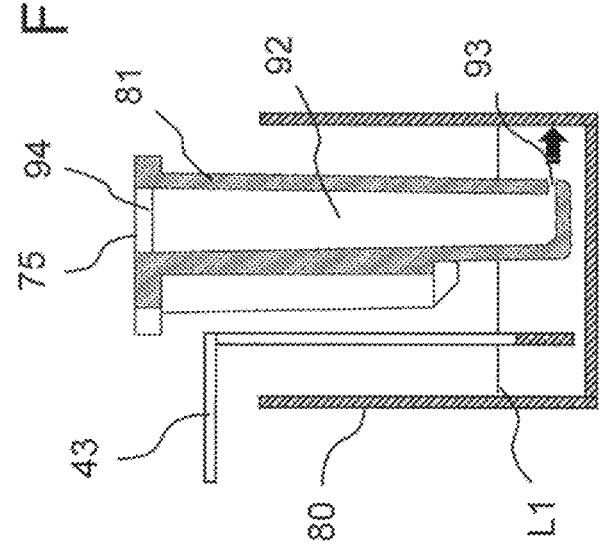
Figure 33C:
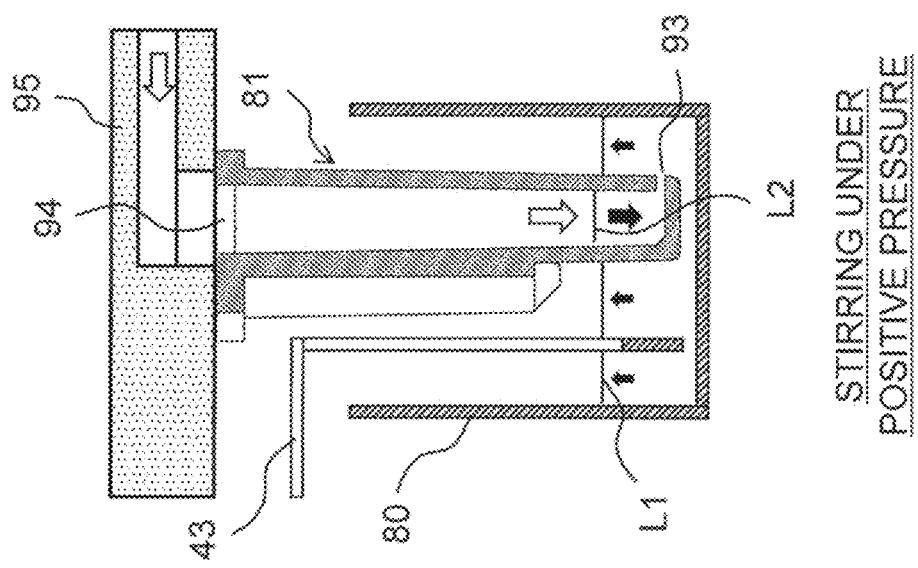
Figure 33B:
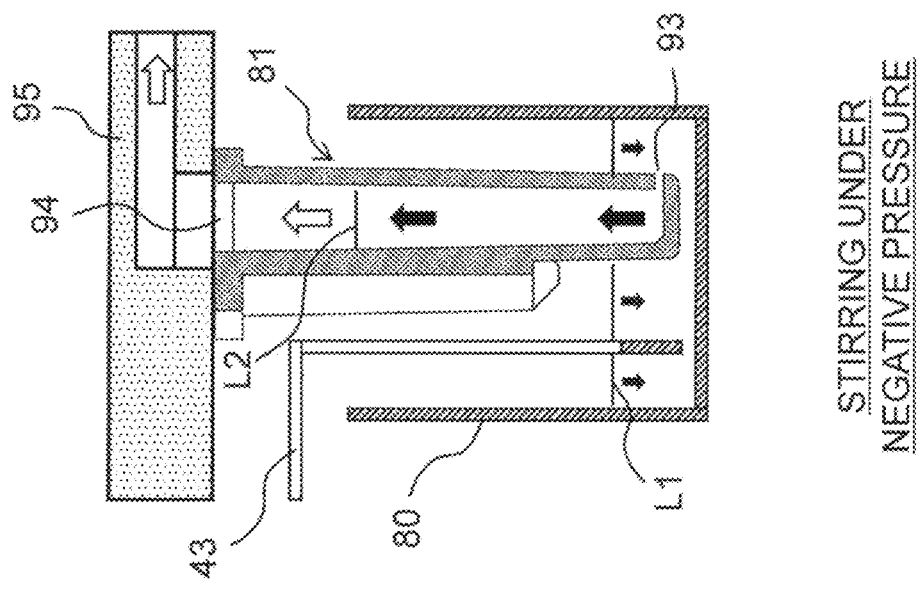
Figure 33A:
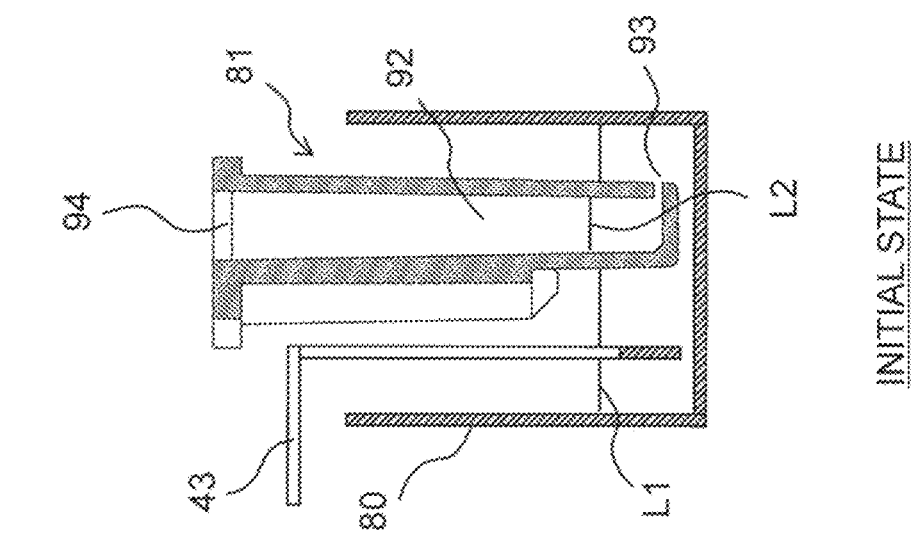
Figure 34:
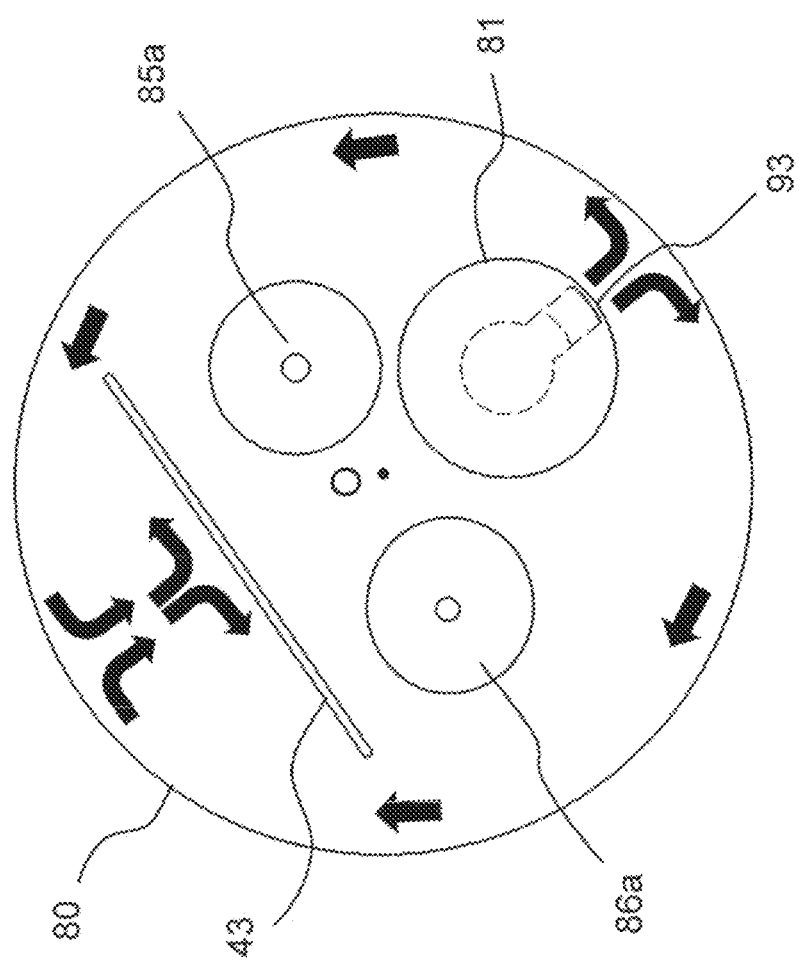
Figure 35B:
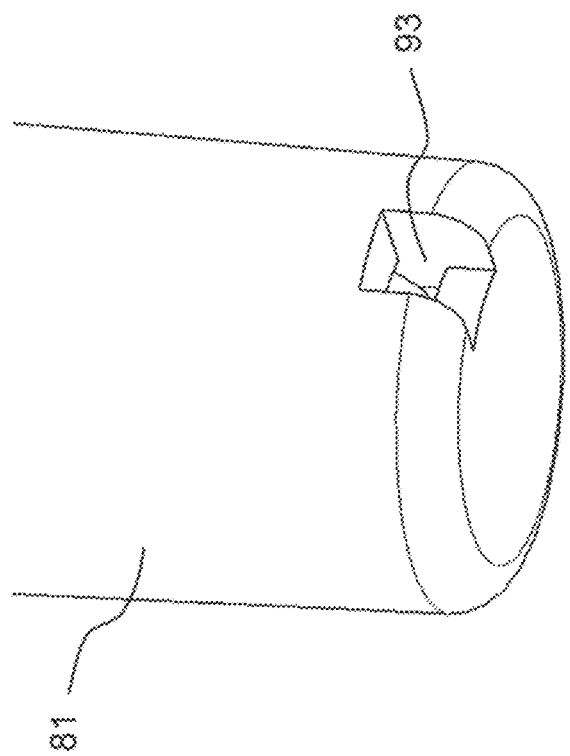
Figure 35A:
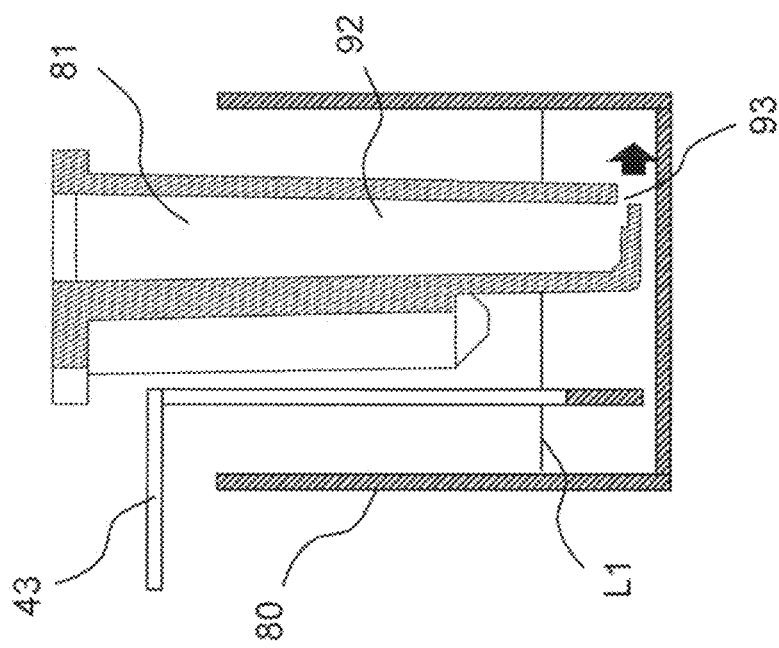
Figure 37:
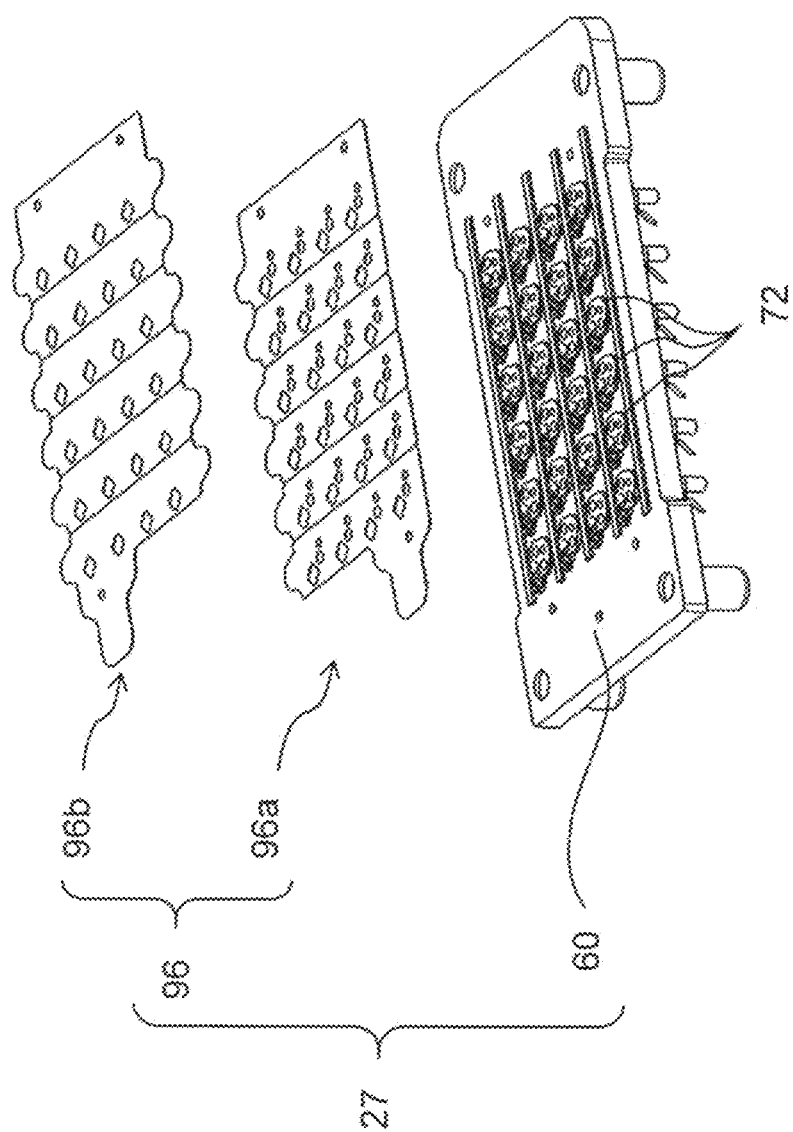
Figure 38B:
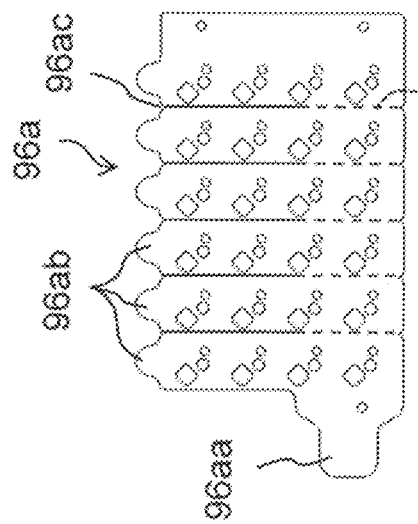
Figure 38D:
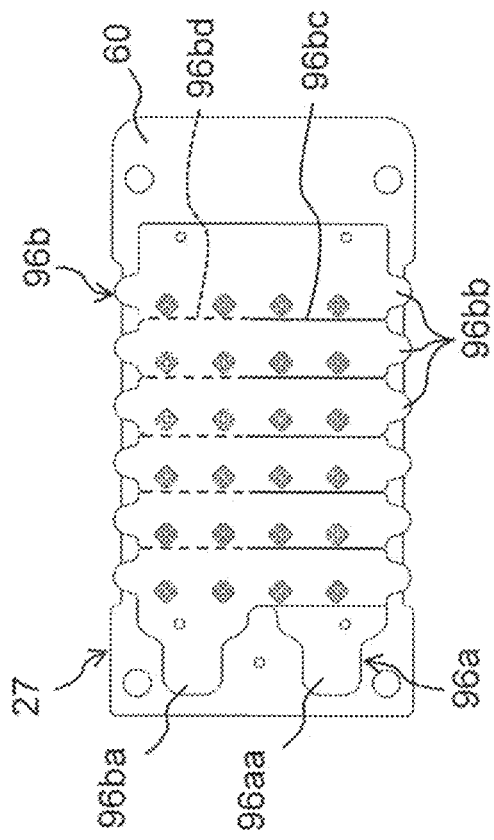
Figure 38A:
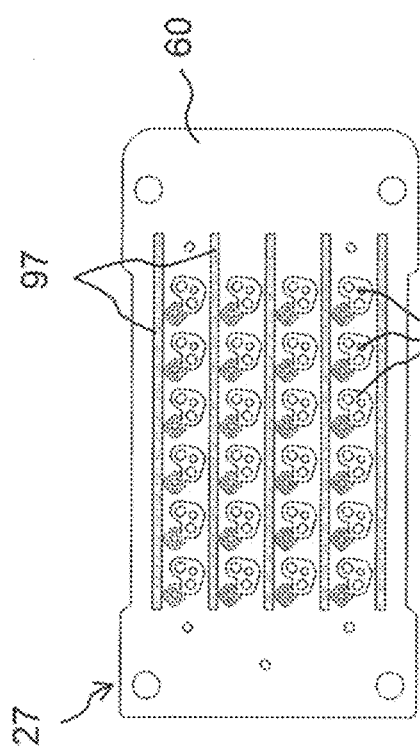
Figure 38C:
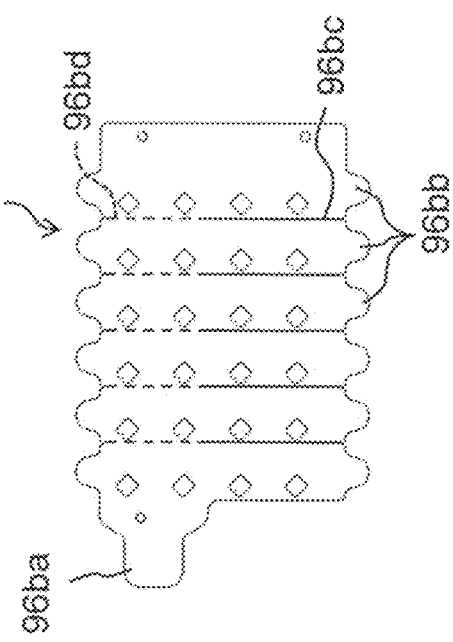
Figure 40:
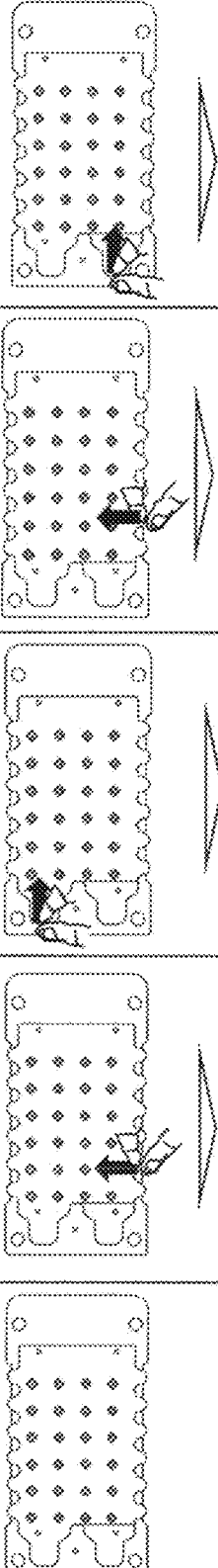
Figure 41B:
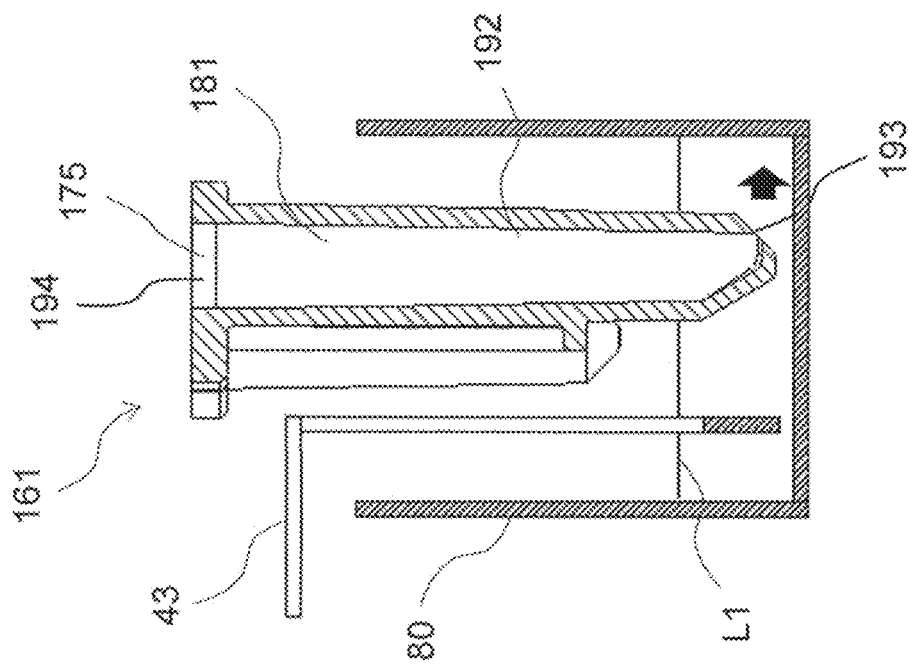
Figure 41A:
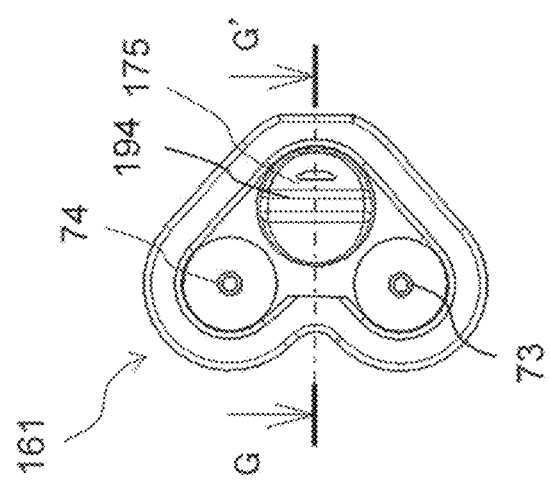
Figure 42B:
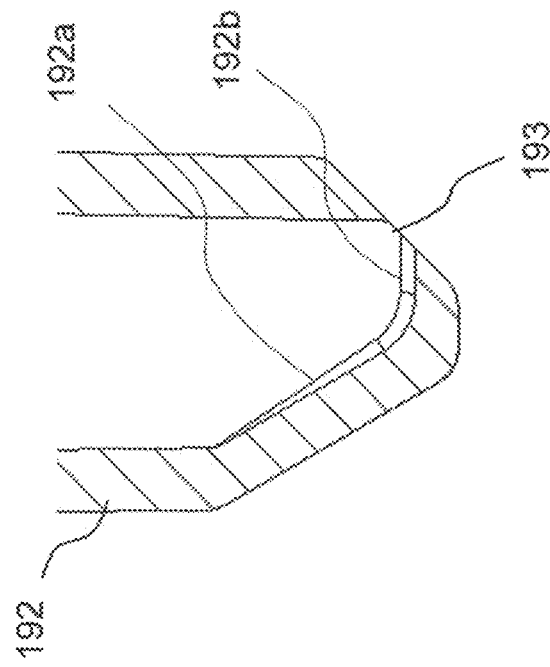
Figure 42A:
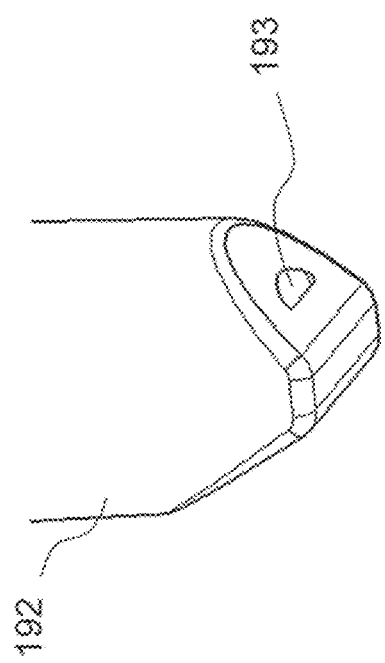
Figure 43B:
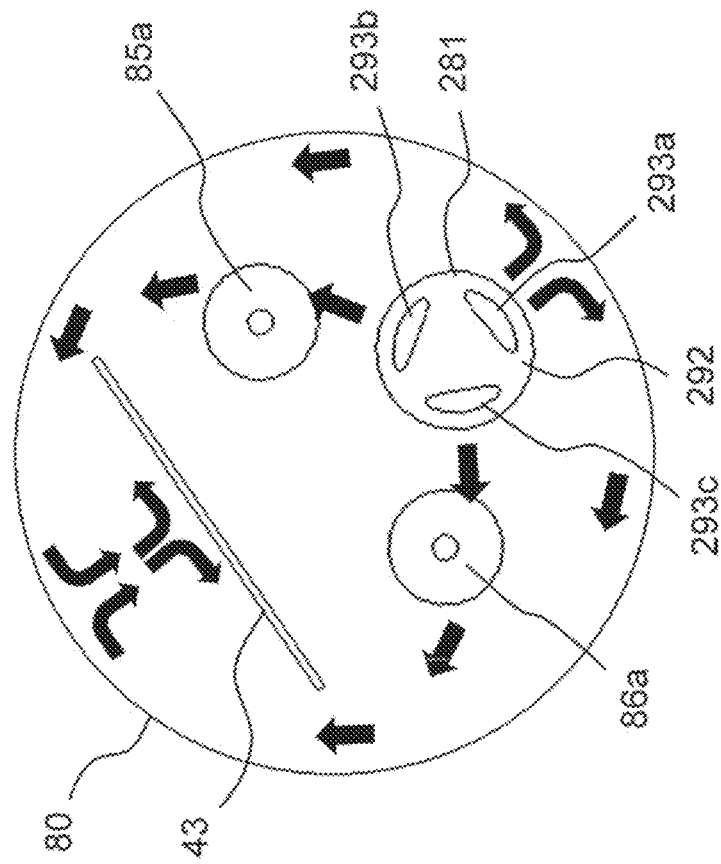
Figure 43A:
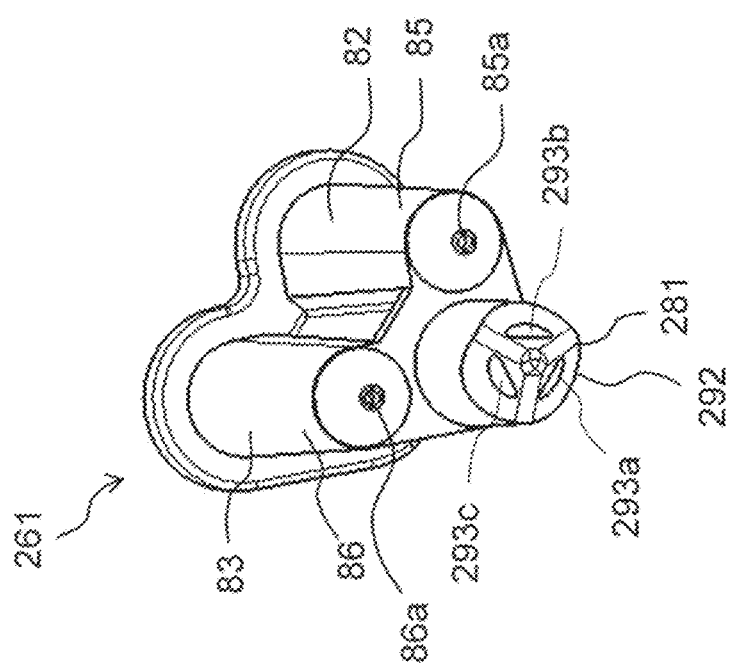
Figure 44B:
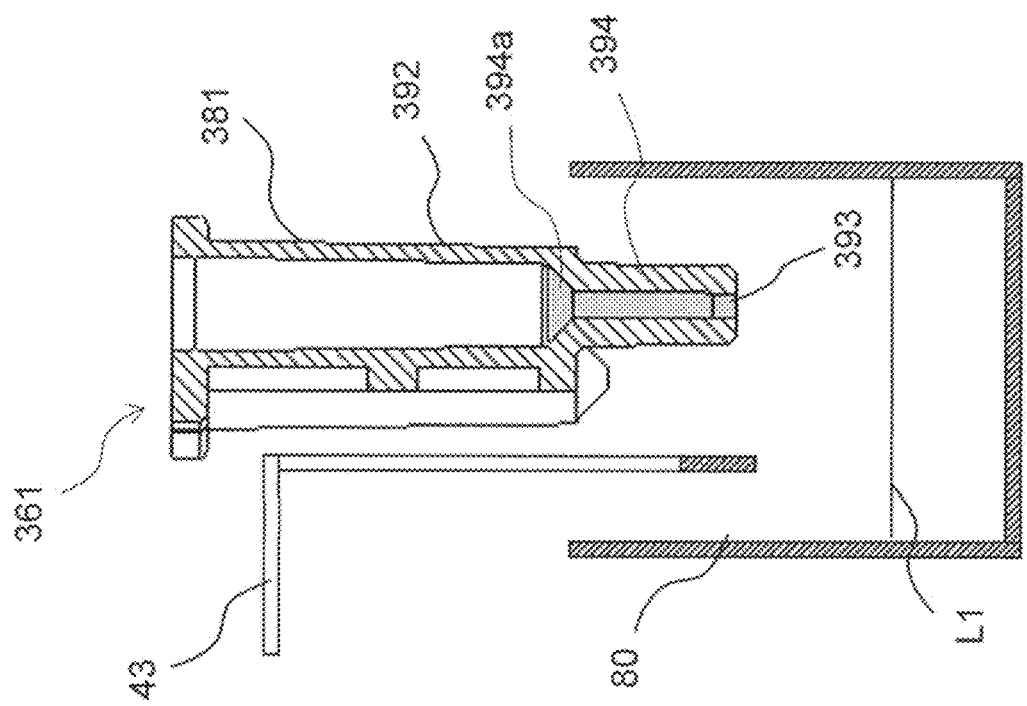
Figure 44A:
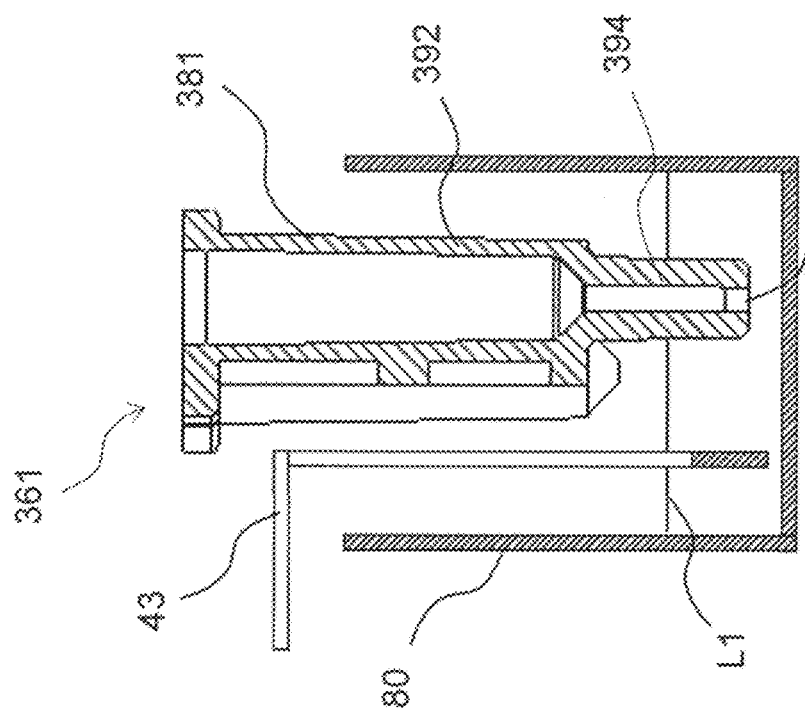
Figure 45B:
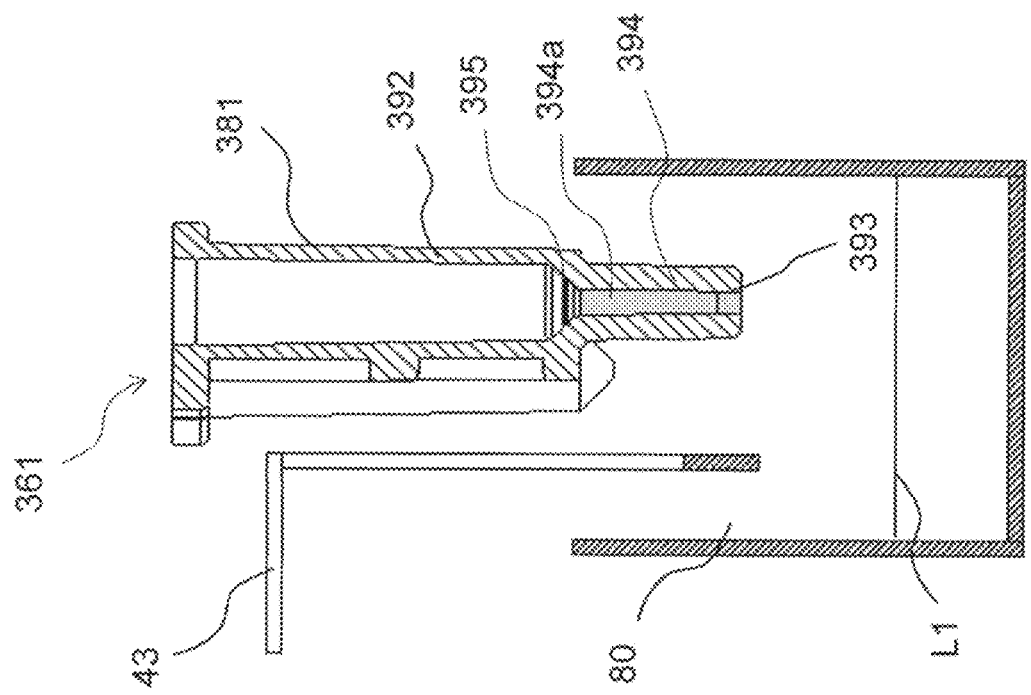
Figure 45A:
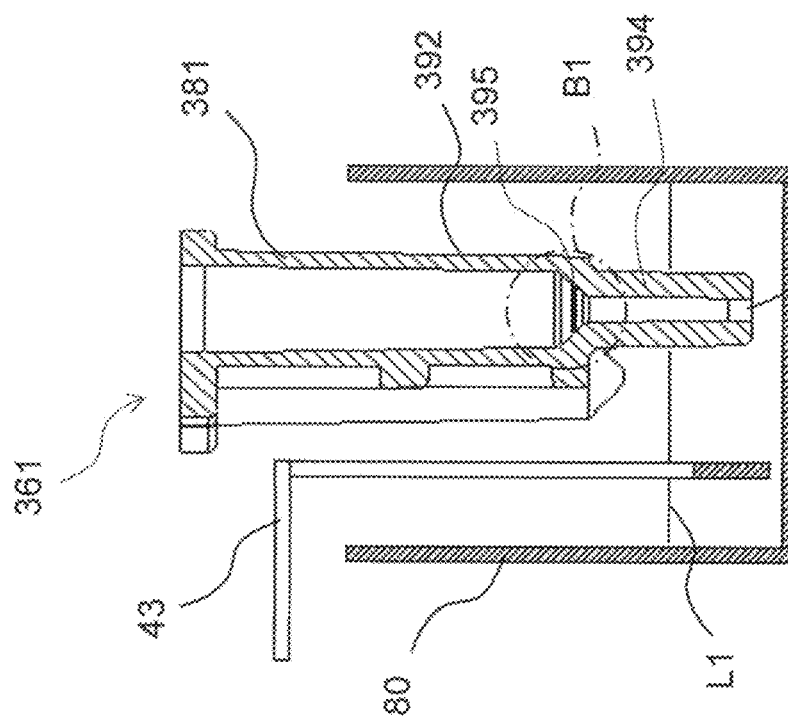
Figure 46:
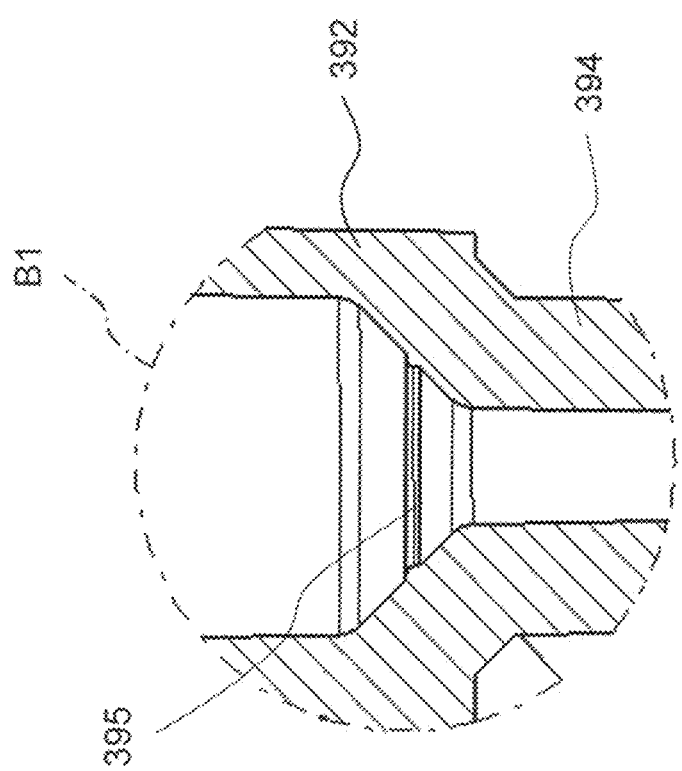
Figure 47B:
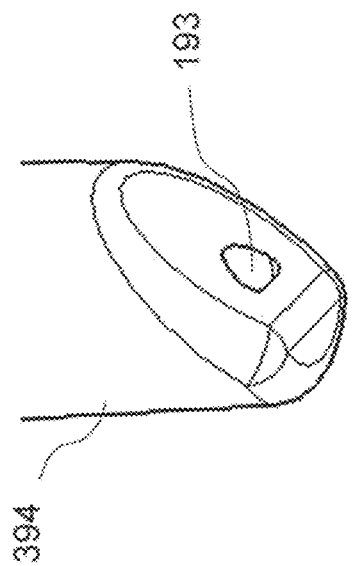
Figure 47A:
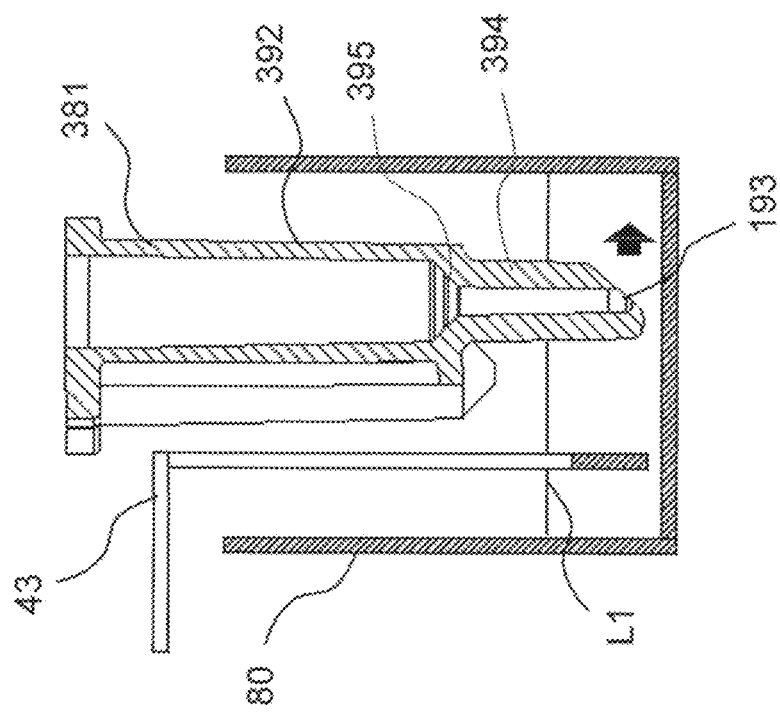

FIGS. 1.5A to 15C are diagrams illustrating a method for fixing and holding a sensor;

FIG. 16A is a diagram showing a state in which a plurality of sensors have been placed on a bottom plate, and FIG. 16B is a detail view of the A portion in FIG. 16A;

FIG. 17A is a diagram showing the state when a middle plate has been put over a plurality of sensors placed on the bottom plate, while FIG. 17B is a detail view of the B portion in FIG. 17A;

FIG. 18A is a diagram showing a state in which the middle plate is slid in a direction substantially parallel to the diagonal line of the bottom plate with respect to the bottom plate, and FIG. 18B is a detail view of the C portion in FIG. 18A;

FIG. 19A is a top view of the state when the middle plate has been fixed to the bottom plate, and FIG. 19B is a cross-sectional view along the A-A' line;

FIG. 20A is a diagram of a sensor positioned and fixed while sandwiched between the bottom plate and the middle plate in a state in which the upper portion of a vertical side has been bent further downward from a bent portion, FIG. 20B is an oblique view of the state when the top plate is disposed on the middle plate as seen from under the bottom plate, and FIG. 20C is a cross-sectional view of the cross-sectional structure thereof;

FIG. 21A is a top view of a gasket sheet, and FIG. 21B is a detail view of a port input/output portion of the gasket sheet in FIG. 21A;

FIG. 22 is a cross-sectional view along the E-E' line of the port input/output portion shown in FIG. 21B;

FIG. 23 is a cross-sectional view showing the state when a board unit is incorporated into a sensor unit on the upper surface side;

FIG. 24 is a top view of a well plate;

FIG. 25A is an oblique view of a port for adding additives to the wells, as seen from below, and FIG. 25B is an oblique view of the port as seen from above;

FIG. 26A is a top view of the port, and FIG. 26B is a cross-sectional view along the F-F' line in FIG. 26A;

FIG. 27 is a detail cross-sectional view showing the configuration in the vicinity of the discharge port of an additive A;

FIGS. 28A to 28C are cross-sectional views showing the additive as it is dropped from the lower end portion of an additive A container of an additive addition portion A;

FIG. 29 is a plan view of the additive A discharge port side of the additive addition portion A (additive A container);

FIG. 30A is a diagram of when an additive is loaded into the additive A container as an initial step, FIG. 30B is a diagram showing the state after the additive has been loaded, and FIG. 30*c* is a detail view of the additive A discharge port when the additive is loaded;

FIG. 31A is a diagram showing the state when a piping board portion has been linked from above after loading the additive, and FIG. 31B is a diagram showing the state when an additive has been added into a well;

FIG. 32A is a top view of a port including a stirring member, FIG. 32B is a cross-sectional view along the G-G' line, and FIG. 32C is a detail oblique view of a stirring member discharge and intake port provided at the lower end portion of the stirring vessel of the stirring member;

FIG. 33A is a diagram showing the initial state of the stirring member, FIG. 33B is a diagram showing the state when an air discharge and intake unit is linked to the stirring member, and FIG. 33C is a diagram showing the state when the air discharge and intake unit acts in the direction of discharging air;

FIG. 34 is a plan view showing the state when the medium discharged from the stirring vessel is stirred along the inner peripheral surface of the culture vessel (well);

FIG. 35A is a diagram showing the configuration of the stirring member, including a liquid discharge and intake port in which no undercut is required, and FIG. 35B is a detail oblique view of a portion of the liquid discharge and intake port;

FIG. 36A is a flowchart showing an analysis method including an addition step and a measurement step, including a stirring treatment and a homogenization treatment, FIG. 36B is a flowchart showing the flow processing in addition steps A and B included in FIG. 36A, and FIG. 36C is a flowchart showing a process flow of the measurement processing included in FIG. 36A;

FIG. 37 is an exploded oblique view of a seal affixed to the upper surface of the sensor unit;

FIG. 38A is a plan view of a sensor unit, FIG. 38B is a plan view of the configuration of the top seal affixed to the upper surface of the sensor unit, FIG. 38C is a plan view of the configuration of the bottom seal affixed to the upper surface of the sensor unit, and FIG. 38D is a plan view showing a state in which the top seal and the bottom seal have been affixed to the upper surface of the sensor unit;

FIG. 39A is a plan view showing a state in which a seal provided to the user has been affixed, FIG. 39B is a plan view showing a state in which the top seal has been peeled away from the state in FIG. 39A, and FIG. 39C is a plan view showing a state in which the bottom seal has been peeled away from the state in FIG. 39B;

FIG. 40 is a diagram showing a state in which the seal is steadily peeled off as the product is used;

FIG. 41A is a top view of a port including a stirring member according to Embodiment 2 of the present invention, and FIG. 41B is a cross-sectional view along the G-G' line;

FIG. 42A is a detail view showing the configuration in the vicinity of a liquid discharge and intake port of the stirring member, and FIG. 42B is a cross-sectional view showing the internal structure in FIG. 42A;

FIG. 43A is a top view of a port including a stirring member according to Embodiment 3 of the present invention, and FIG. 43B is a plan view of the flow of the culture medium discharged from the stirring member;

FIG. 44A is a lateral cross-sectional view showing a state in which a port including a stirring member according to Embodiment 4 of the present invention is immersed in a culture medium in a culture vessel (well), and FIG. 44B is a lateral cross-sectional view showing the remaining medium left behind in the stirring vessel when the port in FIG. 44A has been pulled up out of the medium;

FIG. 45A is a lateral cross-sectional view showing a state in which a port including a stirring member according to Embodiment 5 of the present invention is immersed in a culture medium in a culture vessel (well), and FIG. 45B is a lateral cross-sectional view showing the remaining medium left behind in the stirring vessel when the port in FIG. 45A has been pulled up out of the medium;

FIG. 46 is a detail cross-sectional view showing a rib formed in the stirring vessel of the stirring member in FIG. 45A, etc.; and FIG. 47A is a lateral cross-sectional view showing a state in which a port including a stirring member according to Embodiment 6 of the present invention is immersed in a culture medium in a culture vessel (well), and FIG. 47B is a detail view showing the vicinity of the liquid discharge and intake port.

DESCRIPTION OF EMBODIMENTS

Embodiment 1

The cell culture analyzer 1 according to an embodiment of the present invention will now be described with reference to the appended drawings.

Summary of Cell Culture Analyzer 1

FIG. 1 shows the configuration of the cell culture analyzer 1.

The cell culture analyzer 1 is a device that electrochemically senses the concentration of a specific component contained in a medium in a state in which a part (sensing electrode) of a sensor 43 is immersed in the medium (liquid) contained in a culture vessel, and comprises an analysis unit 2, a drive unit 3 (serving as an air pressure supply unit), and a control unit 4 that controls the analysis unit 2 and the drive unit 3. The control unit 4, the analysis unit 2, and the drive unit 3 are connected by an electrical cable 5. The drive unit 3 and the analysis unit 2 are connected by a piping tube 6.

Figure 2:
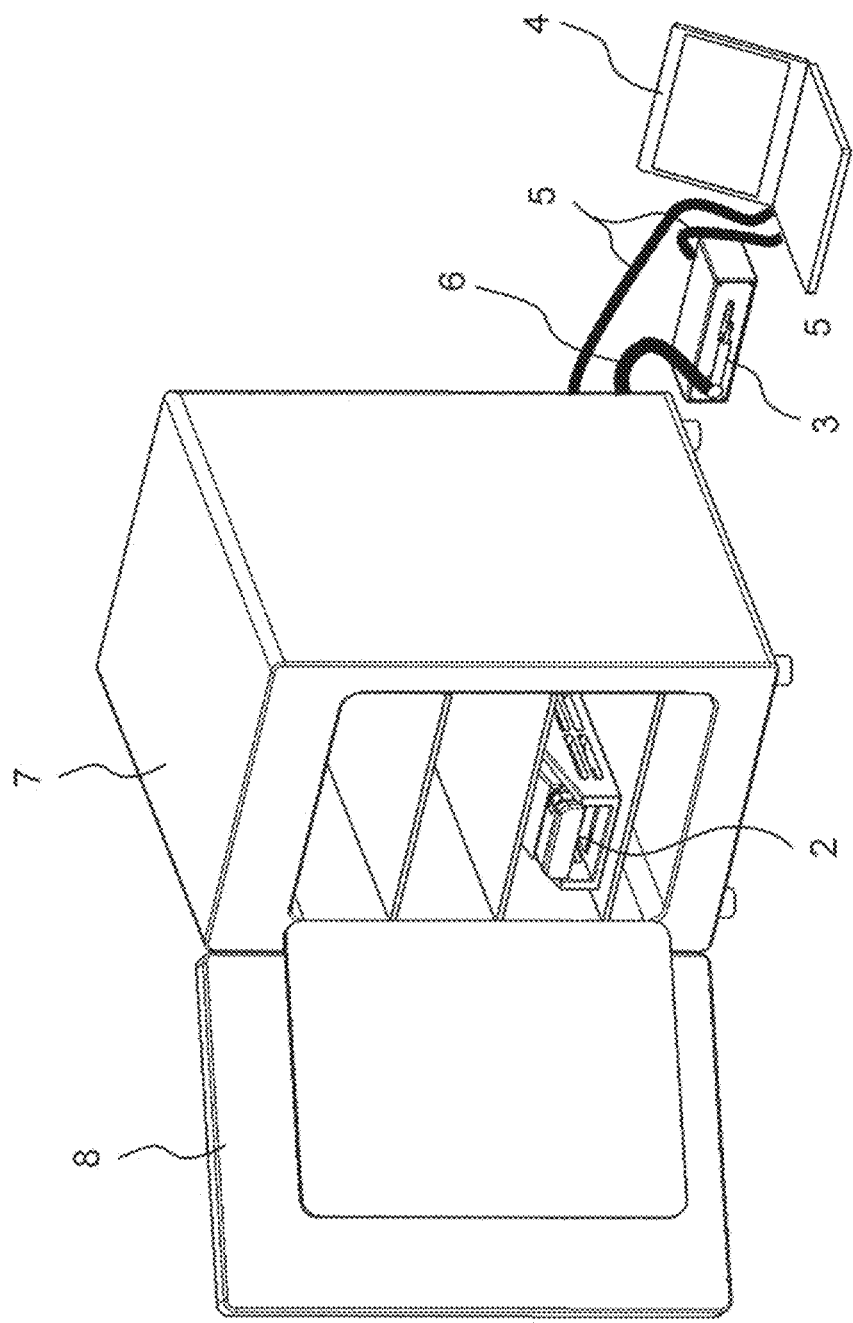
FIG. 2 is a diagram showing the state when the analysis unit of the cell culture analyzer in FIG. 1 is installed in a culture incubator.

FIG. 2 shows a usage example of the cell culture analyzer 1 disposed in a culture incubator 7.

The analysis unit 2 of the cell culture analyzer 1 is disposed in the culture incubator 7. The control unit 4 connected to the analysis unit 2 by the electrical cable 5, and the drive unit 3 connected to the analysis unit 2 by the piping tube 6, are disposed outside the culture incubator 7.

Consequently, the user can analyze the culture state in the culture incubator 7 via the control unit 4 without having to open and close the door 8 of the culture incubator 7. That is, in analyzing the culture state, air contamination inside the culture incubator 7 can be prevented.

Figure 3B:
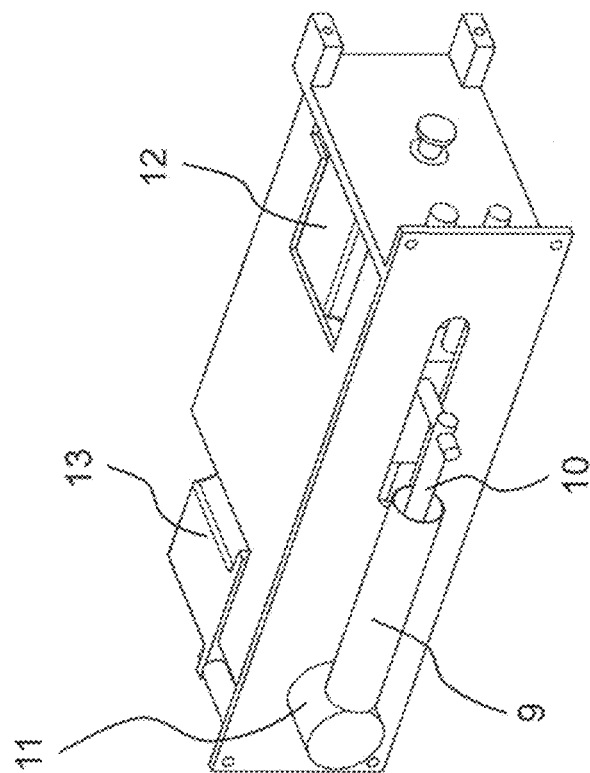
FIGS. 3A and 3B are diagrams showing the configuration of a drive unit included in the cell culture analyzer in FIG. 1.
Figure 3A:
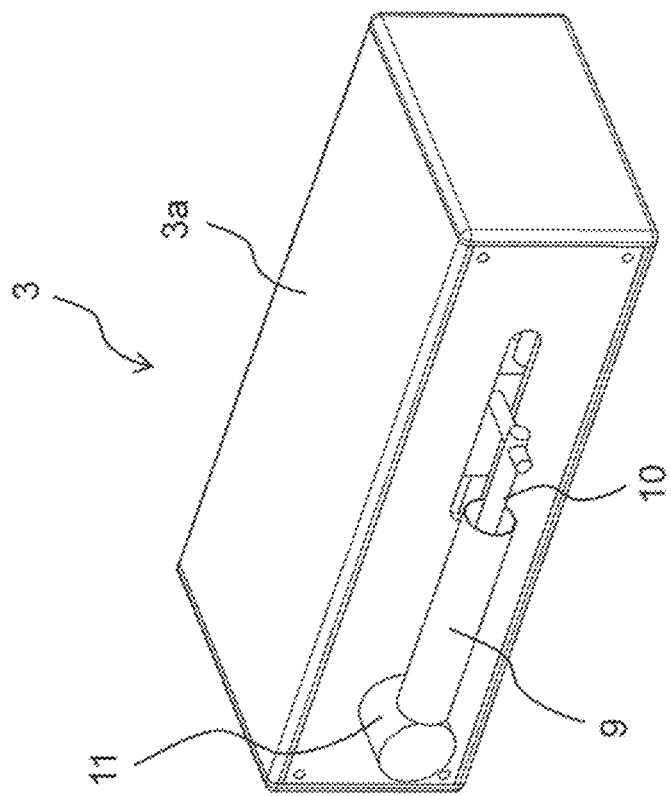

FIGS. 3A and 3B show the configuration of the drive unit 3.

The drive unit 3 is an air pressure supply unit for the analysis unit 2, and as shown in FIGS. 3A and 3B, has a syringe 9, a plunger 10, a multi-directional switching valve 11, a plunger motor 12, and a valve motor 13. The air pressure is adjusted by compressing or drawing in the air in the syringe 9 with the plunger 10. The plunger 10 is linked to the multi-directional switching valve 11.

The plunger motor 12 and a motor 13 for the multi-directional switching valve 11 are disposed in the housing 3a of the drive unit 3. These motors 12 and 13 are controlled by the control unit 4, which is connected via the electrical cable 5.

Figure 4:
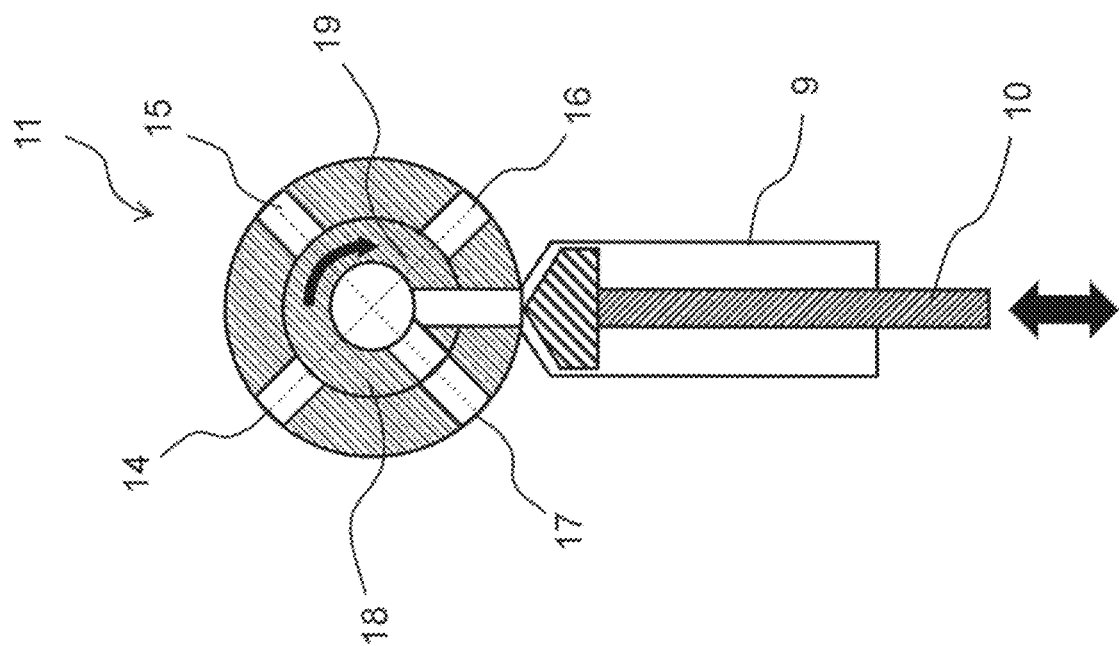
FIG. 4 is a cross-sectional view showing the configuration of a multi-directional switching valve included in the drive unit in FIG. 3A.

FIG. 4 shows the configuration of the multi-directional switching valve 11 included in the drive unit 3.

The multi-directional switching valve 11 has a valve 14 for the additive addition portion A, a valve 15 for the additive addition portion B, and a valve 16 for the stirring member, as air supply system valves for the analysis unit 2.

The multi-directional switching valve 11 has a stirring member valve 16 and an intake valve 17, as system valves for the analysis unit 2.

The multi-directional switching valve 11 controls the rotation of the rotating portion 18 to determine the position of a rotating flow path 19 in the circumferential direction, and is controlled so as to connect the flow path of a specific valve with the syringe 9 to supply air pressure.

Figure 5:
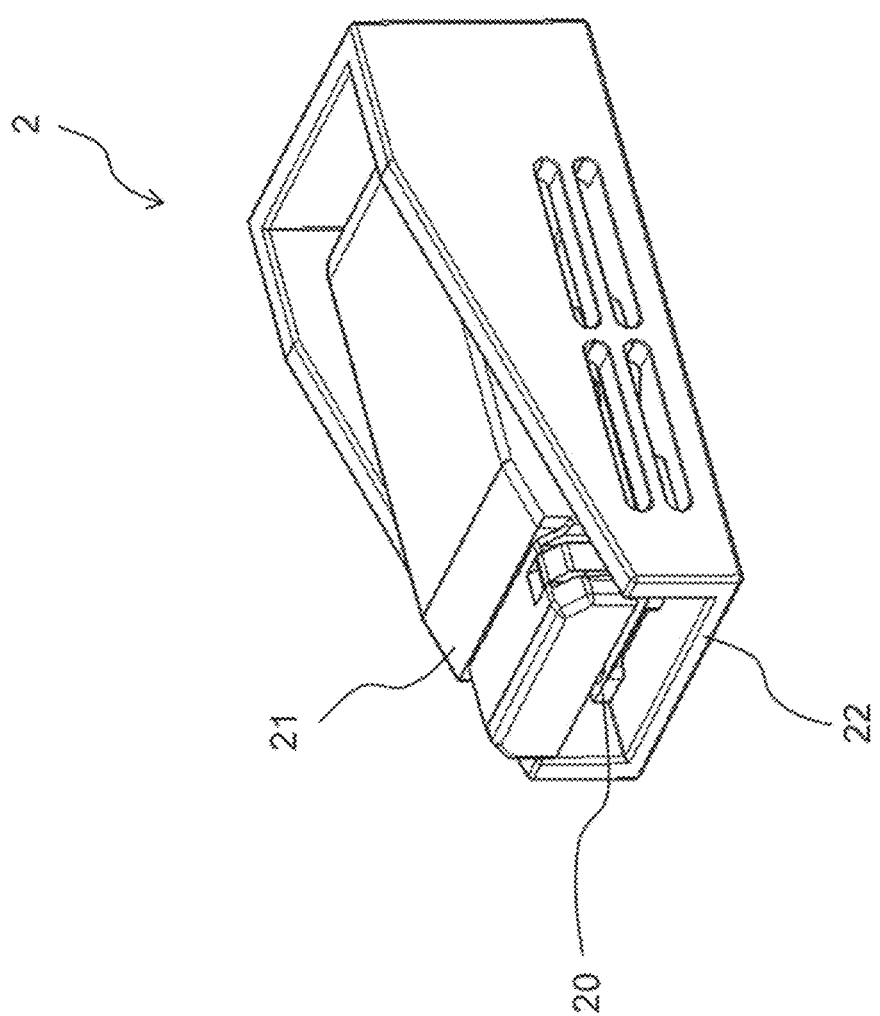
FIG. 5 is a diagram showing the configuration of an analysis unit included in the cell culture analyzer in FIG. 1.

More specifically, in the supply of air to the analysis unit 2, first, the rotation of the rotating portion 18 is controlled to connect the flow path of the intake valve 17 and the syringe 9. Then, the plunger 10 is pulled in the intake direction, and air is drawn into the syringe 9 through the intake valve 17. Next, the rotation of the rotating portion 18 is controlled so that the flow path of the syringe 9 is connected to the valves 14, 15, and 16 of a specific air supply system, and then the plunger 10 is depressed in the compression direction to send air to the specific valves 14, 15, and 16, FIG. 5 shows the configuration of the analysis unit 2.

The analysis unit 2 is designed to be short in the horizontal direction, low in the height direction, and long in the depth direction so that a plurality of units can be installed in the culture incubator. The reason for this is that the culture space of a typical culture incubator is long in the depth direction and low in the height direction, and this shape is suitable for this.

The analysis unit 2 has an adapter unit 20, a top unit 21, and a bottom unit 22, and is configured to sandwich the adapter unit 20 between the top unit 21 and the bottom unit 22.

As shown in FIG. 6, the adapter unit 20 is attached by being slid from a front opening 23 formed between the top unit 21 and the bottom unit 22. As a result, the height of the analysis unit 2 can be kept low.

Also, as shown in FIG. 6, the adapter bottom 24, the well plate 25, the adapter top 26, and the sensor unit 27 are disposed in the adapter unit 20 in that order, starting from the bottom.

Figure 7B:
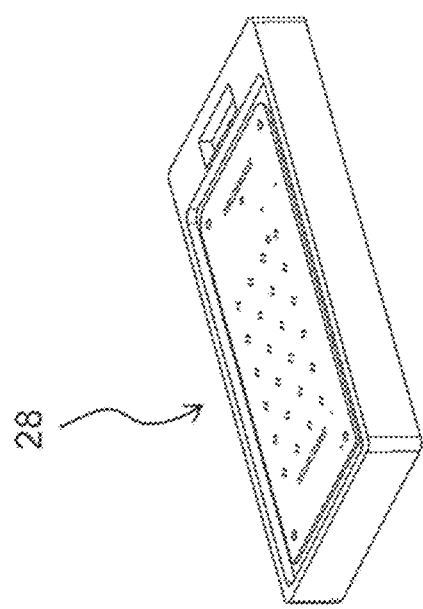
FIG. 7B is a diagram showing the configuration of a board unit installed in the adapter unit in FIG. 7A.
Figure 7A:
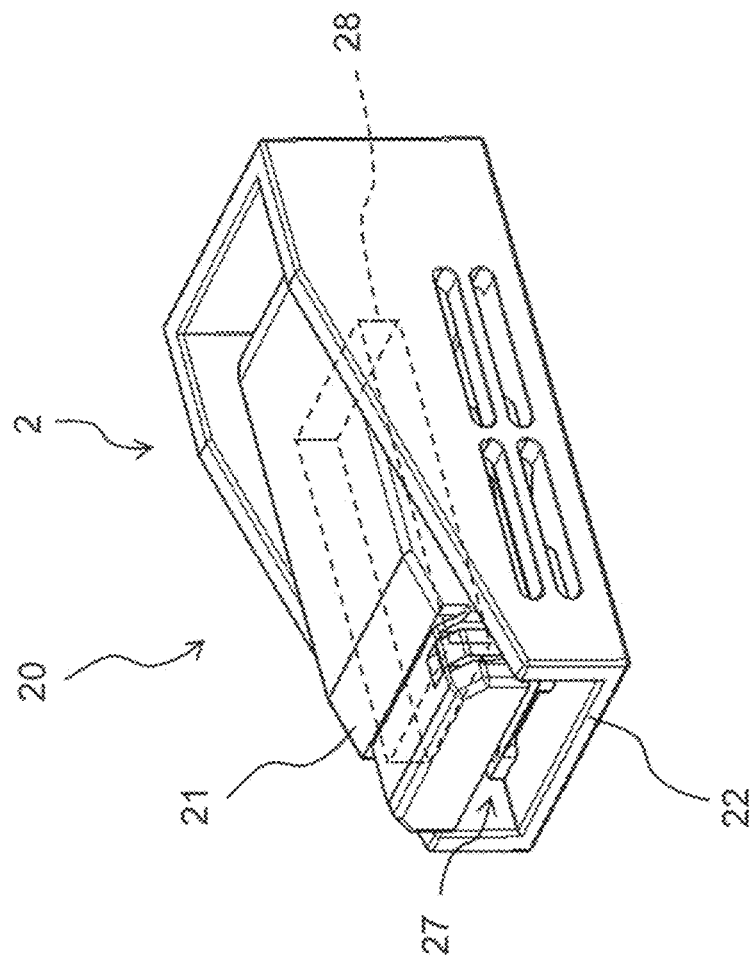
FIG. 7A is a diagram showing the configuration of the adapter unit in FIG. 6.

The top unit 21 of the adapter unit 20 shown in FIG. 7A includes the board unit 28 shown in FIG. 7B.

Figure 8:
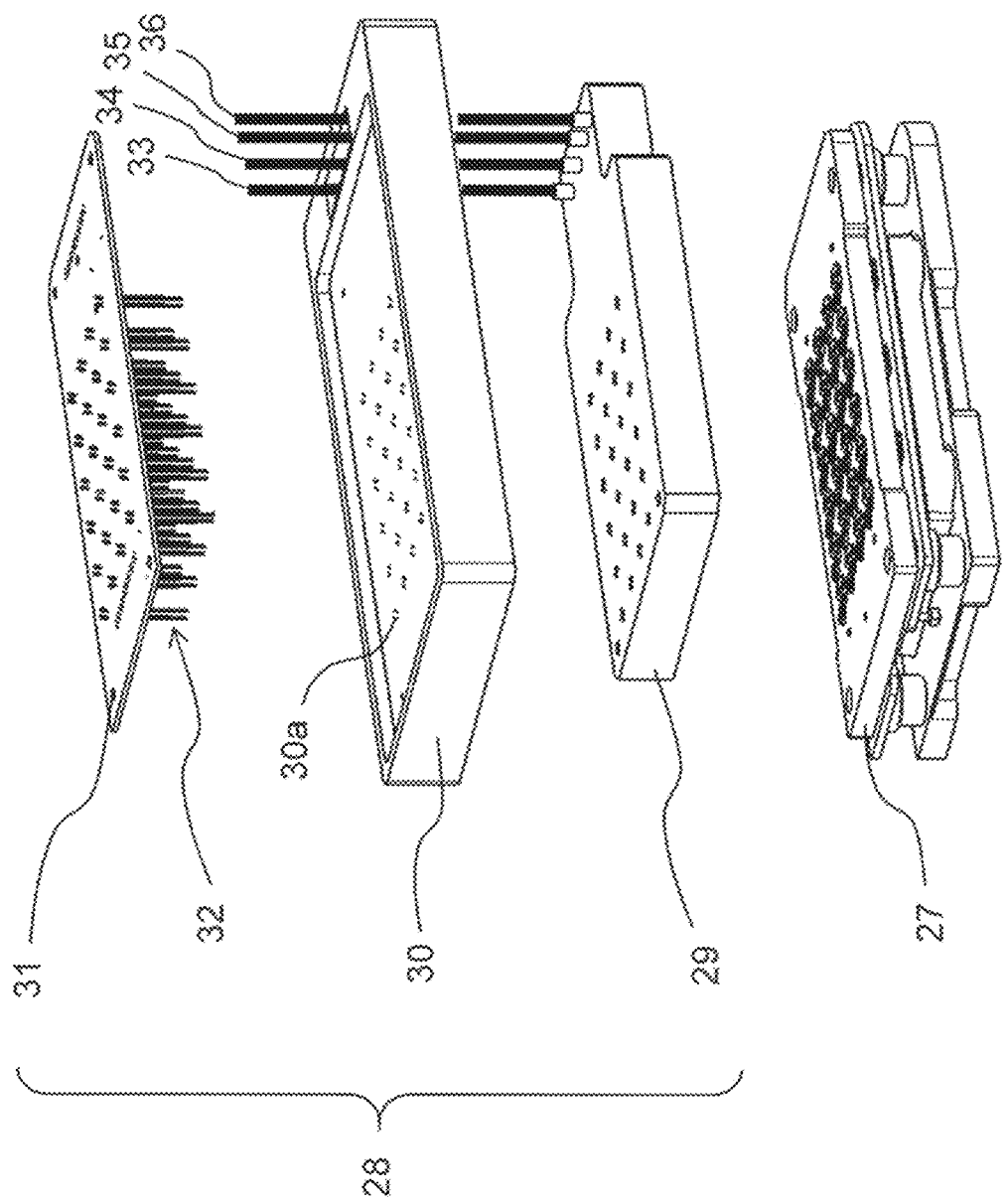
FIG. 8 is an exploded oblique view showing the configuration of a board unit included in an adapter unit disposed on a sensor unit.

FIG. 8 shows an exploded oblique view of the board unit 28 disposed on the sensor unit 27. As shown in FIG. 8, a piping board portion 29, a board base 30, and a board 31 are disposed in the board unit 28 is that order from below the side opposite the sensor unit 27.

The piping board portion 29 includes an air pipe to which an air flow path from the drive unit 3 is connected. The board base 30 is provided so that the board 31 is attached to the upper surface thereof. The board 31 is provided with a connecting portion 32 for electrical connection to an electrochemical sensor 43 (see FIG. 14, etc.) provided to the sensor unit 27 below.

A plurality of connecting portions 32 are disposed facing downward from the board 31, go through contact through-holes 30a disposed in the board base 30, pass through the piping hoard portion 29, and are electrically connected to a plurality of sensors 43 disposed at corresponding positions in the lower sensor unit 27.

A wiring pattern electrically connected to the connecting portions 32 is provided on the board 31. The board 31 is connected to the external control unit 4 (see FIG. 1, etc.) via the electrical cable 5.

Figure 9:
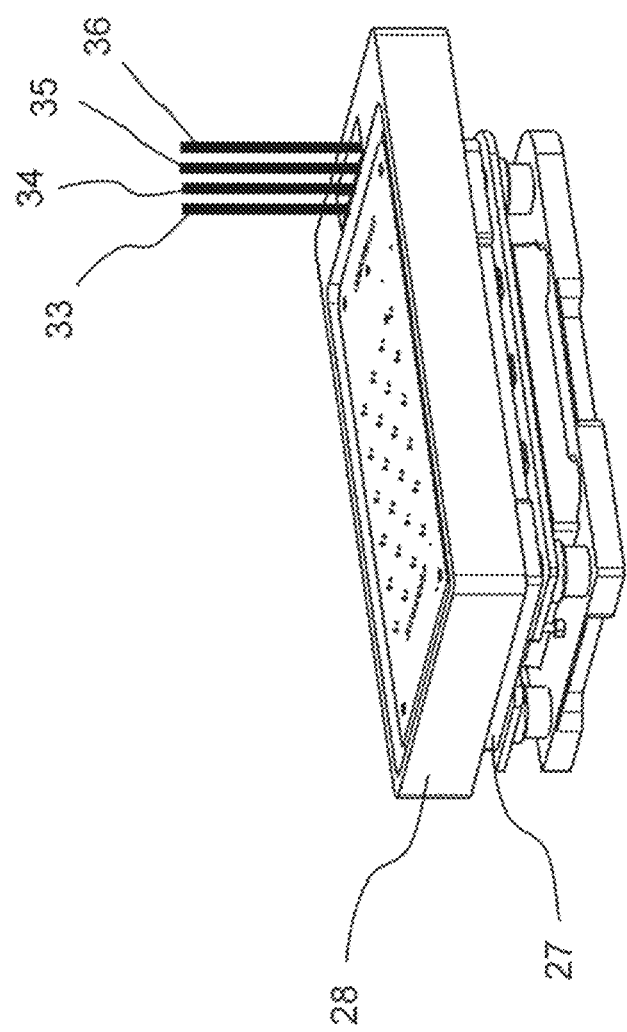
FIG. 9 is an oblique view showing the connection state between the board unit and a piping tube.

FIG. 9 shows the connection state: between the hoard unit 28 and the piping tubes 33, 34, 35 and 36.

In this embodiment, a total of four kinds of piping tubes connected to the drive unit 3 are connected to the board unit 28.

More specifically, the board unit 28 is provided with an additive addition portion A piping tube 33 and an additive addition portion B piping tube 34, as piping tubes for the air supply system to the board unit 28.

The board unit 28 is further provided with an intake piping tube 36, as an intake system valve for the analysis unit 2.

The stirring member piping tube 35 is provided to the board unit 28 as a bi-directional valve for air supply and intake.

Figure 10:
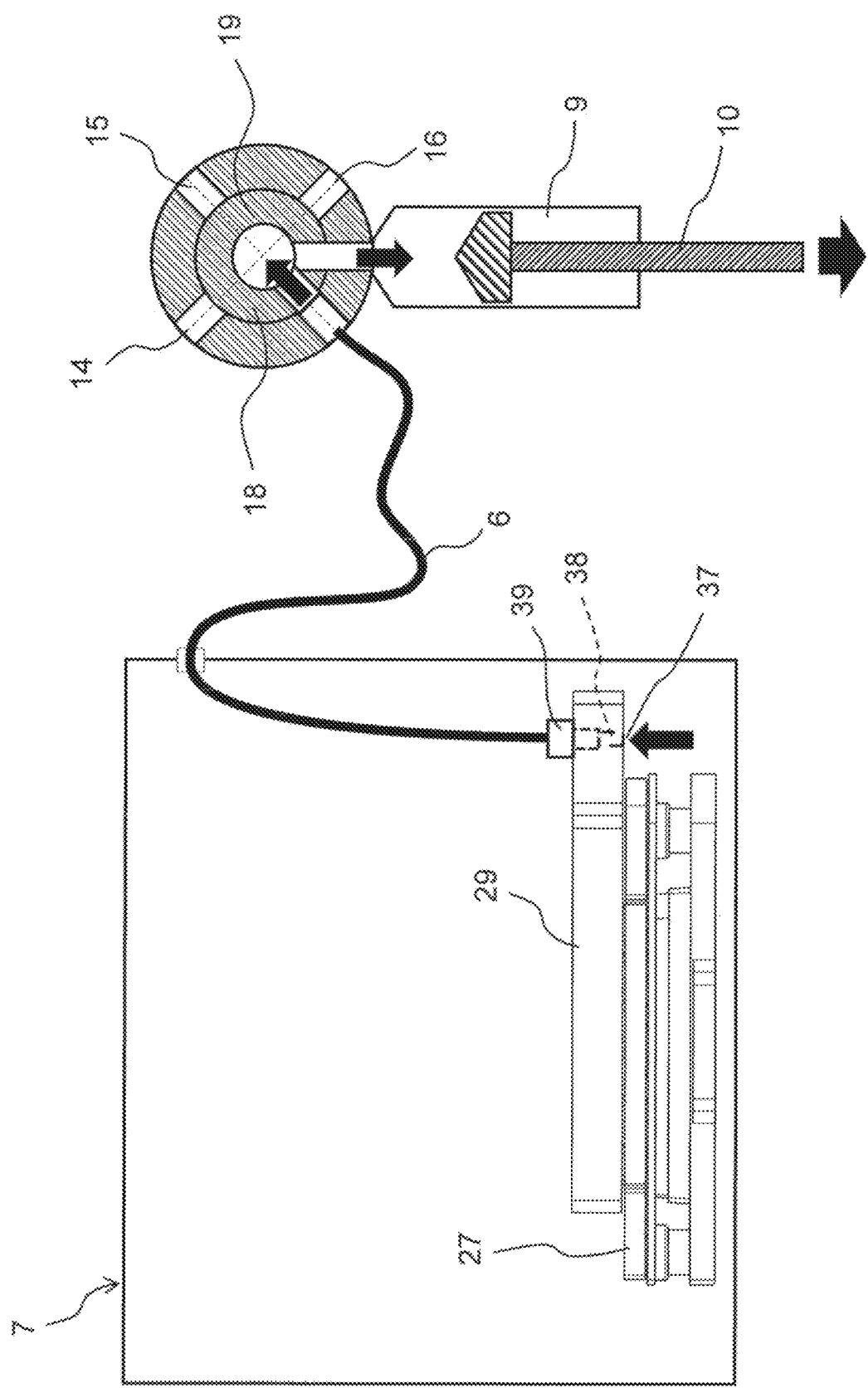
FIG. 10 is a diagram showing the configuration of an intake port used as an air pressure supply unit.

FIG. 10 shows the configuration of an intake port used as an air pressure supply unit.

The air pressure supply unit has an air inlet (intake port) 37 for drawing in the air inside the culture incubator 7 that houses the culture vessels.

More specifically, the air inlet (intake port) 37 is provided on the lower bottom surface of the piping board portion 29. The air inlet (intake port) 37 goes through the through-hole 38 in the piping board portion 29, and is connected to the multi-directional switching valve 11 of the drive unit 3 via the piping tube 36 that is linked to the piping tube connecting portion 39 above.

Consequently, since the air pressure supply unit has the air inlet (intake port) 37 for drawing in the air that is inside the culture incubator 7 housing the culture medium vessel, contamination of the cell culture in the culture vessel can be prevented.

In other words, in this embodiment, the air inside the culture incubator 7 housing the culture medium container, that is, controlled air, is utilized as air pressure to the additive containers (additive A container 85, additive B container 86) and the stirring member 81. This prevents the contamination of the cell culture in the culture vessel.

Also, since the air inlet (intake port) 37 is provided on the lower bottom surface of the piping board portion 29, water droplets and the like can be prevented from flowing into through the opening of the air inlet 37.

Also, the piping tube 36 is formed from a moisture-permeable material such as a Nafion tube. This prevents the water in the culture incubator 7 from flowing into the drive unit 3, and prevents condensation in the drive unit 3.

FIGS. 11A to 11C show the routing of the piping formed on the piping board portion 29.

The piping tube 33 for the additive addition portion A is connected to the piping board portion 29. The culture vessel (well plate 25) in this embodiment contains 24 wells 80. Therefore, the piping for the additive addition portion A branches off into 24 parallel pipes, and the outlet openings of the pipes are disposed above specific wells 80.

Similarly, the piping tube 34 for the additive addition portion B is connected to the piping board portion 29. The piping for the additive addition portion B branches off into 24 parallel pipes, and the outlet openings of the pipes are disposed above specific wells 80.

Similarly, the piping tube 35 for the stirring member is connected to the piping board portion 29. The piping for the stirring member branches off into 24 parallel pipes, and the outlet openings of the pipes are disposed above specific wells 80.

That is, the same air pressure is applied all at once to the additive addition portions A of all 24 of the wells 80 of the culture vessel. Similarly, the same air pressure is applied all at once to the additive addition portions B of all 24 of the wells 80. Similarly, the same air pressure is applied all at once to the stirring members of all 24 of the wells 80.

Figure 12:
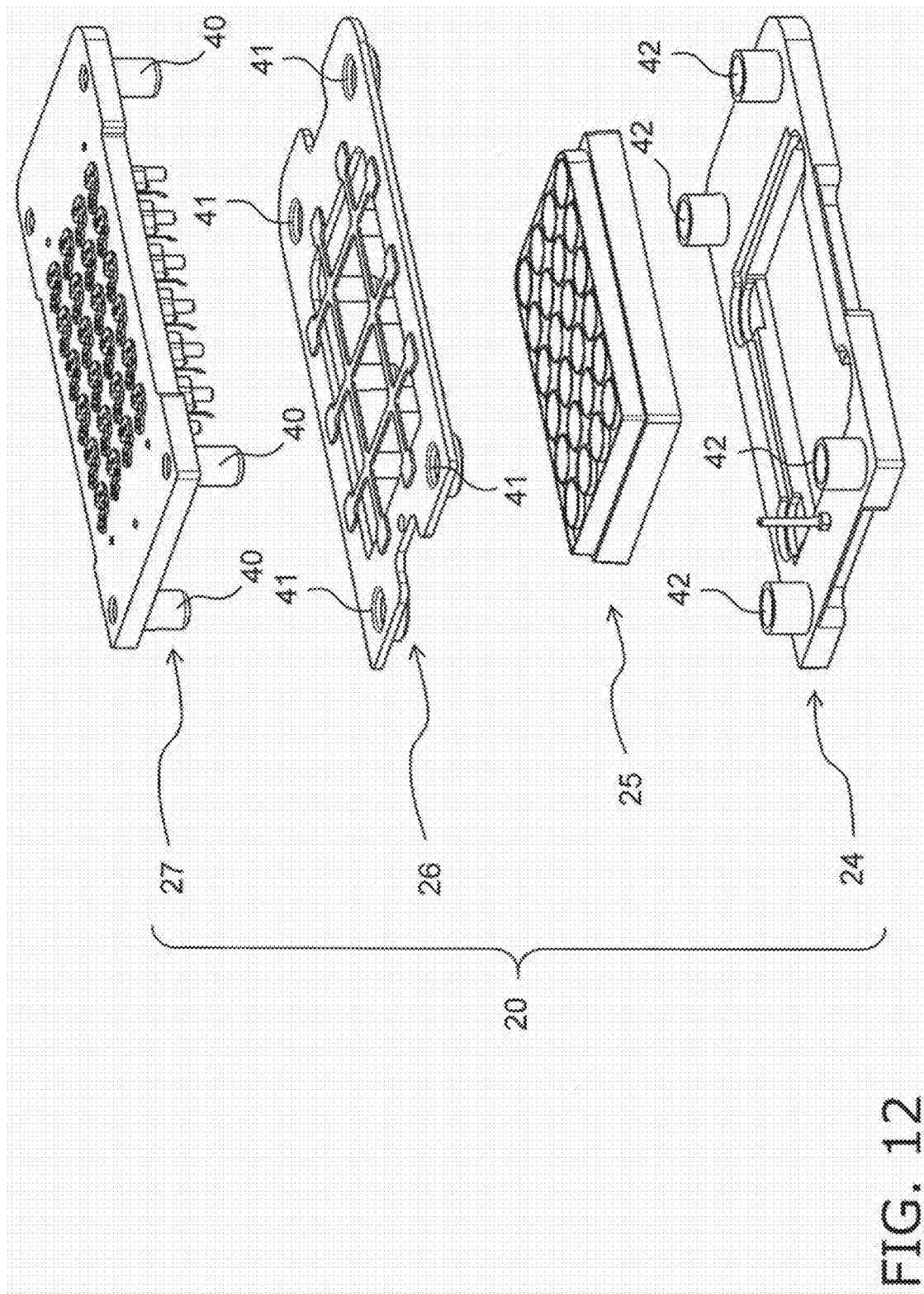
FIG. 12 is an exploded oblique view showing the configuration of an adapter unit.

FIG. 12 shows the configuration of the adapter unit 20.

As shown in FIG. 12, the adapter unit 20 has an adapter bottom 24 (as a culture vessel installation portion), a well plate 25 (as a culture vessel), an adapter top 26, and a sensor unit 27, placed in that order starting from the bottom.

In this embodiment, the well plate 25 has 24 wells 80 in a 4×6 matrix. The adapter top 26 is provided in order to adjust the height of the well plate 25, and a different adapter top 26 is used according to the height of the well plate 25. The reason for this is to adjust the height relationship between the sensor unit 27 and the well plate 25 when the sensor unit 27 is placed on the adapter top 26.

There are several types of well plate 25, including general-purpose types, and the proper adapter top 26 is used according to this type.

In the sensor unit 27 disposed on the adapter top 26, four leg portions (supports) 40 provided on the lower surface side thereof go through through-holes 41 in the adapter top 26 below, and are inserted into positioning holes 42 provided in the adapter bottom 24 serving as a culture vessel installation portion.

Consequently, the sensor unit 27 is installed on the well plate 25 spaced apart at a specific gap. That is, the sensor unit 27 is provided with leg portions 40 for ensuring a housing space for the well plate 25 (culture vessel) on the adapter bottom 24. The sensor unit 27 is disposed on the adapter bottom 24 in a state of being supported by the leg portions 40.

As discussed above, the leg portions 40 support the sensor unit 27 with respect to the adapter bottom 24 in order to ensure a housing space for the well plate 25 (culture vessel) (a gap between the upper surface of the adapter bottom 24 and the lower surface of the sensor unit 27).

Here, the supports that support the sensor unit 27 is not limited to the leg portions 40 provided to the sensor unit 27. For instance, the supports may be provided on the adapter bottom 24 side, so long as they support the sensor unit 27 from below with respect to the adapter bottom 24.

Figure 13B:
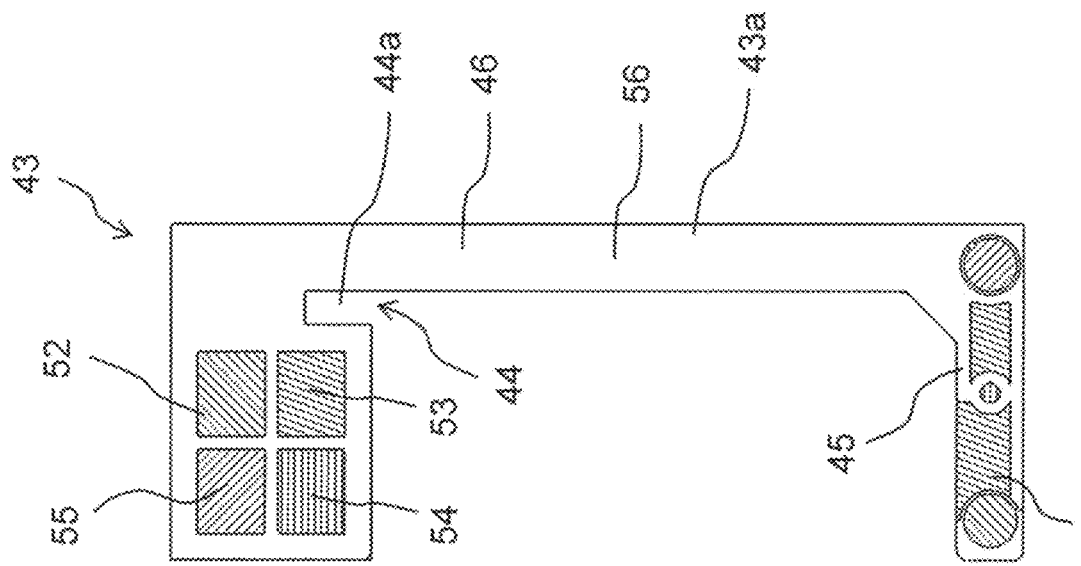
FIGS. 13A and 13B are diagrams showing the configuration of a sensor disposed in a sensor unit.
Figure 13A:
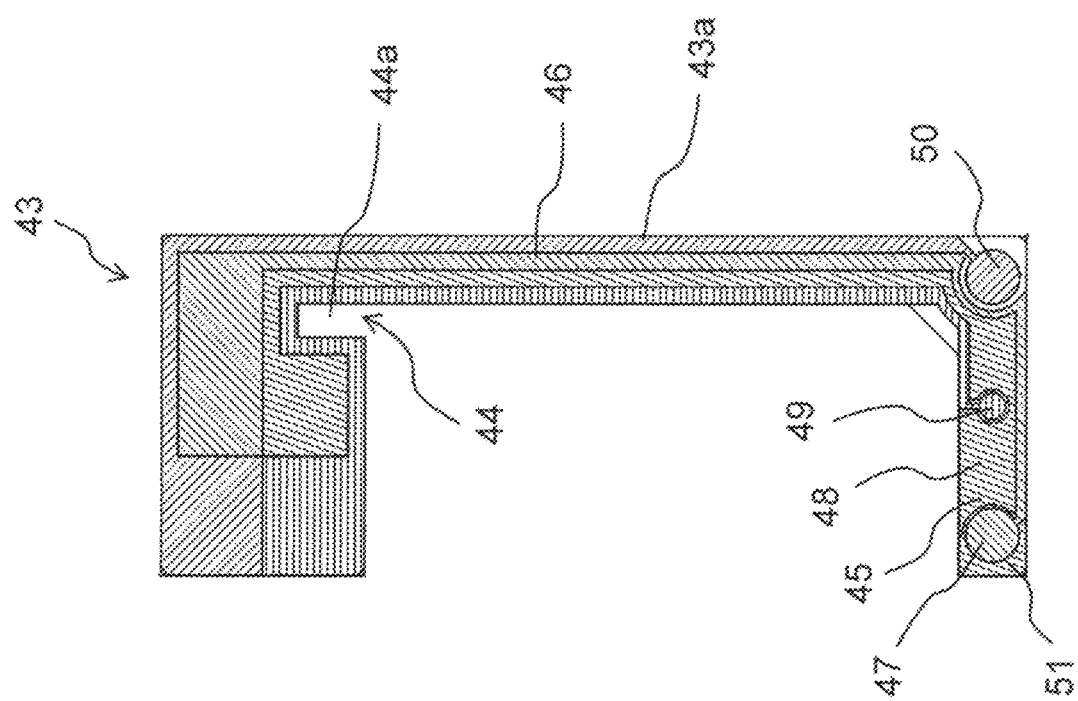

FIGS. 13A and 13B show the configuration of the sensor 43 disposed in the sensor unit 27.

As shown in FIGS. 13A and 13B, the sensor 43 in this embodiment has a main body portion 43a that is substantially L-shaped, except for the upper portion where electrode pads 52 to 55 are disposed. The sensor 43 has a bent portion 44 that is bent during use, at the upper part of a vertical edge of the substantially L-shaped main body portion 43a.

The bent portion 44 is a portion in which the other substantially L-shaped portions (lateral edge portion 45 and vertical edge portion 46) are bent at a substantially right angle with respect to the upper portion where the electrode pads 52 to 55 are disposed. Thus bending the main body portion 43a at a substantially right angle at the bent portion 44 allows the sensing electrodes 47, 48, 49, and 50 of the sensor 43 to be immersed in the wells 80.

A notched portion 44a is located near the bent portion 44, and is formed at the portion where the upper portion where the electrode pads 52 to 55 are disposed is linked to the substantially L-shaped portion (lateral edge portion 45 and vertical edge portion 46). The notched portion 44a is formed by a cutout formed in the lengthwise direction of the vertical edge portion 46.

This allows the substantially L-shaped portion (lateral edge portion 45 and vertical edge portion 46) to be moved in the lengthwise direction of the vertical edge portion 46 without the crease formed in bending with respect to the upper portion where the electrode pads 52 to 55 are disposed being limited to the portion where the vertical edge portion 46 is connected to the upper portion where the pads 52 to 55 are disposed.

Consequently, the portion that because a crease formed in the sensor 43 can be moved according to the positional relationship, such as the size of the sensor 43 and the depth of the wells 80.

In this embodiment, the sensor 43 is substantially L-shaped, and the culture state in the culture vessel is sensed by placing the lateral edge portion 45 of the sensor in the wells 80 of the culture vessel and holding this portion in a horizontal state.

Also, sensing electrodes 47 to 50 for sensing the culture state in the culture vessel are provided on the lower lateral edge portion 45 of the sensor 43.

This allows the electrode surface area of the sensing electrodes 47 to 50 to be larger, which improves the sensitivity of the sensor 43. The horizontal width of the lower lateral edge portion 45 of the sensor 43 is greater than the horizontal width of the upper vertical edge portion 46.

The shape of the sensor 43 is not limited to substantially L-shaped, and may, for example, be substantially I-shaped, substantially inverted T-shaped, or the like. Also, in order to improve the sensitivity of the sensor 43, the horizontal dimension (width) of the horizontal edge portion of the sensor 43 is preferably made wider.

The lateral edge portion 45 of the sensor 43 is provided with a first working electrode 47, a counter electrode 48, a reference electrode 49, and a second working electrode 50 as sensing electrodes.

Also, a silver layer (a silver layer and/or a silver chloride layer is provided on the surface of the reference electrode 49, A reagent layer formed from an enzyme and a mediator, etc., is provided on the surfaces of the first and second working electrodes 47 and 50. The sensing electrode portions thereof are covered with a protective membrane 51.

The sensor 43 electrochemically senses the concentration of a specific component of the medium in a state in which the first working electrode 47, the counter electrode 48, the reference electrode 49, and the second working electrode 50 are immersed in the medium in the culture vessel.

For instance, when sensing the concentration of the glucose component in the medium, the reagent layer immobilized on the surface of the first working electrode 47 contains an enzyme (such as GOx) and a redox mediator.

The principle behind this glucose detection is that glucose that permeates from the medium through the protective membrane 51 is oxidized in an enzymatic reaction with an enzyme (such as GOx) in the reagent layer and turns into gluconolactone, and at the same time, the redox mediator in the reagent layer is reduced into a reductant. The glucose concentration in the medium can be measured by measuring, as a current value, the electrons generated when this reductant goes back to being an oxidant.

The protective membrane 51 is provided to allow glucose in the medium to penetrate into the sensing electrode portion of the sensor 43 while limiting its permeation, and to prevent the components of the reagent layer (enzyme and mediator) immobilized on the first working electrode 47 from flowing to the outside of the protective membrane 51.

The enzyme and mediator are cross-linked and immobilized on electrodes. Therefore, the reagent layer is polymerized and its molecular weight increases. Consequently, glucose can permeate the protective membrane 51, while the enzyme and mediator are prevented from flowing out of the protective membrane 51 (see WO 2019/146788 for details).

The first working electrode 47, the counter electrode 48, the reference electrode 49, and the second working electrode 50 are electrically connected to the electrode pads 52 to 55, which are connection terminals above the sensor 43. The electrode pads 52 to 55 have a first working electrode pad 52, a counter electrode pad 53, a reference electrode pad 54, and a second working electrode pad 55.

A reagent for sensing lactic acid, for example, is immobilized on the second working electrode 50.

As shown in FIGS. 13A and 13B, the sensor 43 is configured such that sensing electrodes, which are measurement units (first working electrode 47, counter electrode 48, reference electrode 49, second working electrode 50), and connection terminal portions (first working electrode pad 52, counter electrode pad 53, reference electrode pad 54, second working electrode pad 55) are formed on the same board.

A PET (polyethylene terephthalate) film, which is a resin material, is used as the base material, for example.

The first working electrode 47, the counter electrode 48, the reference electrode 49, and the second working electrode 50 are formed on the same board. Also, in the lateral edge portion 45 of the sensor 43, the first working electrode 47, the counter electrode 48, the reference electrode 49, and the second working electrode 50 are disposed substantially horizontally in their usage state. In order to increase the surface area of the working electrodes, a plurality of working electrodes 47 and 50 are disposed in left and right symmetry in the horizontal direction around the reference electrode 49. As a result, the electrode surface area of the working electrodes 47 and 50 can be increased to raise the detection sensitivity.

The method for manufacturing the sensor 43 will now be described.

First, a gold electrode layer is formed by sputtering on the upper surface of a PET (polyethylene terephthalate) film, which is a resin material. Next, the electrode layer is patterned in an approximate L shape to match the sensor 43. That is, the electrode layer is transpired with a laser, and thereby formed into a substantially L-shaped electrode layer.

Further, the substantially L-shaped electrode layer is divided into a first working electrode 47, a counter electrode 48, a reference electrode 49, and a second working electrode 50. Signals are taken off from the four divided conductive paths at the connection terminal portions (first working electrode pad 52, counter electrode pad 53, reference electrode pad 54, second working electrode pad 55).

After this substantially L-shaped electrode layer has been divided up for use as the first working electrode 47, the counter electrode 48, the reference electrode 49, and the second working electrode 50, a resist film 56 is provided in a state in which the electrode portions are masked off. After this, a silver layer (a silver layer and/or a silver chloride layer) is provided on the surface of the reference electrode 49, and a reagent layer is provided on the surfaces of the first working electrode 47 and the second working electrode 50.

The first working electrode 47, the counter electrode 48, the reference electrode 49, and the second working electrode 50 are covered by the protective membrane 51.

Figure 14:
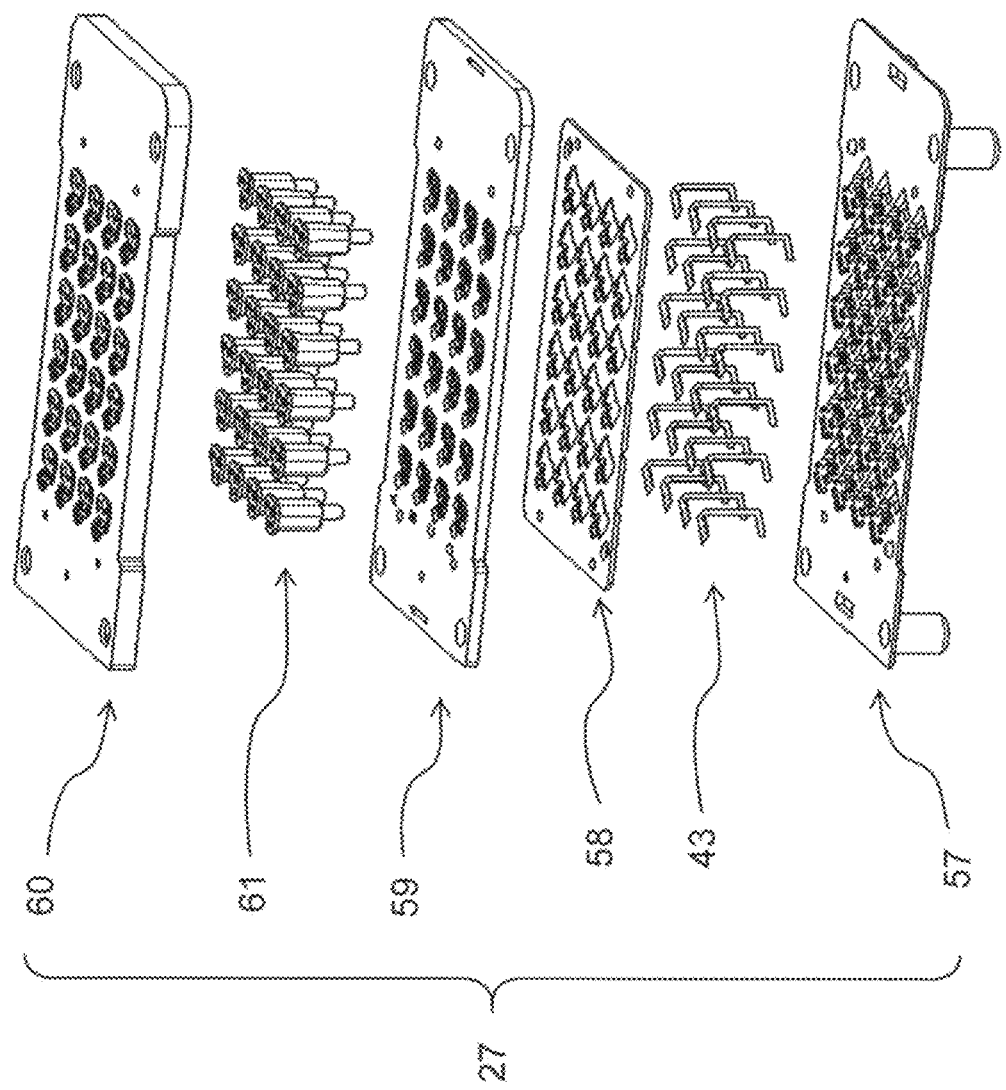
FIG. 14 is an exploded oblique view showing the configuration of a sensor unit.

FIG. 14 shows an exploded oblique view of the sensor unit 27.

In the sensor unit 27, a bottom plate 57, a middle plate 58, a top plate 59, and a gasket sheet (board) 60 are stacked in this order, starting from the bottom.

Then, the sensor 43 is fixed and held by the bottom plate 57, the middle plate 58, and the top plate 59, and is bent substantially vertically downward.

The upper portion of a port (additive supply member) 61 is fixed to the upper surface of the top plate 59, and goes through the top plate 59, the middle plate 58, and the bottom plate 57, and the lower portion is disposed below the bottom plate 57.

FIGS. 15A to 15C are diagrams illustrating the method for immobilizing and holding the sensor 43.

As shown in FIG. 15A, first, a plurality (a 4×6 matrix) of sensors 43 are placed on the bottom plate 57. The sensors 43 are placed in parallel with the diagonal line of the rectangular bottom plate 57 so that length of the sensors 43 in the lengthwise direction will be sufficient.

Next, as shown in FIG. 15B, the middle plate 58 is placed over the sensors 43 mounted on the bottom plate 57.

Next, as shown in FIG. 15C, the middle plate 58 slides in a direction parallel to the diagonal line of the bottom plate 57 to fix the bottom plate 57 and the middle plate 58. At this point, the sensors 43 are fixed and held by being sandwiched between the bottom plate 57 and the middle plate 58.

The method for fixing and holding the sensors 43 will be described in more specific terms with reference to FIGS. 16A to 18B.

FIG. 16A shows a state in which a plurality of sensors 43 have been placed on the bottom plate 57, and is a diagram showing FIG. 15A more specifically. FIG. 16B is a detail view of the A portion in FIG. 16A.

FIG. 16A is a top view showing a state in which a plurality of sensors 43 have been mounted on the bottom plate 57, In this state, the sensors 43 are placed in parallel with the diagonal line of the rectangular bottom plate 57. In FIG. 16A, each sensor 43 is such that a connection terminal portion 62 is disposed in the upper right direction on the drawing, and a sensing electrode 66 (a measurement unit) is disposed in the lower left direction.

As shown in FIG. 16B, a positioning portion 67 that surrounds and fixes the connection terminal portion 62 of the sensor 43 from all four sides is provided on the bottom plate 57. On the bottom plate 57, at least one fixing portion 63 that mates with the middle plate 58 and fixes the middle plate 58 and the bottom plate 57 in the up and down direction is provided.

Also, a slide guide protrusion 64 is provided on the bottom plate 57. A through-hole 65 is provided on the bottom plate 57, through which the sensor 43 is bent downward.

FIG. 17A is a diagram showing a state in which the middle plate 58 is placed over the sensors 43 mounted on the bottom plate 57, and is a diagram showing FIG. 15B more specifically. FIG. 17B is a detail view of the B portion in FIG. 17A.

FIG. 17A is a top view of a state in which the middle plate 58 has been placed over the sensors 43 mounted on the bottom plate 57. In this state, the sensors 43 are placed in parallel with the diagonal line of the rectangular bottom plate 57. In FIG. 17A, the sensors 43 each have a connection terminal portion 62 disposed in the upper right direction of the drawing, and a sensing electrode 66 (a measurement unit) disposed in the lower left direction.

As shown in FIG. 17B, the middle plate 58 is provided with a slide hole 68 with which a slide guide protrusion 64 provided to the bottom plate 57 is slidably mated, and a fixed portion 69 that mates with a fixing portion 63 of the bottom plate 57. The middle plate 58 is put over the bottom plate 57 in a state in which the slide guide protrusion 64 provided on the bottom plate 57 has been passed through the slide hole 68.

Consequently, the middle plate 58 slides with respect to the bottom plate 57 in the direction in which the slide guide protrusion 64 slides along the slide hole 68.

FIG. 18A is a more specific diagram of FIG. 15C, showing a state in which the middle plate 58 is slid with respect to the bottom plate 57 in a direction substantially parallel to the diagonal line of the bottom plate 57, so that the middle plate 58 is fixed to the bottom plate 57. FIG. 18B is a detail view of the C portion in FIG. 18A.

In the state shown in FIG. 18A, the sensors 43 are placed in parallel with the diagonal line of the rectangular bottom plate 57. In FIG. 18A, the sensors 43 each have a connection terminal portion 62 disposed in the upper right direction of the drawing, and a sensing electrode 66 (a measurement unit) disposed in the lower left direction.

As shown in FIG. 18B, when the middle plate 58 is slid in a direction substantially parallel to the diagonal line of the bottom plate 57, the bottom plate 57 and the middle plate 58 are fixed. In this state, the slide guide protrusion 64 provided to the bottom plate 57 slides along the slide hole 68, and the fixing portion 63 of the bottom plate 57 is mated with the fixed portion 69 of the middle plate 58.

More specifically, the fixing portion 63 of the bottom plate 57 is a prong, and the fixed portion 69 of the middle plate 58 is a mating portion to which the prong is latched.

As a result, the connection terminal portion 62 of the sensor 43 is sandwiched between the bottom plate 57 and the middle plate 58 from above and below and fixed in this positioned state.

FIG. 19A is a top view of the middle plate 58 fixed to the bottom plate 57. FIG. 19B is a cross-sectional view along the D-D' line in FIG. 19A.

As shown in FIG. 19B, the sensors 43 placed on the bottom plate 57 are positioned and fixed while being sandwiched between the bottom plate 57 and the middle plate 58. Each of the sensors 43 is provided with one fixing portion 63 and one fixed portion 69. The bottom plate 57 and the middle plate 58 are fixed in the horizontal direction and the height direction by the fixing portion 63 and the fixed portion 69 at a plurality of places. As a result, the sensors 43 are positioned and fixed while being sandwiched between the bottom plate 57 and the middle plate 58.

FIG. 20A shows a state in which a sensor 43 that has been positioned and fixed while being sandwiched between the bottom plate 57 and the middle plate 58 is further bent downward from the bent portion 44 at the vertical edge upper part. FIG. 20B is an oblique view of a state in which the top plate 59 is disposed on the middle plate 58, as seen from below the bottom plate 57, and FIG. 20C is a cross-sectional view showing the cross-sectional structure thereof.

In this embodiment, when the top plate 59 is placed over the upper surface of the middle plate 58 shown in FIG. 20A, as shown in FIGS. 2013 and 20C, the pressing portion 71 formed so as to protrude downward from the lower surface of the top plate 59 goes through the through-hole 65 and moves downward in a state of being in contact with the upper surface of the sensor 43.

At this point, the support portion 70 that supports the lower edge side of the bent portion 44 of the sensor 43 is provided at the opening edge of the through-hole 65 of the bottom plate 57. The pressing portion 71 that pushes the upper edge side of the bent portion 44 of the sensor 43 downward is provided at a portion of the top plate 59 that is opposite the support portion 70.

Consequently, the upper surface of the sensor 43 is pushed down by the pressing portion 71, so that the sensor 43 is bent from near the base of the vertical edge portion 46 and is supported from below by the support portion 70 provided on the upper surface side of the middle plate 58.

As shown in FIG. 20C, the support portion 70 has an upper surface curved shape including a curved surface on its upper surface. Also, as shown in FIG. 20C, the pressing portion 71 has a lower surface curved shape including a curved surface on its lower surface.

Consequently, as shown in FIGS. 20B and 20C, when the sensor 43 is sandwiched between the top plate 59 and the bottom plate 57 from above and below, the bent portion 44 of the sensor 43 is held in a state of being sandwiched from above and below by the support portion 70 and the pressing portion 71.

Therefore, the sensor 43 is bent along the one-dot chain line in the drawing around the bent portion 44, so that the lateral edge portion 45 of the sensor 43 (the portion where the first working electrode 47, the counter electrode 48, reference electrode 49, and the second working electrode 50 are present) is disposed substantially in the horizontal direction in a stable state below.

In this substantially horizontal state, the lateral edge portion 45 of the sensor 43 (the first working electrode 47, the counter electrode 48, the reference electrode 49, and the second working electrode 50) is held in a stable position in each well 80 of the culture vessel, and the culture state in each well 80 can be properly sensed.

Also, since the curve of the arc portion of the bent portion 44 of the sensor 43 is defined by the bottom plate 57 and the top plate 59, no excessive stress is exerted on the bent portion 44, so it is possible to prevent disconnection of sensor 43 due to cracking.

The bent portion 44 of the sensor 43 may be bent in a state in which the sensor 43 has been attached to either the top plate 59 or the bottom plate 57. Also, heat may be applied to the bent portion 44 in the bending of the sensor 43. In this case, the top plate 59 or the bottom plate 57 is unnecessary.

FIG. 21A is a top view of the gasket sheet 60.

As shown in FIG. 21A, a plurality of port input/output portions 72, which are disposed close together on the upper surfaces of the plurality of ports 61 (see FIG. 14), are disposed on the upper surface of the gasket sheet 60.

FIG. 21B is a detail view of one of the port input/output portions 72 in FIG. 21A. The port input/output portion 72 has an additive addition portion A addition port (upper surface opening) 73, an additive addition portion B addition port (upper surface opening) 74, and a stirring member air discharge and intake port 75. Also, the port input/output portion 72 has through-holes for connecting to the connection terminal portion 62 of the sensor 43. As shown in FIG. 21B, four through-holes are formed, namely, a through-hole 76 for the first working electrode pad, a through-hole 77 for the counter electrode pad, a through-hole 78 for the reference electrode pad, and a through-hole 79 for the second working electrode pad.

FIG. 22 is a cross-sectional view along the line of the port input/output portion 72 shown in FIG. 21B.

As described with reference to FIGS. 21A and 21B, a plurality of port input/output portions 72 are disposed on the upper surface of the gasket sheet 60. FIG. 22 shows the state before the board unit 28 is attached from above on the upper surface of the sensor unit 27 on the upper surface of which the gasket sheet 60 is disposed.

Before the board unit 28 is attached to the sensor unit 27, an additive is preloaded from the additive addition portion A addition port 73. As shown in FIG. 22, the additive addition portion A addition port 73 has a recess 73a formed on the upper surface, and an addition port 73b formed in the center of the recess 73a.

Here, if the upper surface of the gasket sheet 60 should be accidentally soiled with an additive, when the board unit 28 is attached to the sensor unit 27, the lower surface of the piping board portion 29 constituting the lower surface of the hoard unit 28 may end up being soiled by the additive.

With the configuration in this embodiment, since the recess 73a is provided, even if an additive should adhere to the bottom surface of the recess 73a when the additive is loaded, the lower surface of the board unit 28 will not come into contact with the bottom surface of the recess 73a in a state in which the board unit 28 has been attached.

Consequently, preventing an additive from adhering to the lower surface of the board unit 28 makes it possible to prevent the upper surface of the gasket sheet 60 from being soiled by the additive when the additive is loaded.

The configuration for preventing soiling by an additive is similarly applied to the additive addition portion B addition port 74.

The connecting portion 32 provided so as to extend downward from the board 31 protrudes from the lower surface of the board unit 28, and electrically connects the second working electrode pad 55 and the reference electrode pad 54 of the connection terminal portion 62 of the sensor 43 via the through-hole 78 for the reference electrode pad and the through-hole 79 for the second working electrode pad.

This electrical connection structure is the same on the side of the through-hole 76 for the first working electrode pad and the through-hole 77 for the counter electrode pad.

FIG. 23 shows a state in which the board unit 28 has been attached from above on the upper surface side of the sensor unit 27. In this state, a specific pipe of the piping board portion 29 is connected to the additive addition part A addition port 73. The same applies to the additive addition portion B addition port 74 and the stirring member air discharge and intake port 75.

Then, the connecting portion 32 extending downward from the board 31 goes through the reference electrode pad through-hole 78 and the second working electrode pad through-hole 79 and is electrically connected to the reference electrode pad 54 and the second working electrode pad 55 of the connection terminal portion 62 of the sensor 43.

This electrical connection structure is the same for the through-hole 76 for the first working electrode pad and the through-hole 77 for the counter electrode pad.

The gasket sheet 60 of the sensor unit 27 is disposed so as to cover the periphery of the through-hole 76 for the first working electrode pad, the through-hole 77 for the counter electrode pad, the through-hole 78 for the reference electrode pad, and the through-hole 79 for the second working electrode pad, which are through-holes for connecting to the additive addition portion A addition port 73, the additive addition portion B addition port 74, the stirring member air discharge and intake port 75, and the connection terminal portion 62 of the sensor 43. Consequently, the gasket sheet 60 is used for the purposes of waterproofing and preventing dew condensation.

FIG. 24 is a top view of the well plate 25.

As shown in FIG. 24, the well plate 25 has, for example, 24 wells (containers) 80 (4 vertical×6 horizontal). Each well 80 contains a liquid medium (liquid sample) for culturing cells.

The wells 80 are, for example, substantially cylindrical vessels having a diameter of 15.1 mm, into which a sensor 43 having a width of about 7.0 mm is inserted. The amount of medium (liquid sample) that is put into each well 80 is 0.5 to 1.0 mL, for example.

FIG. 25A is an oblique view of the port 61 for adding an additive to the wells 80, as viewed from below. FIG. 25B is an oblique view of the port 61 as viewed from above.

In this embodiment, the port 61 has a stirring member 81, an additive addition portion A82, and an additive addition portion B83.

The additive addition portion A82 and the additive addition portion B83 are used to add a specific additive to the medium, estimate the subsequent degree of culturing while measuring with the sensor 43, and determine the optimal cell culture method.

The additive addition portion A82 and the additive addition portion B83 have additive containers (additive A container 85, additive B container 86) having additive ports (additive A discharge port 85a, additive B discharge port 86a) as openings for adding the additive into the well 80 (culture vessel), as well as an air pressure supply unit (drive unit 3, piping tube 6, piping board portion 29) for applying air pressure to this additive container.

The additive A container 85 and the additive B container 86 each have a cylindrical shape having an opening (additive A discharge port 85a, additive B discharge port 86a) that is underneath in the usage state.

The stirring member 81 is used to stir the medium in the well 80 after the additive has been added, and to stir the additive uniformly into the medium.

As shown in FIG. 25B, the additive addition portion A addition port 73, the additive addition portion B addition port 74, and the stirring member air discharge and intake port 75 are provided on the upper surface of the port 61.

FIG. 26A is a top view of the port 61. FIG. 26B is a cross-sectional view along the F-F' line in FIG. 26A.

As shown in FIG. 26B, the lower portion of the cylindrical additive A container 85 is formed so that its inside diameter decreases toward the lower end, and the agent A discharge port 85a is provided as an opening at the lower end thereof.

A substantially annular dropping adjustment surface 88 (see FIG. 27) is formed at the outer peripheral edge of the additive A discharge port 85a.

FIG. 27 is a detail cross-sectional view of the vicinity of the additive A discharge port 85a provided at the lower end of the additive A container 85 of the port 61.

The lower end of the additive A container 85 is formed so that its outside diameter decreases toward the lower end. Therefore, as shown in FIG. 27, a substantially conical inclined surface 87 that narrows downward is formed at the lower end of the additive A container 85.

The substantially annular dropping adjustment surface 88 is provided at the outer peripheral edge of the additive A discharge port 85a so as to be disposed substantially horizontally in the usage state.

FIGS. 28A to 28C show how the additive is dropped from the lower end portion of the additive A container 85 of the additive addition portion A82.

When air pressure is gradually applied from the upper part of the additive A container 85, the additive is pushed out near the opening of the additive A discharge port 85a as shown in FIG. 28A. As shown in FIG. 28B, the additive pushed out of the additive A discharge port 85a gradually becomes a large water droplet due to surface tension. Then, as shown in FIG. 28C, the water droplet that has grown in size along the dropping adjustment surface 88 swells out to the outer periphery along the substantially horizontal dropping adjustment surface 88, and once the weight of the water droplet exceeds its surface tension, the drop falls from the A discharge port 85a.

As described above, because the dropping adjustment surface 88 is provided to the additive A discharge port 85a, the additive falls into the medium as a water droplet of the desired size. Therefore, the concentration of the additive contained in the medium can be gradually increased, which means that the additive can be added to the cells being cultured without leading to any sudden change in the concentration in which the additive is contained in the medium.

That is, in this embodiment, when air pressure is applied into the additive A container 85, the additive held in the additive A container 85 moves over to the additive A discharge port 85a side. Then, at the dropping adjustment surface 88 provided on the outer peripheral edge of the additive A discharge port 85a, the additive is held by the surface tension to form a large droplet, which then falls into the culture vessel (well 80) below once the weight of the additive becomes greater than the holding force produced by surface tension.

Also, when this drop falls, another drop of additive begins to form in the additive A discharge port 85a, and then falls as a droplet into the lower culture vessel (well 80).

That is, in this embodiment, since the additive is supplied intermittently into the culture vessel (well 80), the additive is less likely to subject the cells to sudden stress, which allows cell culture analysis to be performed properly.

FIG. 29 is a plan view of the additive A82 (additive A container 85) on the additive A discharge port 85a side.

The above-mentioned dropping adjustment surface 88 is provided at the outer peripheral edge of the opening portion of the additive A discharge port 85a. The inclined surface 87 is provided at the outer periphery of the dropping adjusting surface 88.

The dropping adjustment surface 88 is subjected to a hydrophilic treatment in an annular shape, while the inclined surface 87 is rendered hydrophobic.

Consequently, the dropping adjustment surface 88 holds the droplet using the surface tension of the additive, but when the droplet of the additive grows all the way to the inclined surface 87, the force holding the droplet by surface tension of the additive decreases, so the additive drops into the lower culture vessel (well 80).

Also, as shown in FIG. 29, the inner peripheral side (first surface) 88a of the annular dropping adjustment surface 88 may be subjected to a hydrophilic treatment, and the outer peripheral side (second surface) 88b may be subjected to a hydrophobic treatment.

In this case, the inner peripheral side 88a of the dropping adjustment surface has a force for holding a droplet, and the outer peripheral side 88b of the dropping adjusting surface does not have a force for holding a droplet. Therefore, once the droplet grows all the way to the outer peripheral side 88b, the force for holding the droplet suddenly decreases, and a drop of the additive falls into the lower culture vessel (well 80).

Next, the operation of the additive addition portion will be described with reference to FIGS. 30A to 31B.

FIG. 30A is a diagram of the first step, when the additive 90 is put into the additive A container 85.

As shown in FIG. 30A, the additive 90 is preloaded into the additive A container 85 from the additive addition portion A addition port 73 using a pipette tip 89.

FIG. 30B shows the state after the loading of the additive 90.

Since the amount of the additive 90 loaded into the additive A container 85 is less than the volume of the additive A container 85, the additive 90 does not overflow from the additive A container 85.

FIG. 30C is a detail view of the additive A discharge port 85a when the additive is loaded.

During the loading of the additive, the surface tension of the additive at the opening of the additive A discharge port 85a is greater than the gravity exerted on the additive 90, as shown in FIG. 30C, so the additive 90 is held within the agent A container 85.

FIG. 31A shows a state in which the piping board portion 29 has been connected from above after the loading of the additive.

In this state, the additive addition portion A piping line 91 included in the piping board portion 29 is linked to the additive addition portion A addition port 73 of the additive A container 85. Air pressure is then applied from the additive addition portion A piping line 91 in the piping board portion 29 linked to the additive addition portion A addition port 73 of the additive A container 85. Consequently, as shown in FIG. 31B, the additive 90 is added to the well 80.

Even after the additive 90 has been added, a small amount of the additive 90 remains in the additive A container 85. This prevents air or bubbles from being discharged from the additive A discharge port 85a.

Next, the configuration and operation of the stirring member 81 will be described with reference to FIGS. 32A to 32C.

FIG. 32A is a top view of the port 61 including the stirring member 81. FIG. 32B is a cross-sectional view along the G-G' line in FIG. 32A. FIG. 32C is a detail oblique view of a liquid discharge and intake port 93 provided at the lower end of the stirring vessel 92 of the stirring member 81.

As shown in FIGS. 32A to 32C, the stirring member 81 has the liquid discharge and intake port 93 that is provided under the stirring vessel 92 and is immersed in the medium, and an air discharge and intake port 94 that is formed on the upper surface of the stirring vessel 92.

FIG. 33A shows the initial state of the stirring member 81. FIG. 33B shows a state in which an air discharge and intake unit 95 is linked to the stirring member 81. FIG. 33C shows a state in which the air discharge and intake unit 95 acts in the direction in which air is discharged.

As shown in FIG. 33B, the air discharge and intake unit 95 is linked to the air discharge and intake port 94. The air discharge and intake unit 95 is constituted by the drive unit 3, the piping tube 6, and the piping board portion 29.

As shown in FIG. 33A, in the state before the stirring member 81 is linked to the air discharge and intake unit 95, the liquid discharge and intake port 93 is immersed in the medium in the well 80. In this state, the medium flows into the stirring vessel 92 from the liquid discharge and intake port 93, and the medium flows into the stirring vessel 92 up to almost the same height as the liquid level L1 of the medium in the well 80.

When the stirring member 81 is linked to the air discharge and intake unit 95, the air discharge and intake unit 95 first acts in the direction in which air is drawn in, as shown in FIG. 33B. Consequently, the inside of the stirring vessel 92 is under negative pressure, so the medium in the well 80 is drawn up through the liquid discharge and intake port 93, and the liquid level L2 of the medium in the stirring vessel 92 becomes higher than the liquid level L1 of the medium in the well 80.

After this, the air discharge and intake unit 95 acts in the direction in which air is discharged, as shown in FIG. 33C. Consequently, the inside of the stirring vessel 92 is under positive pressure, so the medium is discharged from the liquid discharge and intake port 93 into the well 80.

At this point, as shown in FIG. 33B, the discharged amount is the same as the amount of medium drawn in into the stirring vessel 92, so in the initial state shown in FIG. 33A, all of the medium that has flowed into the stirring vessel 92 still remains in the stirring vessel 92. Consequently, no air or bubbles are discharged from the liquid discharge and intake port 93 into the well 80.

As discussed above, the cell culture analyzer 1 of this embodiment comprises the stirring member 81 that has the liquid discharge and intake port 93 immersed in the medium, and the air discharge and intake port 94 connected to the air discharge and intake unit 95.

Consequently, there is no need for a stirring rod or plunger to be provided for each culture vessel, which allows the configuration of the device to be simplified.

That is, with the cell culture analyzer 1 in this embodiment, in the air discharge and intake unit 95, air is discharged from and drawn into to the stirring member 81, so that after the medium in the culture vessel (well 80) is drawn into the stirring member 81, the medium in the culture vessel (well 80) is stirred by being discharged.

This eliminates the need for a stirring rod or a plunger to be provided for each culture vessel, and allows the device configuration to be simplified.

Also, as shown in FIG. 32B, the liquid discharge and intake port 93 of the stirring member 81 is provided on the lower side surface of the stirring vessel 92.

Consequently, the medium discharged from the lower side surface of the stirring vessel 92 is extruded in the horizontal direction and stirred along the inner peripheral surface of the culture vessel (well 80), as shown in FIG. 34. As a result, convection can be generated in the medium in the culture vessel (well 80), and stirring can be performed up to the gap between the sensor 43 and the inner peripheral surface of the well 80, so the medium can be stirred more effectively.

Furthermore, as shown in FIG. 34, the liquid discharge and intake port 93 of the stirring member 81 is located at a position that is away from the center O in the culture vessel (well 80), that is, a position that is close to the inner peripheral surface of the culture vessel (well 80), and the opening thereof is disposed in an orientation that is opposite the inner peripheral surface of the culture vessel (well 80).

Consequently, the medium discharged from the liquid discharge and intake port 93 collides with the inner peripheral surface of the culture vessel (well 80) and circulates within the culture vessel (well 80) along the inner peripheral surface, and this stirs the entire medium in the container (well 80). As a result, the medium can be properly stirred.

Also, the distance from the liquid discharge and intake port 93 of the stirring member 81 to the additive A discharge port 85a is equal to the distance to the additive B discharge port 85b.

Thus disposing the components such that the distances from the openings (additive A discharge port 85a, additive B discharge port 86a) of the two additive addition parts (additive addition part A82, additive addition part B83) to the liquid discharge and intake port 93 of the stirring member 81 is are equal to each other means that the additive A discharge port 85a and the additive B discharge port 86a are disposed in left and right symmetry with respect to the inner peripheral surface of the culture vessel (well 80).

Consequently, the additives from the respective additive addition portions (additive addition portion A82, additive addition portion B83) are uniformly stirred in the culture vessel by the stirring member 81.

As shown in FIGS. 35A and 35B, the shape of the opening of the liquid discharge and intake port 93 may be set by taking into account ease of molding when using a material such as resin.

More specifically, as shown in FIGS. 35A and 35B, the liquid discharge and intake port 93 of the stirring member 81 is provided with an opening portion on the lower side surface of the stirring vessel 92 so that no undercut will be necessary. That is, the liquid discharge and intake port 93 shown in FIG. 35B is formed at the corner portion of the lower end portion of the stirring member 81.

This eliminates the need for an undercut during molding, which simplifies the manufacturing process and allows the port 61 to be manufactured at a lower cost.

FIG. 36A is a flowchart of an analysis method including a measurement step and an addition step including stirring and homogenization. FIG. 36B is a flowchart of the addition steps A and B included in FIG. 36A. FIG. 36C is a flowchart of the flow in the measurement step included in FIG. 36A.

The cell culture analysis method used in the cell culture analyzer 1 of this embodiment comprises two kinds of stirring steps (stirring and homogenization).

First, as shown in FIG. 36A, in the measurement step S11, the components of the medium are measured in a state in which the sensor 43 is immersed in the culture vessel (well 80), after which stirring is performed by the stirring member 81.

The stirring step included in this measurement step S11 shall be referred to as the second stirring step.

Next, the addition step A of S12 is carried out.

In the addition step A of S12, the additive is added to the well 80, which is a culture vessel, by the additive addition portion A82 or the additive addition portion B83, after which the medium is stirred by the stirring member 81.

The stirring step included in the addition step A shall be referred to as the first stirring step.

After this are carried out the measurement step S13, in which the procedure is the same as in the measurement step S11; the addition step B S14, in which the procedure is the same as in the addition step A of S12; and the measurement step S15, in which the procedure is the same as in S11 and S13. The process is then ended.

In the addition steps A and B carried out in S12 and S14, as shown in FIG. 36B, the additive is first dropped in S21, intake (stirring) is performed in S22, and discharge (stirring) is performed in S23. The intake and discharge of S22 and S23 are repeated N number of times.

In the measurement steps carried out in S11, S13, and S15, as shown in FIG. 36C, first, measurement is performed in S31, intake (uniform) is performed in S32, and discharge (uniform) is performed in S33. The intake and discharge in S32 and S33 are repeated N number of times, depending on the type of medium and additive, the amount in which the additive is added, and so forth (N=1, 2, 3, . . . ). At this point, the amounts of medium that are drawn in and discharged in the intake and discharge are substantially the same.

Thus performing first and second stirring steps during measurement and each time an additive is added allows the medium to be stirred in such a way that the additive concentration is not higher in one location than another, so measurement accuracy is improved.

Also, the absolute value of the air pressure generated by the air discharge and intake unit 95 during stirring in the first stirring step is greater than the absolute value of the air pressure generated by the air discharge and intake unit 95 during stirring in the second stirring step.

Consequently, when the additive is added, a more powerful stirring operation can be performed, and during measurement, a gentler stirring operation can be performed as compared with that at the time of addition.

Thus stirring forcefully when the additive is added and stirring more gently during measurement as compared with that at the time of adding the additive allows the stirring to be performed more reliably, and improves the measurement accuracy.

In the cell culture analyzer 1 of this embodiment, as discussed above, after the additive has been added to the medium using the additive addition portion A82 or the additive addition portion B83, the stirring member 81 performs the first stirring operation. Then, when the sensor 43 measures the components of the medium, the stirring member 81 performs the second stirring operation.

At this point, the absolute values of the air pressures associated with discharge and intake from and to the air discharge and intake unit 95 during the first stirring operation are greater than the absolute values of the air pressures associated with discharge and intake from and to the air discharge and intake unit 95 during the second stirring operation.

Consequently, the stirring can be stronger during the addition of the additive and gentler during measurement as compared with that at the time of adding the additive, which means that the proper stirring can be performed for each step, and the accuracy of measurement using the sensor 43 will be improved.

Also, when the sensor 43 measures the components of the medium in the culture vessel (well 80), the second stirring operation is halted.

Consequently, the concentration distribution of the medium will be more uniform, and measurement accuracy is further improved.

FIG. 37 is an exploded oblique view of a seal 96 that is affixed to the upper surface of the sensor unit 27.

As shown in FIG. 37, a plurality of port input/output portions 72 connected to the upper surface of the port 61 are disposed in a plurality of openings formed in the gasket sheet 60 disposed on the upper surface side of the sensor unit 27.

As described above, each port input/output portion 72 has an additive addition part A addition port (upper surface opening) 73, an additive addition part B addition port (upper surface opening) 74, a stirring member air discharge and intake port 75, and four through-holes for connecting to the connection terminal portion 62 of the sensor 43 (through-hole 76 for the first working electrode pad, through-hole 77 for the counter electrode pad, through-hole 78 for the reference electrode pad, and through-hole 79 for the second working electrode pad).

Thus, a plurality of openings are disposed in the plurality of port input/output portions 72 disposed in the plurality of openings formed in the gasket sheet 60.

In this embodiment, the seal 96 is provided, which can be affixed to a plurality of openings in a removable state. More specifically, the seal 96 is used to seal off the opening of the port input/output portion 72 located above an unused well 80.

Since an opening in the board (gasket sheet 60) corresponding to an unused culture vessel (well 80) is covered with the seal 96, this prevents air from leaking out through the additive container (additive A container 85, additive B container 86) disposed at the position corresponding to that opening. Meanwhile, an appropriate air pressure is applied to an additive container (additive A container 85, additive B container 86) disposed at a position corresponding to the opening corresponding to a culture vessel (well 80) that is being used, and the additive can be supplied appropriately.

Also, cell culture analysis can be performed by simply removing a part of the seal 96 affixed to the position corresponding to a culture vessel that is being used (additive A container 85, additive B container 86) from the gasket sheet (base) 60, and this makes the job easier.

That is, as shown in FIG. 37, the seal 96 is configured by affixing a bottom seal 96a and a top seal 96b one over the other.

More specifically, as shown in FIG. 38A, the seal 96 (bottom seal 96a and top seal 96h) is affixed by means of the adhesive force of a plurality of adhesive portions 97 disposed on the upper surface of the gasket sheet 60 on the upper surface of the sensor unit 27, in the left-right direction in the drawing.

As shown in FIG. 38B, the bottom seal 96a has a single overall peeling tab 96aa, plurality of individual peeling tabs 96ab, cut portions 96ac, and perforated portions 96ad.

The overall peeling tab 96aa is a portion that is grasped in the user's fingers when the entire bottom seal 96a is to be peeled off, and is provided along the lengthwise direction from the lower end portion of the short side of the substantially rectangular bottom seal 96a.

The individual peeling tabs 96ab are portions that are grasped in the user's fingers when a bottom seal 96a is to be partially peeled off, and are provided in a direction intersecting the long side of the substantially rectangular bottom seal 96a in the lengthwise direction.

The cut portions 96ac are cuts formed between adjacent individual peeling tabs 96ab, and are formed substantially parallel to the short side of the bottom seal 96a. Also, the cut portions 96ac are formed from the end of the bottom seal 96a to a position about two-thirds of the way along the short side. The cut portions 96ac are formed by making cuts from the long side of the bottom seal 96a on the side where the individual peeling tabs 96ab are provided.

The perforated portions 96ad are formed at positions contiguous with the cut portions 96ac, and are formed from the end of the bottom seal 96a to a position about one-third of the way along the short side. The perforated portions 96ad are formed from the end on the side where the overall peeling tab 96aa is formed.

Consequently, when the user grasps the overall peeling tab 96aa and peels off the bottom seal 96a, the entire bottom seal 96a can be peeled off at once because it is connected at the perforated portions 96ad.

Meanwhile, when user grasps an individual peeling tab 96ab and peels off a part of the bottom seal 96a, a part of the bottom seal 96a can be easily peeled off at the desired position by simply peeling off from the cut side of the cut portions 96ac and thereby tearing along the perforated portion 96ad.

As shown in FIG. 38C, the top seal 96h has an overall peeling tab 96ba, individual peeling tabs 96bb, cut portions 96bc, and perforated portions 96bd.

The overall peeling tab 96ba is a portion that is grasped in the user's fingers when the entire top seal 96b is to be peeled off, and is provided along the lengthwise direction from the lower end portion of the short side of the substantially rectangular top seal 96h.

The individual peeling tabs 96bb are portions that are grasped in the user's fingers when the top seal 96b is to be partially peeled off, and are provided in a direction intersecting the long side of the substantially rectangular bottom seal 96a in the lengthwise direction.

The cut portions 96bc are cuts formed between adjacent individual peeling tabs 96bb, and are formed substantially parallel to the short side of the top seal 96b. Also, the cut portions 96bc are formed from the end of the top seal 96b to a position about two-thirds of the way along the short side. The cut portions 96bc are formed by making cuts from the long side of the bottom seal 96a on the side where the individual peeling tabs 96bb are provided.

The perforated portions 96bd are formed at positions contiguous with the cut portions 96bc, and are formed from the end of the top seal 96b to a position about one-third of the way along the short side. The perforated portions 96bd are formed from the end on the side where the overall peeling tab 96ba is formed.

Consequently, in a state in which the bottom seal 96a and the top seal 96b shown in FIG. 38D have been affixed, when the user grasps the overall peeling tab 96ba and peels off the top seal 96b, the entire top seal 96b can be peeled off at once because it is connected at the perforated portions 96bd.

Meanwhile, when user grasps an individual peeling tab 96*ab* and peels off a part of the top seal 96*b*, a part of the top seal 96*b* can be easily peeled off at the desired position by simply peeling off from the cut side of the cut portions 96*bc* and thereby tearing along the perforated portion 96*bd*.

In a state in which the bottom seal 96*a* and the top seal 96*b* have been attached to the upper surface of the sensor unit 27, as shown in FIG. 38D, the overall peeling tabs 96*aa* and 96*ba* of the bottom seal 96*a* and the top seal 96*b* are disposed in positions that do not overlap with each other.

Consequently, when the overall peeling tab 96*ba* is grasped to peel off only the top seal 96*b*, this prevents the user from accidentally grasping all the way to the overall peeling tab 96*aa* of the bottom seal 96*a*.

Here, as discussed above, the sensor unit 27 in this embodiment is provided to the user in a state in which the bottom seal 96*a* and the top seal 96*b* have been attached to the upper surface. The user then peels off all or part of the bottom seal 96*a* and/or the top seal 96*b* of the row to be used, corresponding to the position of the well 80 to be used, and this prevents unnecessary additive from being added to a well 80 that is not to be used.

Also, the bottom seal 96*a* and the top seal 96*b* are affixed to the adhesive portions 97 on the upper surface of the gasket sheet 60.

Consequently, the seal 96 is affixed to the upper surface of the gasket sheet 60 via the adhesive portions 97 provided at positions that are offset from the additive addition portions A82 and B83, so the seal 96 does not need to be directly affixed to the upper surface of the additive addition portions A82 and B83. This means that it is not necessary to provide an adhesive agent on the upper surfaces of the additive addition portions A82 and B83, so the adhesive is prevented from becoming admixed.

Here, in this embodiment, as shown in FIG. 39A, the sensor unit 27 is provided to the user in a state in which the bottom seal 96*a* and the top seal 96*b* have been affixed to the upper surface of the gasket sheet 60.

At this point, in the state provided to the user, the various opening portions are as follows. Electrode pad portion 98: OPEN, additive addition portion A82: CLOSED, additive addition portion B83: CLOSED, stirring member 81: CLOSED.

When in the additive addition portion A82 is filled with an additive, as shown in FIG. 39B, the overall peeling tab 96*ba* is grasped and just the top seal 96*b* is peeled off.

At this point, the various opening portions are as follows after the top seal 96*b* has been peeled off. Electrode pad portion 98: OPEN, additive addition portion A82: OPEN, additive addition portion B83: CLOSED, stirring member 81: OPEN.

Furthermore, when additive addition portion A82 is filled with an additive, as shown in FIG. 39B, the overall peeling tab 96*aa* is grasped and the bottom seal 96*a* is also peeled off.

At this point, the various opening portions are as follows after the bottom seal 96*a* has been peeled off. Electrode pad portion 98: OPEN, additive addition portion A82: OPEN, additive addition portion B83: OPEN, stirring member 81: OPEN.

Consequently, the bottom seal 96*a* and the top seal 96*b* can be peeled off in just a few steps.

In this embodiment, all or part of these two seals 96*a* and 96*b* is selectively peeled off according to the position of the culture vessel to be used, which allows the openings in the board portion corresponding to the upper surface of the culture vessels (wells 80) that will not be used to be sealed off by the seal 96. This makes the product more convenient to use for the user.

For example, in the usage scenarios 1 to 5 shown in FIG. 40, all or part of the seal 96 is peeled off depending on the openings of the port 61 to be used.

In usage scenario 1, as shown in FIG. 40, when neither port A nor port B is to be used, that is, when the medium is to be measured without adding any additive, the product is used just as it is provided to the user, without the seal 96 being peeled off.

In usage scenario 2, as shown in FIG. 40, when only the first and second rows of the port A are used, and the port B is not used, the individual peeling tab 96*bb* of the second row of the top seal 96*b* is peeled off, and the product is used in a state in which the openings in the first and second rows of the port A are OPEN.

In usage scenario 3, as shown in FIG. 40, when all the rows of the port A are used and the port B is not used, the overall peeling tab 96*ba* for the top seal 96*b* is peeled off, and the product is used in a state in which the openings in all the rows of the port A are OPEN.

In usage scenario 4, as shown in FIG. 40, when only the first and second rows of the port A and only the first and second rows of the port B are used, the individual peeling tab 96*bb* of the second row of the top seal 96*b* is peeled off, the individual peeling tab 96*ab* in the second row of the bottom seal 96*a* is peeled off, and the product is used in a state in which the openings in the first and second rows of the ports A and B are OPEN.

In usage scenario 5, as shown in FIG. 40, when all the rows of ports A and B are used, the overall peeling tab 96*aa* of the bottom seal 96*a* is peeled off, so that top seal 96*b* affixed to the upper surface of the bottom seal 96*a* is also peeling off, and the product is used in a state in which the openings in all the rows of the ports A and B are OPEN.

This configuration in which the seal 96 is used is similarly applied to the stirring member air discharge and intake port 75.

That is, the stirring member air discharge and intake port 75 is sealed off above any unused wells 80 by using the seal 96, which allows the appropriate air pressure to be applied just to the stirring member 81 being used.

In this case, cell culture analysis can be performed by removing the seal 96 corresponding to the upper surface of the stirring member 81 to be used, which makes the work easier.

Embodiment 2

A cell culture analyzer according to another embodiment of the present invention will now be described with reference to the appended drawings.

The cell culture analyzer in this embodiment differs from Embodiment 1 above in that a port (additive supply member) 161 including the stirring member 181 shown in FIGS. 41A and 41B is used instead of the stirring member 81 shown in FIGS. 32A to 32C, etc.

As to the rest of the configuration, members having the same configuration and function will be numbered the same and will not be described again.

FIG. 41A is a top view of the port 161 including the stirring member 181. FIG. 41B is a cross-sectional view along the line in FIG. 41A.

As shown in FIGS. 41A and 41B, the stirring member 181 has a liquid discharge and intake port 193 that is provided below the stirring vessel 192 and is immersed in the medium, and an air discharge and intake port 194 that is formed on the upper surface of the stirring vessel 192.

In the stirring member 181, when the stirring step is commenced, the liquid discharge and intake port 193 is immersed in the medium in the well 80 as shown in FIG. 41B. In this state, the medium flows from the liquid discharge and intake port 193 into the stirring vessel 192, and flows into the stirring vessel 192 to roughly the same height as the liquid level L1 of the medium in the well 80.

Then, when the stirring member 181 is connected to the above-mentioned air discharge and intake unit 95 (see FIG. 33B), the air discharge and intake unit 95 acts in the direction of drawing in air, which puts the inside of the stirring vessel 192 under negative pressure, and draws the medium in the well 80 up through the liquid discharge and intake port 193, so that the liquid level of the medium in the stirring vessel 192 becomes higher than the liquid level L1 of the medium in the well 80.

After this, the air discharge and intake unit 95 acts in the direction of discharging air to put the inside of the stirring vessel 192 under positive pressure and discharge the medium from the liquid discharge and intake port 193 into the well 80.

Furthermore, in this embodiment, the liquid discharge and intake port 193 provided on the lower side surface of the stirring vessel 192 shown in FIG. 42A discharges or draws in the medium toward the side wall of the well 80.

Also, as shown in FIG. 42B, the stirring vessel 192 has on its inner surface an inclined surface 192a that is provided to the portion opposite the liquid discharge and intake port 193 and is formed so as to angle downward toward the liquid discharge and intake port 193, and a horizontal surface 192b that is provided between the inclined surface 192a and the liquid discharge and intake port 193.

The inclined surface 192a is a part of the inner wall surface near the bottom surface of the stirring vessel 192, is disposed at a position opposite the liquid discharge and intake port 193, and is formed so as to angle downward toward the liquid discharge and intake port 193.

Consequently, providing the inclined surface 192a to the portion facing the liquid discharge and intake port 193 makes it possible to suppress the generation of air bubbles in the corner portion opposite the liquid discharge and intake port 193. This prevents bubbles from being discharged from the liquid discharge and intake port 193, which suppresses the generation of spray that could be a source of contamination, so bubbles will not directly collide with the cells adhering to on the bottom surface of the well 80, and it is less likely that there will be an adverse effect on the cells.

The horizontal surface 192b is a bottom surface formed substantially horizontally in an orientation in which the stirring vessel 192 is immersed in the medium, and is formed as a surface linking the lower end portion of the inclined surface 192a and the liquid discharge and intake port 193.

Consequently, since the inclined surface 192a is provided in a state in which the horizontal surface 192b remains on the bottom surface of the stirring vessel 192, it is possible to generate a flow of medium toward the inner side wall of the well 80.

Furthermore, as shown in FIG. 42A, since the shape of the lower end portion of the stirring vessel 192 eliminates the need for undercut during molding, the manufacturing process is simpler, and the port 161 can be manufactured at a lower cost.

Embodiment 3

The cell culture analyzer according to yet another embodiment of the present invention will now be described with reference to the appended drawings.

As shown in FIG. 43A, the cell culture analyzer in this embodiment differs from Embodiment 1 above in that the port (additive supply member) 261 including the stirring member 281 shown in FIGS. 43A and 43B is used instead of the stirring member 81 shown in FIGS. 32A to 32C, etc.

As to the rest of the configuration, members having the same configuration and function will be numbered the same and will not be described again.

FIG. 43A is a top view of the port 261 including the stirring member 281. FIG. 43B is a plan view of the flow of the medium discharged from the stirring member 281.

In this embodiment, as shown in FIGS. 43A and 43B, the stirring member 281 comprises three openings (liquid discharge and intake ports 293a, 293b, 293c) for discharging the medium in different directions, as liquid discharge and intake ports.

As shown in FIG. 43B, the discharge and intake port 293a is formed so as to open toward the inner wall surface of the well 80, and discharges the drawn-in medium to the inner wall surface of the well 80.

Consequently, the medium discharged from the liquid discharge and intake port 293a collides with the inner wall surface of the well 80 and circulates around the well 80 along the inner peripheral surface, which stirs the entire medium in the well 80, so the medium can be sufficiently stirred.

As shown in FIG. 43B, the discharge and intake port 293b is formed so as to open toward the additive A discharge port 85a, and discharges the drawn-in medium to the position where the additive A is discharged.

As shown in FIG. 43B, the discharge and intake port 293c is formed so as to open toward the additive B discharge port 86a, and discharges the drawn-in medium to the position where the additive B is discharged.

Consequently, once the medium has been drawn in, it can be split up and discharged from the plurality of liquid discharge and intake ports 293a to 293c, which allows the flow rate of the discharged medium to be kept lower. Also, since the liquid discharge and intake ports 293h and 293c can send the medium toward the positions where the additive A and the additive B are discharged, respectively, the stirring effect of the additives A and B can be improved.

As a result, the stirring step can be performed more efficiently, without generating a strong flow rate in the discharged medium, which allows gentle stirring to be performed, without subjecting the cells in the well 80 to a load.

Furthermore, just as in Embodiments 1 and 2 above, the shape of the lower end portion of the stirring vessel 292 eliminates the need for undercut during molding, so the manufacturing process is simpler, and the port 261 can be manufactured at a lower cost.

Embodiment 4

The cell culture analyzer according to yet another embodiment of the present invention will now be described with reference to the appended drawings.

As shown in FIG. 44A, the cell culture analyzer in this embodiment differs from Embodiment 1 above in that the port (additive supply member) 361 including the stirring member 381 shown in FIGS. 44A and 44B is used instead of the stirring member 81 shown in FIGS. 32A to 32C, etc.

As to the rest of the configuration, members having the same configuration and function will be numbered the same and will not be described again.

FIG. 44A is a lateral cross-sectional view showing a state in which the port 361 including the stirring member 381 is immersed in the medium contained in the well 80. FIG. 44B is a lateral cross-sectional view showing a state in which the port 361 has been pulled up from the state shown in FIG. 44A.

In this embodiment, as shown in FIGS. 44A and 44B, a small-diameter portion 394 having an inside diameter smaller than that of the upper portion is formed in the lower part of the stirring vessel 392 of the stirring member 381 of the port 361.

As shown in FIG. 44A, etc., because the small-diameter portion 394 has a smaller inside diameter than the portion above the small-diameter portion 394 of the stirring vessel 392, the volume is smaller for a given length. The small-diameter portion 394 is provided from the position of the liquid discharge and intake port 393 to a position higher than the liquid level L1 of the medium, in an orientation of being immersed in the medium in the well 80.

Consequently, as shown in FIG. 44B, the residual medium 394a remaining inside the stirring member 381 after being pulled up from the medium can be reduced as much as possible. Therefore, only a tiny amount of medium will be wasted, and it is possible to avoid adversely affecting the subsequent cell culture step.

Embodiment 5

The cell culture analyzer according to yet another embodiment of the present invention will now be described with reference to the appended drawings.

As shown in FIG. 45A, etc., the cell culture analyzer of this embodiment differs from Embodiment 4 above in that a substantially annular rib 395 is additionally provided to the upper end portion of the small-diameter portion of the stirring member 381 described in Embodiment 4 above.

As to the rest of the configuration, members having the same configuration and function will be numbered the same and will not be described again.

As shown in FIGS. 45A and 45B, the rib 395 is provided to the upper end portion of the small-diameter portion 394, that is, to a portion of an inclined surface that links the small-diameter portion 394 in the stirring vessel 392 with the other large-diameter portion. As shown in FIG. 46, the rib 395 is formed so as to protrude inward in the radial direction from the inner peripheral surface of the stirring vessel 392.

Consequently, for example, any medium that rises up in the small-diameter portion 394 due to capillary action or the like will be held back by the rib 395, and as shown in FIG. 45B, the amount of the residual medium 394a after the stirring step is completed can be kept at or below a certain level.

Embodiment 6

The cell culture analyzer according to yet another embodiment of the present invention will now be described with reference to the appended drawings.

The cell culture analyzer of this embodiment is constituted by a combination of the small-diameter portion 394 described in the above Embodiments 4 and 5, the rib 395 described in the above Embodiment 5, and the liquid discharge and intake port 193 disposed opposite the inclined surface 192a described in the above Embodiment 2.

As to the rest of the configuration, members having the same configuration and function will be numbered the same and will not be described again.

The liquid discharge and intake port 193 is formed at the distal end of the small-diameter portion 394, and as described in Embodiment 2 above, draws in or discharges the medium toward the side wall of the well 80.

Also, the stirring vessel 392 has an inclined surface 192a that is provided on the inner surface thereof at the portion opposite the liquid discharge and intake port 193 and is formed so as to angle downward toward the liquid discharge and intake port 193, and a horizontal surface 192b that is provided between the inclined surface 192a and the liquid discharge and intake port 193.

The inclined surface 192a is a part of the inner wall surface near the bottom surface of the stirring vessel 392, is disposed at a position opposite the liquid discharge and intake port 193, and is formed so as to angle downward toward the liquid discharge and intake port 193.

Consequently, providing the inclined surface 192a to the portion opposite the liquid discharge and intake port 193 makes it less likely that air bubbles will be generated in the corner portion opposite the liquid discharge and intake port 193. This prevents bubbles from being discharged from the liquid discharge and intake port 193, which suppresses the generation of spray that could be a source of contamination, so bubbles will not directly collide with the cells adhering to on the bottom surface of the well 80, and it is less likely that there will be an adverse effect on the cells.

Also, as shown in FIG. 47A, a small-diameter portion 394 having an inside diameter smaller than that of the upper portion is formed in the lower portion of the stirring vessel 392 of the stirring member 381.

As shown in FIG. 47A, the small-diameter portion 394 has a smaller inside diameter than the portion above the small-diameter portion 394 of the stirring vessel 392, so the volume is smaller for a given length. The small-diameter portion 394 is provided from the position of the liquid discharge and intake port 393 to a position higher than the liquid level L1 of the medium, in an orientation of being immersed in the medium in the well 80.

Consequently, the amount of residual medium 394a left inside the stirring member 381 after being pulled up from the medium can be kept as small as possible. Therefore, only a tiny amount of medium will be wasted, and it is possible to avoid adversely affecting the subsequent cell culture step.

Furthermore, as shown in FIG. 47A, the rib 395 is provided to the upper end portion of the small-diameter portion 394, that is, to a portion of an inclined surface that links the small-diameter portion 394 in the stirring vessel 392 with the other large-diameter portion. The rib 395 is formed so as to protrude inward in the radial direction from the inner peripheral surface of the stirring vessel 392.

Consequently, for example, any medium that rises up in the small-diameter portion 394 due to capillary action or the like will be held back by the rib 395, and the amount of the residual medium 394a after the stirring step is completed can be kept at or below a certain level.

INDUSTRIAL APPLICABILITY

The cell culture analyzer of the present invention eliminates the need for a stirring rod or plunger to be readied for each culture vessel, and has the effect of affording a more compact size, and as such can be broadly applied to various devices used for cell culture analysis.

REFERENCE SIGNS LIST 1 cell culture analyzer
2 analysis unit
3 drive unit
3a housing
4 control unit
5 electrical cable
6 piping tube
7 culture incubator
8 door
9 syringe
10 plunger
11 multi-directional switching valve
12 motor
13 motor
N, 15, 16, 17 valves
18 rotating portion
19 rotating flow path
20 adapter unit
21 top unit
22 bottom unit
23 front opening
24 adapter bottom
25 well plate
26 adapter top
27 sensor unit
28 board unit
29 piping board
30 board base
30a contact through-hole
31 board
32 connecting portion
33, 34, 35, 36 piping tubes
37 air inlet (intake port)
38 through-hole
39 piping tube connecting portion
40 leg portion (support)
41 through-hole
42 positioning hole
43 sensor
43a main body portion
44 bent portion
45 lateral edge portion
46 vertical edge portion
47 first working electrode
48 counter electrode
49 reference electrode
50 second working electrode
51 protective membrane
52 first working electrode pad
53 counter electrode pad
54 reference electrode pad
55 second working electrode pad
56 resist film
57 bottom plate
58 middle plate
59 top plate
60 gasket sheet (board)
61 port (additive supply member)
62 connection terminal portion
63 fixing portion
64 slide guide protrusion
65 through-hole
66 sensing electrode
67 positioning unit
68 slide hole
69 fixed portion
70 support portion
71 pressing portion
72 port input/output portion
73 additive addition portion A addition port (upper surface opening)
73a recess
73b addition port
74 additive addition portion B addition port (upper surface opening)
75 stirring member air discharge and intake port
76 through-hole for first working electrode pad
77 through-hole for counter electrode pad
78 through-hole for reference electrode pad
79 through-hole for second working electrode pad
80 well (culture vessel)
81 stirring member
82 additive addition portion A
83 additive addition portion B
85 additive A container (additive container)
85a additive A discharge port (opening)
86 additive B container (additive container)
86a additive B discharge port (opening)
87 inclined surface
88 dropping adjustment surface
88a inner peripheral side (first surface)
88b outer peripheral side (second surface)
89 pipette tip
90 additive
91 additive addition portion A piping line
92 stirring vessel
93 liquid discharge and intake port
94 air discharge and intake port
95 air discharge and intake part
96 seal
96a bottom seal
96aa entire peeling tab
96ab individual peeling tab
96ac cut portion
96ad perforated portion
96b top seal
96ba entire peeling tab
96bh individual peeling tab
96bc cut portion
96b perforated portion
97 adhesive portion
98 electrode pad portion
161 port (additive supply member)
175 stirring member air discharge and intake port
181 stirring member
192 stirring vessel
192a inclined surface
192b horizontal surface
193 liquid discharge and intake port
194 air discharge and intake port
261 port (additive supply member)
281 stirring member
292 stirring vessel
293a, 293h, 293c liquid discharge and intake ports
361 port (additive supply member)
381 stirring member
392 stirring vessel
393 liquid discharge and intake port
394 small-diameter portion 394a residual medium
395 rib
L1 liquid level

The invention claimed is:

1. A sensor unit having a sensor for measuring components of a medium in a culture vessel, comprising:
    a sensor having a main body portion, a measurement unit that is disposed on the main body portion and configured to measure the components of the medium, and a connection terminal portion that is electrically connected to the measurement unit; and
    a board having a connecting portion that is connected to the connection terminal portion of the sensor, and a wiring pattern that is connected to the connecting portion,
    wherein the sensor has a bent portion in which a connecting part of the main body portion and the board is bent at a substantially right angle so that a measurement portion of the sensor projects downward and is immersed in the medium in the culture vessel in a state in which the connection terminal portion and the connecting portion of the board are connected.

2. The sensor unit according to claim 1,
    wherein a plurality of the sensors are connected to the board.

3. The sensor unit according to claim 1, further comprising:
    a bottom plate that is provided below the connection terminal portion of the sensor;
    a middle plate that is provided above the connection terminal portion of the sensor; and
    a top plate that is provided above the middle plate.

4. The sensor unit according to claim 3,
    wherein the connection terminal portion of the sensor is positioned by being sandwiched between the middle plate and the bottom plate from above and below.

5. The sensor unit according to claim 3,
    wherein the bottom plate has a plurality of through-holes through which passes the sensor that has been bent downwards.

6. The sensor unit according to claim 5,
    wherein the bottom plate further has a support portion that is provided to an opening edge of the through-hole and configured to support a bottom edge side of the bent portion of the sensor, and
    the top plate has a pressing portion that is provided to a portion opposite the support portion and configured to push down on an top edge side of the bent portion of the sensor.

7. The sensor unit according to claim 6,
    wherein the support portion has a curved upper surface shape, and the pressing portion has a curved lower surface shape.

8. The sensor unit according to claim 3,
    wherein the middle plate and the bottom plate have a sensor positioning portion configured to position the connection terminal portion of the sensor, and a fixing portion configured to fix the middle plate and the bottom plate in a vertical direction with respect to the sensor positioning portion.

9. The sensor unit according to claim 8,
    wherein the fixing portion includes a prong and a prong mating portion configured to fit together by sliding in a substantially horizontal direction.

10. The sensor unit according to claim 9,
    wherein the fixing portion further includes a slide guide configured to guide a direction of sliding in the substantially horizontal direction.

11. The sensor unit according to claim 10,
    wherein a sliding direction is a direction substantially parallel to a diagonal line across the bottom plate.

12. The sensor unit according to claim 1,
    wherein the sensor is substantially L-shaped, and the bent portion is provided on an upper portion of a lengthwise edge of the sensor.

13. The sensor unit according to claim 1,
    wherein the sensor is substantially I-shaped, and the bent portion is provided on an upper portion of a lengthwise edge of the sensor.

14. A cell culture analyzer, comprising:
    the sensor unit according to claim 1; and
    a culture vessel installation unit on which the sensor unit is placed.

15. The cell culture analyzer according to claim 14,
    further comprising a support configured to form a housing space in which to install the culture vessel, provided between the sensor unit and the culture vessel installation unit.

16. The cell culture analyzer according to claim 14,
    further comprising a control unit that is disposed on the sensor unit and controls the sensor unit.

* * * * *